(12) United States Patent
Yaghi et al.

(10) Patent No.: US 9,269,473 B2
(45) Date of Patent: Feb. 23, 2016

(54) CONDUCTIVE OPEN FRAMEWORKS

(75) Inventors: Omar M. Yaghi, Berkeley, CA (US);
Shun Wan, Santa Monica, CA (US);
Christian J. Doonan, Eastwood (AU);
Bo Wang, Beijing (CN); Hexiang Deng,
Albany, CA (US)

(73) Assignee: The Regents of the University of California, Oakland, CA (US)

( * ) Notice: Subject to any disclaimer, the term of this patent is extended or adjusted under 35 U.S.C. 154(b) by 269 days.

(21) Appl. No.: 13/876,126

(22) PCT Filed: Sep. 27, 2011

(86) PCT No.: PCT/US2011/053423
§ 371 (c)(1),
(2), (4) Date: Nov. 11, 2013

(87) PCT Pub. No.: WO2012/082213
PCT Pub. Date: Jun. 21, 2012

(65) Prior Publication Data
US 2014/0081014 A1    Mar. 20, 2014

Related U.S. Application Data

(60) Provisional application No. 61/386,927, filed on Sep. 27, 2010.

(51) Int. Cl.
*B01J 20/22* (2006.01)
*H01B 1/12* (2006.01)
*B01J 20/26* (2006.01)
*C07D 487/22* (2006.01)

(52) U.S. Cl.
CPC . *H01B 1/12* (2013.01); *B01J 20/22* (2013.01); *B01J 20/26* (2013.01); *C07D 487/22* (2013.01); *Y02E 60/324* (2013.01)

(58) Field of Classification Search
CPC ...... C07D 487/22; H01B 1/12; Y02E 60/324; B01J 20/22; B01J 20/26
USPC ...... 96/108; 502/400, 526; 540/145
See application file for complete search history.

(56) References Cited

U.S. PATENT DOCUMENTS

| | | |
|---|---|---|
| 6,617,467 B1 | 9/2003 | Muller et al. |
| 7,652,132 B2 | 1/2010 | Yaghi et al. |
| 7,662,746 B2 | 2/2010 | Yaghi et al. |

(Continued)

FOREIGN PATENT DOCUMENTS

| | | |
|---|---|---|
| EP | 1674555 A1 | 6/2006 |
| WO | 2004101575 A2 | 11/2004 |

(Continued)

OTHER PUBLICATIONS

Andrew et al., "Post-Synthetic Modification of Tagged MOFs," Angew. Chem. Int. Ed. 47:8482-8486 (2008).

(Continued)

*Primary Examiner* — Frank Lawrence
(74) *Attorney, Agent, or Firm* — Joseph R. Baker, Jr.; Gavrilovich, Dodd & Lindsey LLP

(57) ABSTRACT

The disclosure relates generally to materials that comprise conductive covalent organic frameworks. The disclosure also relates to materials that are useful to store and separate gas molecules and sensors.

30 Claims, 20 Drawing Sheets

(56) References Cited

U.S. PATENT DOCUMENTS

| | | | |
|---|---|---|---|
| 7,799,120 | B2 | 9/2010 | Yaghi et al. |
| 2008/0184883 | A1 | 8/2008 | Zhou et al. |
| 2010/0132549 | A1 | 6/2010 | Yaghi et al. |
| 2010/0143693 | A1 | 6/2010 | Yaghi et al. |
| 2010/0186588 | A1 | 7/2010 | Yaghi et al. |
| 2010/0286022 | A1 | 11/2010 | Yaghi et al. |
| 2011/0137025 | A1 | 6/2011 | Yaghi et al. |
| 2013/0047849 | A1* | 2/2013 | Zhang et al. ............ 95/130 |
| 2014/0037944 | A1* | 2/2014 | Dichtel et al. ............ 428/336 |
| 2014/0148596 | A1* | 5/2014 | Dichtel et al. ............ 540/465 |

FOREIGN PATENT DOCUMENTS

| | | |
|---|---|---|
| WO | 2006072573 A2 | 7/2006 |
| WO | 2006116340 A1 | 11/2006 |
| WO | 2007054581 A1 | 5/2007 |
| WO | 2007098263 A2 | 8/2007 |
| WO | 2007101241 A2 | 9/2007 |
| WO | 2007111739 A2 | 10/2007 |
| WO | 2008091976 A1 | 7/2008 |
| WO | 2008138989 A1 | 11/2008 |
| WO | 2008140788 A1 | 11/2008 |
| WO | 2009020745 A9 | 2/2009 |
| WO | 2009042802 A1 | 4/2009 |
| WO | 2009056184 A1 | 5/2009 |
| WO | 2009149381 A3 | 12/2009 |
| WO | 2010078337 A1 | 7/2010 |
| WO | 2010088629 A1 | 8/2010 |
| WO | 2010090683 A1 | 8/2010 |
| WO | 2010148276 A3 | 12/2010 |
| WO | 2010148296 A3 | 12/2010 |
| WO | 2010148374 A3 | 12/2010 |
| WO | 2011014503 A1 | 2/2011 |
| WO | 2011038208 A2 | 3/2011 |

OTHER PUBLICATIONS

Baharlou, Simin. International Preliminary Report on Patentability for PCT/US2009/046463. Date of Mailing: Dec. 16, 2010.
Banerjee et al., "High-Throughput Synthesis of Zeolitic Imidazolate Frameworks and Application to CO2 Capture," Science 319:939-943 (2008).
Banerjee et al., "Control of Pore Size and Functionality in Isoreticular Zeolitic Imidazolate Frameworks and their Carbon Dioxide Selective Capture Properties," J. Am. Chem. Soc. 131:3875-3877 (2009).
Barman et al., "Azulene Based Metal-Organic Frameworks for Strong Adsorption of H2," Chem. Commun. 46: 7981-7983 (2010).
Barton et al., "Tailored Porous Materials," Chem. Mater. 11:2633-2656 (1999).
Bloch et al., "Metal Insertion in a Microporous Metal-Organic Framework Lined with 2,2'-Bipyridine" J. Am. Chem. Soc. 132:14382-14384 (2010).
Braun et al., "1,4-Benzenedicarboxylate Derivatives as Links in the Design of Paddle-Wheel Units and Metal-Organic Frameworks," Chem. Commun. 24:2532-2533 (2001).
Britt et al., "Highly efficient separation of carbon dioxide by a metal-organic framework replete with open metal sites," Proc. Natl. Acad. Sci. USA 106:20637-20640 (2009).
Carlucci, Lucia et al., "Polycatenation, polythreading and polyknotting in coordination network chemistry" Coordination Chemistry Reviews 246, 2003, pp. 247-289.
Caskey et al., "Dramatic Tuning of CO2 Uptake via Metal Substitution in a Coordination Polymer with Cylindrical Pores," JACS 130(33):10870-10871 (2008).
Caskey et al., "Selected Applications of Metal-Organic Frameworks in Sustainable Energy Technologies," Material Matters 4.4:111 (2009).
Centrone et al., "Raman Spectra of Hydrogen and Deuterium Adsorbed on a Metal-Organic Framework," Chem. Phys. Lett. 411:516-519 (2005).

Chae et al., "Tertiary Building Units: Synthesis, Structure, and Porosity of a Metal-Organic Dendrimer Framework (MOD-1)," J. Am. Chem. Soc. 123:11482-11483 (2001).
Chae et al., "Design of Frameworks with Mixed Triangular and Octahedral Building Blocks Exemplified by the Structure of [Zn4O(TCA)2] Having the Pyrite Topology," Angew. Chem. Int. Ed. 42:3907-3909 (2003).
Chae et al., "A Route to High Surface Area, Porosity and Inclusion of Large Molecules in Crystals," Nature427, 523-527 (2004); Featured in (1) Chemical & Engineering News magazine, Feb. 9, 2004, (2) BBC World Service, Feb. 4, (3) New Scientist, Feb. 4.
Chen et al., "Cu2(ATC)6H2O: Design of Open Metal Sites in Porous Metal-Organic Crystals (ATC: 1,3,5,7-adamantane tetracarboxylate)," J. Am. Chem. Soc. 122:11559-11560 (2000).
Chen et al., "Interwoven Metal-Organic Framework on a Periodic Minimal Surface with Extra-Large Pores," Science 291:1021-1023 (2001); Featured in Chemical and Engineering News, Feb. 21, 2001.
Chen et al., "Transformation of a Metal-Organic Framework from the NbO to PtS Net," Inorg. Chem. 41:181-183 (2005).
Chen et al., "High H2 Adsorption in a Microporous Metal-Organic Framework with Open-Metal Sites," Angew. Chem. Int. Ed. 44:4745-4749 (2005).
Chen et al., "A Microporous Metal-Organic Framework for Gas-Chomatographic Separation of Alkanes," Angew. Chem. Int. Ed. 45:1390-1393 (2006).
Cho et al., "A metal-organic framework material that functions as an enantioselective catalyst for olefin epoxidation," Chem. Comm. 24:2563-2565 (2006).
Choi et al., "Heterogeneity within Order in Crystals of a Porous Metal Organic Framework," J. Am. Chem. Soc. 133:11920-11923 (2011).
Czaja et al., "Industrial applications of metal-organic frameworks," Chemical Society Reviews 38(5):1284-1293 (2009).
Delgado-Friedrichs et al., "Three-Periodic Nets and Tilings: Regular and Quasiregular Nets," Acta Cryst. A59: 22-27 (2003).
Delgado-Friedrichs et al., "Three-Periodic Nets and Tilings: Semiregular Nets," Acta Cryst. A59:515-525 (2003).
Delgado-Friedrichs et al., "The CdSO4, Rutile, Cooperate and Quartz Dual Nets: Interpenetration and Catenation," Solid State Sciences 5:73-78 (2003).
Delgado-Friedrichs et al., "Reticular Chemistry: Occurrence and Taxonomy of Nets, and Grammar for the Design of Frameworks," Acc. Chem. Res. 38:176-182 (2005).
Delgado-Friedrichs et al. "What Do We Know About Three-Periodic Nets?," J. Solid State Chem. 178: 2533-2554 (2005).
Delgado-Friedrichs et al. "Three-Periodic Nets and Tilings: Edge-Transitive Binodal Structures," Acta Cryst. 62:350-355 (2006).
Delgado-Friedrichs et al., "Taxonomy of Periodic Nets and the Design of Materials," Phys. Chem. 9:1035-1043 (2007).
Deng et al., "Multiple Functional Groups of Varying Ratios in Metal-Organic Frameworks," Science 327:846-850 (2010).
Deng et al., "Robust dynamics" Nature Chem. 2:439-443 (2010).
Doonan et al., "Isoreticular Metalation of Metal-Organic Frameworks," J. Am. Chem. Soc. 131:9492-9493 (2009).
Doonan, C., "Hydrogen Storage in Metal-Organic Frameworks," Annual Merit Review Proceedings of DOE Hydrogen Program, May 22, 2009.
Duren et al., "Design of New Materials for Methane Storage," Langmuir 20:2683-2689 (2004).
Eddaoudi et al., "Design and Synthesis of Metal-Organic Frameworks with Permanent Porosity," in Topics in Catalysis, G. A. Somorjai and J. M. Thomas, Eds., 9:105 (1999).
Eddaoudi et al., "Highly Porous and Stable Metal-Organic Framework: Structure Design and Sorption Properties," J. Am. Chem. Soc. 121:1391-1397 (2000).
Eddaoudi et al., "Porous Metal-Organic Polyhedra: 25 Å Cuboctahedron Constructed from Twelve Cu2(CO2)4 Paddle-Wheel Building Blocks," J. Am. Chem. Soc. 123:4368-4369 (2001).
Eddaoudi et al., "Modular Chemistry: Secondary Building Units as a Basis for the Design of Highly Porous and Robust Metal-Organic Carboxylate Frameworks" Acc. Chem. Res. 34:319-330 (2001).
Eddaoudi et al., "Geometric Requirements and Examples of Important Structures in the Assembly of Square Building Blocks," Proc. Natl. Acad. Sci. 99:4900-4904 (2002).

(56) References Cited

OTHER PUBLICATIONS

Eddaoudi et al., "Systematic Design of Pore Size and Functionality in Isoreticular Metal-Organic Frameworks and Application in Methane Storage," Science 295:469-472 (2002): Featured in (1) Chemical and Engineering News, Jan. 21, 2002, and (2) Chemical Insight magazine, Nov. 15, 2002.
Eddaoudi et al., "Cu2[o-Br-C6H3(CO2)2]2(H2O)2•(DMF)8(H2O)2: A Framework Deliberately Designed to have the NbO Structure Type," J. Am. Chem. Soc.124:376-377 (2002).
Ferragut et al., "Positronium Formation in Porous Materials for Antihydrogen Production,"J. Phys. Conf. Ser. 225:1-8 (2010).
Furukawa et al., "Crystal Structure, Dissolution, and Deposition of a 5 nm Functionalized Metal-Organic Great Rhombicuboctahedron," J. Am. Chem. Soc. 128:8398-8399 (2006).
Furkawa et al., "Independent verification of the saturation hydrogen uptake in MOF-177 and establishment of a benchmark for hydrogen adsorption in metal-organic frameworks," J. Mater. Chem. 17:3197-3204 (2007).
Furukawa et al., "Control of Vertex Geometry, Structure Dimensionality, Functionality, and Pore Metrics in the Reticular Synthesis of Crystalline Metal-Organic Frameworks and Polyhedra," J. Am. Chem. Soc.130:11650-11661 (2008).
Furukawa et al., "Ultra-High Porosity in Metal-Organic Frameworks," Science 239:424-428 (2010).
Glover et al., "MOF-74 building unit has a direct impact on toxic gas adsorption," J. Chem. Eng. Sci. 66:163-170 (2011).
Gould et al., "The Amphidynamic Character of Crystalline MOF-5: Rotational Dynamics in a Free-Volume Environment," J. Am. Chem. Soc. 130:3246-3247 (2008).
Goebel, Matthias, Supplemental European Search Report and Written Opinion for EP08826913. Date of Completion of Search and Written Opinion: Nov. 10, 2010.
Goebel, Matthias, Supplemental European Search Report and Written Opinion for EP08754337. Date of Completion of Search and Written Opinion: Dec. 3, 2010.
Grzesiak et al., "Polymer-Induced Heteronucleation for the Discovery of New Extended Solids," Angew. Chem. Int. Ed. 45:2553-2556 (2006).
Halper et al., "Topological Control in Heterometallic Metal-Organic Frameworks by Anion Templating and Metalloligand Design," J. Am. Chem. Soc. 128:15255-15268 (2006).
Han, Ss et al., "Improved designs of metal-organic frameworks for hydrogen storage" Angew. Chem. Int. Ed. 2007, 46, pp. 6289-6292.
Hayashi et al., "Zeolite A Imidazolate Frameworks," Nature Materials 6:501-506 (2007).
Hexiang et al., "Multiple Functional Groups of Varying Rations in Metal-Organic Frameworks," Science 327 (5967):846-850 (2010).
Honda, Masashi, International Preliminary Report on Patentability for PCT/US2008/051859. Date of Issuance of the Report: Jul. 28, 2009.
Howe, Patrick. International Search Report and Written Opinion for PCT/US2009/068849. Date of Mailing of the Search Report: Apr. 6, 201.
Howe, Patrick. International Search Report and Written Opinion for PCT/US2010/022777. Date of Mailing: Jun. 7, 2010.
Huang et al., "Thermal Conductivity of Metal-Organic Framework 5 (MOF-5): Part II. Measurement," Int. J. Heat Mass Transfer 50:405-411 (2007).
Isaeva et al., "Metal-organic frameworks-new materials for hydrogen storage," Russian Journal of General Chemistry 77(4):721-739(2007).
Jeong et al., "Asymmetric Catalytic Reactions by NbO-Type Chiral Metal-Organic Frameworks," Chem. Sci. 2:877-882 (2011).
Kaye et al., "Impact of Preparation and Handling on the Hydrogen Storage Properties of Zn4O(1,4-benzenedicarboxylate)3 (MOF-5)," J. Am. Chem. Soc. 129:14176-14177 (2007).
Kim et al., "Assembly of Metal-Organic Frameworks From Large Organic and Inorganic Secondary Building Units: New Examples and Simplifying Principles for Complex Structures," J. Am. Chem. Soc. 123:8239-8247 (2001).
Kim, Su Mi, International Search Report and Written Opinion, Date of Mailing: Feb. 24, 2010, International Application Number: PCT/US09/46463.
Kim, Su Mi, International Search Report and Written Opinion for PCT/US2009/068731. Date of Mailing: Aug. 19, 2010.
Kim, Su Mi. International Search Report for PCT/US2010/039154. Date of Mailing: Feb. 23, 2011.
Klaes, Daphne. International Search Report and Written Opinion for PCT/US2010/021201. Date of Mailing: Apr. 27, 2010.
Kyoungmoo et al., "A Crystalline Mesoporous Coordination Copolymer with High Microporosity," Angew. Chem. Int. Ed. 47(4):677-680 (2008).
Lee, Ji Min. International Search Report for PCT/US2010/039284. Date of Mailing: Feb. 22, 2011.
Li et al., "Coordinatively Unsaturated Metal Centers in the Extended Porous Framewokr of Zn3(BDC)3-6CH3OH (BDC=1,4-Benzenedicarboxylate)," J. Am. Chem. Soc. 2186-2187 (1998).
Li et al., "Establishing Microporosity in Open Metal-Organic Frameworks: Gas Sorption Isotherms for Zn(BDC) (BDC=1,4-Benzenedicaroxylate)," J. Am. Chem. Soc. 120:8571-8572 (1998).
Li et al., "Porous Germanates: Synthesis, Structure and Inclusion Properties of Ge7O14.5F2-[(CH3)2NH2]3(H2O) O.86," J. Am. Chem. Soc. 120:8567-8568 (1998).
Li et al., "Transformation of Germanium Dioxide to 4-Connected Porous Germanate Net," J. Am. Chem. Soc. 10569-10570 (1998).
Li et al., "An Open-Framework Germanate with Polycubane-Like Topology," Angew. Chem. INt. Ed., 38:653-655 (1999).
Li et al., "Supertetrahedral Sulfide Crystals with Giant Cavities and Channels," Science 283:1145-1147 (1999).
Li et al., "Non-interpenetrating Indium Sulfide with a Supertetrahedral Cristobalite Famework," J. Am. Chem. Soc. 121:6096-6097 (1999).
Li et al., "Design and Synthesis of an Exceptionally Stable and Highly Porous Metal-Organic Framework," 402:276-279 (1999); Featured in (1) Chemical and Engineering News (Nov. 22, 19999) and (2) Science News (Nov. 20, 1999).
Li et al., "Ge2ZrO6F2 (H2DAB)H2O: A 4-Connected Microporous Material with "Bow Tie" Building Units and an Exceptional Proportion of 3-Rings," J. Am. Chem. Soc. 122:12409-12410 (2000).
Li et al., "20 A [Cd4ln16S35]14-Supertetrahedral T4 Clusters as Building Units in Decorated Cristobalite Frameworks," J. Am. Chem Soc. 123:4867-4868 (2001).
Li et al., "[Cd16In64S134]44-: 31-Å Tetrahedron with a Large Cavity," Angew. Chem. Int. Ed., 42:1819-1821 (2003).
Li et al., "A metal-organic framework replete with ordered donor-acceptor catenanes," Chem. Commun. 46:380-382 (2010).
Li et al., "A Catenated Strut in a Catenated Metal-Organic Framework," Angew. Chem. Int. Ed. 49:6751-6755 (2010).
Linder, Nora. International Preliminary Report on Patentability for PCT/US2010/022777. Date of Mailing: Aug. 11, 2011.
Llabres et al., "MOFs as catalysts: Activity, reusability and shape-selectivity of a Pd-containing MOF," JOurnal of Catalysis 250(2):294-298.
Long et al., "The Pervasive Chemistry of Metal-Organic Frameworks," Chem. Soc. Rev. 38:1213-1214 (2009).
Lu et al., "Synthesis and Structure of Chemically Stable Metal-Organic Polyhedra," J. Am. Chem. Soc. 131:(35) 12532-12533 (2009).
Michalitsch, Richard. International Search Report and Written Opinion for PCT/US2009/069700. Date of Mailing: May 7, 2010.
Millward et al., "Metal-Organic Frameworks with Exceptionally High Capacity for Storage of Carbon Dioxide at Room Temperature," J. Am. Chem. Soc. 127:17998-17999 (2005).
Morris et al., "Crystals as Molecules: Postsynthesis Covalent Functionalization of Zeolitic Imidazolate Frameworks," J. Am. Chem. Soc. 130:12626-12627 (2008).
Morris et al., "A Combined Experimental-Computational Investigation of Carbon Dioxide Capture in a Series of Isoreticular Zeolitic Imidazolate Frameworks," J. Am. Chem. Soc. 132:11006-11008 (2010).
Morris et al., "Postsynthetic Modification of a Metal-Organic Framework for Stabilization of a Hemiaminal and Ammonia Uptake," Inorg. Chem. 50:6853-6855 (2011).

(56) References Cited

OTHER PUBLICATIONS

Moyse, Ellen, International Preliminary Report on Patentability and Written Opinion, Date of Issuance of Report: Nov. 17, 2009, International Application No: PCT/US08/006008.
Mulhausen, Dorothee. International Preliminary Report on Patentability for PCT/US2009/069700. Date of Mailing: Jul. 7, 2011.
Mulhausen, Dorothee. International Preliminary Report on Patentability for PCT/US2010/021201. Date of Mailing Jul. 28, 2011.
Natarajan et al., "Non-carboxylate based metal-organic frameworks (MOFs) and related aspects," Current Opinion in Solid State and Materials Science 13(3-4):46-53 (2009).
Ni et al,. "Porous Metal-Organic Truncated Octahedron Constructed from Paddle-Wheel Squares and Terthiophene Links," J. Am. Chem. Soc. 127:12752-12753 (2005).
Wang et al., "Colossal Cages in Zeolitic Imidazolate Frameworks as Selective Carbon Dioxide Reservoirs," Nature 453:207-211 (2008).
Wang et al., "Tandem Modification of Metal-Organic Frameworks by a Postsynthetic Approach," Angew. Chem. Int. 47:4699-4702 (2008).
Wong-Foy, Ag et al., "Exceptional H2 saturation uptake in microporous metal-organic frameworks" J. Am. Chem. Soc., 2006, 128, pp. 3494-3495.
Yaghi et al., "Selective binding and removal of guests in a microporous metal-organic framework," Nature, Dec. 1995, pp. 703-706, vol. 378.
Yaghi et al., "Conversion of Hydrogen-Bonded manganese(II) and zinc(II) squarate (C4O42-) molecules, Chains, and Sheets to 3-D Cage Networks," J. Chem. Soc., Dalton Trans., 1995, 727-732.
Yaghi et al., "Presence of Mutually Interpenetrating Sheets and Channels in the Extended Structure of Cu(4,4'-Bipyridine)Cl," Angew. Chem. Int. Ed. Engl., 1995, 34, 207-209.
Yaghi et al., "The Utility of Polymeric Matrices in the Preparation of Single Crystals of Coordination Solids: Synthesis and Structure of CuII(1,4-C4H4N2)(C4O4)(OH2)4," J. Solid State Chem., 1995, 117, 256-260.
Yaghi et al., "Open-Framework Solids with Diamond-Like Structures Prepared from Clusters and Metal-Organic Building Blocks,"Mater. Res. Soc. Symp. Proc., 1995, 371, 15.
Yaghi et al., "Hydrothermal Synthesis of a Metal-Organic Framework Containing Large Rectangular Channels," J. Am. Chem. Soc., 1995, 117, 10401-10402.
Yaghi et al., "Construction of Microporous Materials from Molecular Building Blocks," Fundamental Materials Research, T. J. Pinnavaia and M. F. Thorpe, eds., vol. II, Plenum: New York, p. 111 (1995).
Yaghi et al., "T-Shaped Molecular Building Units in the Porous Structure of Ag(4,4'-bpy) NO3," J. Am. Chem. Soc., 1996, 118, 295-296.
Yaghi et al., "Construction of Porous Solids from Hydrogen-Bonded Metal Complexes of 1,3,5-Benzenetricarboxylic Acid," J. Am. Chem. Soc., 1996, 118, 9096-9101.
Yaghi et al., "Conversion of Molecules and Clusters to Extended 3-D Cage and Channel Networks," Metal Containing Polymeric Materials, C. U. Pittman, C. E. Carraher, B. M. Culbertson, M. Zeldin, J. E. Sheets, Eds., Plenum: New York, p. 219 (1996).
Yaghi et al., "Selective Guest Binding by Tailored Channels in a 3-D Porous Zinc(II)-1,3,5-Benzenetricarboxylate Network," J. Am. Chem. Soc., 1997, 119, 2861-2868.
Yaghi et al., "Crystal Growth of Extended Solids by Nonaqueous Gel Diffusion," Chem. Mater., 1997, 9, 1074-1076.
Yaghi et al., "A Molecular Railroad with Large Pores: Synthesis and Structure of Ni(4,4'-bpy)2.5(H2O)2(ClO4)2•1.5(4,4'-bpy)2(H2O)," Inorg. Chem., 1997, 36, 4292-4293.
Yaghi et al., "Construction of a New Open-Framework Solid form 1,3,5-Cyclohexanetricarboxylate and Zinc(II) Building Blocks," J. Chem. Soc. Dalton Trans. 2383-2384 (1997).
Yaghi et al., "Synthesis and Structure of a Metal-Organic Solid Having the Cadmium (II) Sulfate Net," Mater. Res. Soc. Symp. Proc. 453:127 , (1997).
Yaghi et al., "Designing Microporosity in Coordination Solids," Modular Chemistry, J. Michl, Ed., Kluwer: Boston, p. 663 (1997).

Yaghi et al., "Synthetic Strategies, Structure Patterns, and Emerging Properties in the Chemistry of Modular Porous Solids," Acc. Chem. Res. 31:474-484 (1998).
Yaghi et al., "Transformation of Germanium Dioxide to 4-Connected Porous Germanate Net," J. Am. Chem. Soc., 20:10569-10570 (1998).
Yaghi et al., "Design of Solids from Molecular Building Blocks: Golden Opportunities for Solid State Chemistry," J. Solid State Chem. 152, 1-2 (2000).
Yaghi et al., "A Molecular World Full of Holes," Chem. Innov. p. 3 (2000).
Yaghi et al., "Reticular Synthesis and the Design of New Materials," Nature 423:705-714 (2003).
Yaghi, Omar., "Porous Crystals for Carbon Dioxide Storage," slide presentation at the Fifth Annual Conference on Carbon Capture & Sequestration, US Department of Energy on May 10, 2006 http://www.netl.doe.gov/publications/proceedings/06/carbon-seq/Tech%20Session%20193.pdf.
Yaghi, Omar, "Hydrogen Storage in Metal-Organic Frameworks," slide presentation to DOE Hydrogen Program 2007 Annual Merit Review, US Department of Energy, on May 15, 2007 at http://www.hydrogen.energy.gov/pdfs/review07/st_10_yaghi.pdf.
Yaghi et al., "Metal-Organic Frameworks: A Tale of Two Entanglements," Nature materials 6:92-93 (2007).
Yaghi et al., "Reticular Chemistry and Metal-Organic Frameworks for Clean Energy," MRS Bulletin 34:682-690 (2009).
Young, Lee W., International Search Report and Written Opinion, Date of Mailing of Report: May 7, 2008, International Application No: PCT/US08/51859.
Young, Lee W., "International search Report and Written Opinion," PCT/US08/06008, United States Patent & Trademark Office, Aug. 20, 2008.
Young, Lee W., International Search Report and Written Opinion, Date of Mailing: Dec. 2, 2008, International Application Number: PCT/US08/77741.
Young, Lee W., International Search Report and Written Opinion, Date of Mailing: Jan. 12, 2009, International Application Number: PCT/US08/70149.
Young, Jung Doo. International Search Report for PCT/US2010/050170. Date of Mailing: Jun. 8, 2011.
Zhang et al., "Docking in Metal-Organic Frameworks," Science 325:855-859 (2009).
Zhao et al., "Rigid-Strut-Containing Crown Ethers and [2]Catenanes for Incorporation into Metal-Organic Frameworks," Chem. Eur. J. 15:13356-13380 (2009).
Zhofu et al., "A Nearly Planar Water Sheet Sandwiched between Strontium-Imidazolium Carboxylate Coordination Polymers," Inorg. Chem. 44:5200-5202 (2005).
McKeown et al., "Phthalocyanine-based Nanoporous network Polymers," Chem. Commun. pp. 2780-2781 (2002).
McKeown et al., "Porphyrin-based Nanoporous Network Polymers," Chem. Commun., pp. 2782-2783 (2002).
Sptiler et al., "Lewis Acid Catalysed Formation of Two-Dimensional Phthalocyanine Covalent Organic Frameworks," Nature Chem. 2:672-677 (2010).
Wan et al., "A Belt-shaped, Blue Luminescent, and Semiconducting Covalent Organic Framework," Agnew. Chem. Int. Ed., 47:8826-8830 (2008).
Wan et al., "Covalent Organic Frameworks with High Charge Carrier Mobility," Chem. Mater., 23:4094-4097 (2011).
Young, Jung Doo, Written Opinion, PCT/US2011/053423, Korean Intellectual Property Office, Jul. 20, 2012.
Lindner, Nora, International Preliminary Report on Patentability, PCT/US2011/053423, The International Bureau of WIPO, Apr. 2, 2013.
Nickitas-Etienne, Athina, International Preliminary Report on Patentability and Written Opinion, Date of Issuance of Report: Jan. 19, 2010, International Application No. PCT/US08/70149.
Nickitas-Etienne, Athina. International Preliminary Report on Patentability for PCT/US2008/07741. Date of issuance of this report: Mar. 30, 2010.
Nickitas-Etienne, Athina, International Preliminary Report on Patentability for PCT/US2009/068731. Date of Issuance of the Report: Jun. 21, 2011.

(56) References Cited

OTHER PUBLICATIONS

Nickitas-Etienne, Athina. International Preliminary Report on Patentability for PCT/US2009/068849. Date of Mailing: Jun. 30, 2011.
Oisaki et al., "A Metal-Organic Framework with Covalently Bound Organometallic Complexes," J. Am. Chem. Soc. 132:9262-9264 (2010).
O'Keefe et al., "Germanate Zeolites: Contrasting the Behavior of Germanate and Silicate Structures Built from Cubic T8O20 units (T=Si or Ge)," Chem. Eur. J. 5:2796-2801 (1999).
O'Keefe et al., "Frameworks for Extended Solids: Geometrical Design Principles," J. Solid State Chem. 152:3-20 (2000).
Okeeffe et al., "Reticular Chemistry—Present and Future Prospects—Introduction,"J. Solid State Chem.178:V-VI (2005).
O'Keeffe et al., "The Reticular Chemistry Structure Resource (RCSR) Database of, and Symbols for, Crystal Nets," Acc. Chem. Res. 41:1782-1789 (2008).
Park, Kyo Sung et al., "Exceptional chemical and thermal stability of zeolitic imidazolate frameworks," Proc. Natl. Acad. Sci., Jul. 5, 2006, pp. 10186-10191, vol. 103, No. 27.
Park, Jae Woo. International Search Report for PCT/US2010/039123. Date of Mailing: Feb. 24, 2011.
Patteux, Claudine. International Search Report for PCT/US2010/043373. Date of Mailing: Oct. 10, 2010.
Pawsey et al., "Hyperpolarized 129Xe Nuclear Magnetic Resonance Studies of Isoreticular Metal-Organic Frameworks," Phys. Chem. 111:6060-6067 (2007).
Phan et al., "Synthesis, Structure, and Carbon Dioxide Capture Properties of Zeolitic Imidazolate Frameworks," Acc. Chem. Res 43:58-67 (2009).
Phan et al., "Metal-Organic Frameworks of Vanadium as Catalysts for Conversion of Methane to Acetic Acid," Inorg. Chem. 50:7388-7390 (2011).
Plevert et al., "A Flexible Germanate Structure Containing 24-Ring Channels With Very Low Framework Density," J. Am. Chem. Soc. 123:12706-12707 (2001).
Plevert et al., "Synthesis and Characterization of Zirconogermanates," Inorg. Chem., 42:5954-5959 (2003).
Plevert et al., "Layered Structures Constructed from New Linkages of Ge7(O,OH,F)19 Clusters," Chem. Mater. 15:714-718 (2003).
Reineke et al., "From Condensed Lanthanide Coordination Solids to Microporous Frameworks Having Accessible Metal Sites," J. Am. Chem. Soc 121:1651-1657 (1999).
Reineke et al., "A Microporosity of Lanthanide-Organic Frameworks," Angew. Chem. Int. Ed. 38:2590-2594 (1999).
Reineke et al., "Large Free Volume in Interpenetrating Networks: The Role of Secondary Building Units Exemplified by Tb2(ADB)3[(CH3)2SO]4-16[(CH3)2SO]," J. Am. Chem. Soc. 122:4843-4844 (2000); Featured in Science Magazine, Editors Choice (Nov. 2000).
Rosi et al., "Infinite Secondary Building Units and Forbidden Catenation in Metal-Organic Frameworks," Angew. Chem. Int. Ed. 41:294-297 (2002).
Rosi et al., "Advances in the Chemistry of Metal-Organic Frameworks," CrystEngComm 4:401-404 (2002).
Rosi et al., "Hydrogen Storage in Microporous Metal-Organic Frameworks," Science 300:1127-1129 (2003); Featured in (1) Chemical & Engineering News magazine, May 19, 2004, and (2) Technology Research News Magazine, May 21, 2003.
Rosi et al., "Rod-Packings and Metal-Organic Frameworks Constructed from Rod-Shaped Secondary Building Units," J. Am. Chem. Soc. 127:1504-1518 (2005).
Rowsell et al., "Hydrogen Sorption in Functionalized Metal-Organic Frameworks," J. Am. Chem. Soc.126: 5666-5667 (2004).
Rowsell et al., "Metal-Organic Frameworks: A New Class of Porous Materials," Microporous Mesoporous Mater. 73:3-14 (2004).
Rowsell et al., "Strategies for Hydrogen Storage in Metal-Organic Frameworks," Angew. Chem. Int. Ed. 44: 4670-4679 (2005).
Rowsell et al., "Gas Adsorption Sites in a Large-Pore Metal-Organic Framework," Science 309:1350-1354 (2005).
Rowsell et al., "Characterization of H2 Binding sites in prototypical metal-organic frameworks by inelastic neutron scattering," J. Am. Chem. Soc. 127:14904-14910 (2005).
Rowsell et al., "Effects of Functionalization, Catenation, and Variation of the Metal Oxide and Organic Linking Units on the Low-Pressure Hydrogen Adsorption Properties of Metal-Organic Frameworks," J. Am. Chem. Soc. 128: 1304-1315 (2006).
Siberio-Perez, "Raman Spectroscopic Investigation of CH4 and N2 Adsorption in Metal-Organic Frameworks," Chem. Mater. 19:3681-3685 (2007).
Smaldone et al., "Metal-Organic Frameworks from Edible Nature Products," Angew. Chem. Int. Ed. 49:8630-8634 (2010).
Spencer et al., "Determination of the Hydrogen Absorption Sites in Zn4O(1,4-benzenedicarboxylate) by Single Crystal Neutron Diffraction," Chem. Commun. 3:278-280 (2006); Epub Dec. 6, 2005.
Stallmach et al., "NMR Studies on the Diffusion of Hydrocarbons on the Metal-Organic Framework Material MOF-5," Angew. Chem. Int. Ed. 45:2123-2126 (2006).
Sudik et al., "Design, Synthesis, Structure, and Gas (N2, Ar, CO2, CH4 and H2) Sorption Properties of Porous Metal-Organic Tetrahedral and Heterocuboidal Polyhedra," J. Am. Chem. Soc. 127:7110-7118 (2005).
Sudik et al., "Metal-Organic Frameworks Based on Trigonal Prismatic Building Blocks and the New "acs" Topology," Inorg. Chem. 44:2998-3000 (2005).
Sudik et al., "A Metal-Organic Framework with a Hierarchical System of Pores and Tetrahedral Bbuilding Blocks," Angew. Chem. Int. Ed. 45:2528-2533 (2006).
Tranchemontagne et al. "Metal-Organic Frameworks with High Capacity and Selectivity for Harmful Gases," Proc. Natl. Acad. Sci. USA 105:11623-11627 (2008).
Tranchemontagne et al., "Reticular Chemistry of Metal-Organic Polyhedra," Angew. Chem. Int. Ed., 2008, 47:5136-5147 (2008).
Tranchemontagne et al., "Room Temperature Synthesis of Metal-organic Frameworks: MOF-5, MOF-74, MOF-177, MOF-199, and IRM0F-0," Tetrahedron 64:8553-8557 (2008).
Tranchemontagne et al. "Secondary Building Units, Nets and Bonding in the Chemistry of Metal-Organic Frameworks," Chem. Soc. Rev. 38:1257-1283 (2009).
Uribe-Romo et al., "A Crystalline Imine-Linked 3-D Porous Covalent Organic Framework," J. Am. Chem. Soc. 131:4570-4571 (2009).
Uribe-Romo et al., "Crystalline Covalent Organic Frameworks with Hydrazone Linkages," J. Am. Chem. Soc. 133: 11478-11481 (2011).
Vairaprakash et al., "Synthesis of Metal-Organic Complex Arrays," J. Am. Chem. Soc. 133:759-761 (2011).
Valente et al., "Metal-organic Frameworks with Designed Chiral Recognition Sites," Chem. Commun. 46: 4911-4913 (2010).
Vodak et al., "Metal-Organic Frameworks Constructed from Pentagonal Antiprismatic and Cuboctahedral Secondary Building Units," Chem. Commun. 2534-2535 (2001).
Vodak et al., " Computation of Aromatic C3N4 Networks and Synthesis of the Molecular Precursor N(C3N3)3C16," Chem. Eur. J. 9:4197-4201 (2003).
Walton et al., "Understanding Inflections and Steps in Carbon Dioxide Adsorption Isotherms in Metal-Organic Frameworks," J. Am. Chem. Soc.130:406-407 (2008).
Wang et al., "Postsynthetic Covalent Modification of a Neutral Metal-Organic Framework," J. Am. Chem. Soc. 129 (41):12368-12369 (2007).
Richter, Herbert, Supplementary European Search Report, European Patent Application No. 11848340.3, European Patent Office, Feb. 6, 2014.
Xiaowei Qiu, First Office Action issued in Chinese Patent Application No. 201180056905.5, Issue Date: Jul. 18, 2014.
Qiu, Xiaowei, Chinese Application No. 201180056905.5, Date of Mailing: Feb. 3, 2015.

\* cited by examiner

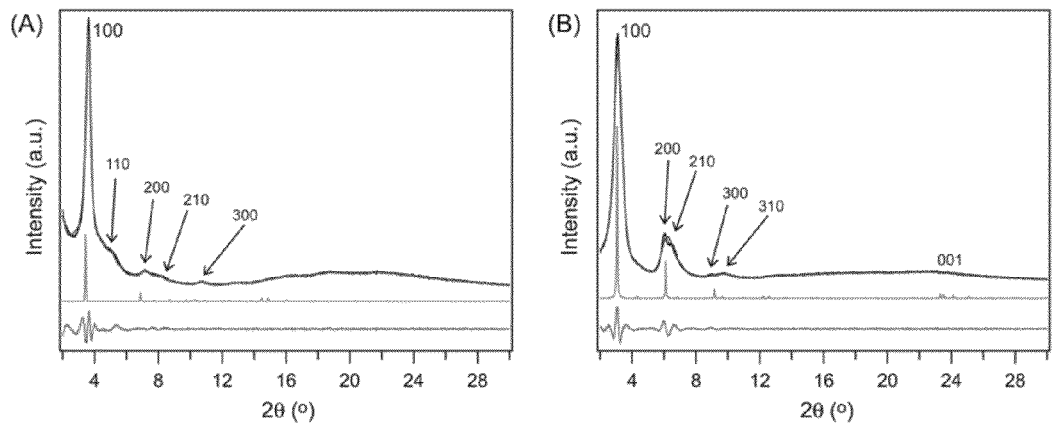
Figure 1A-B
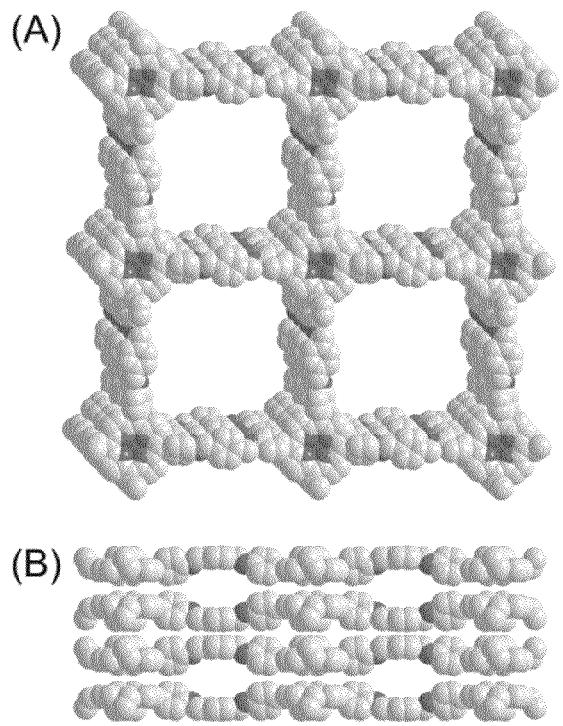
Figure 2A-B

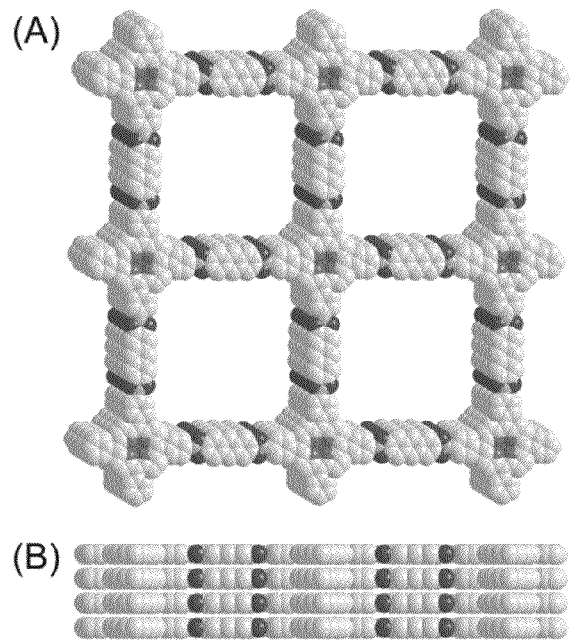
Figure 3A-B
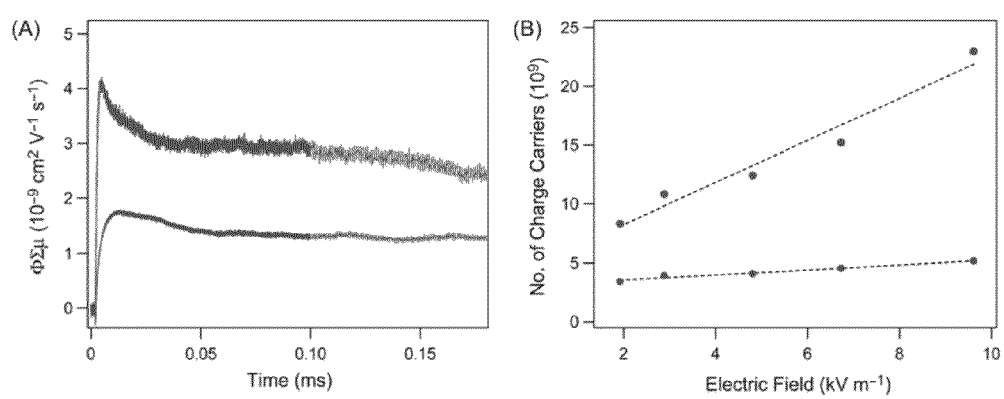
Figure 4A-B (A)
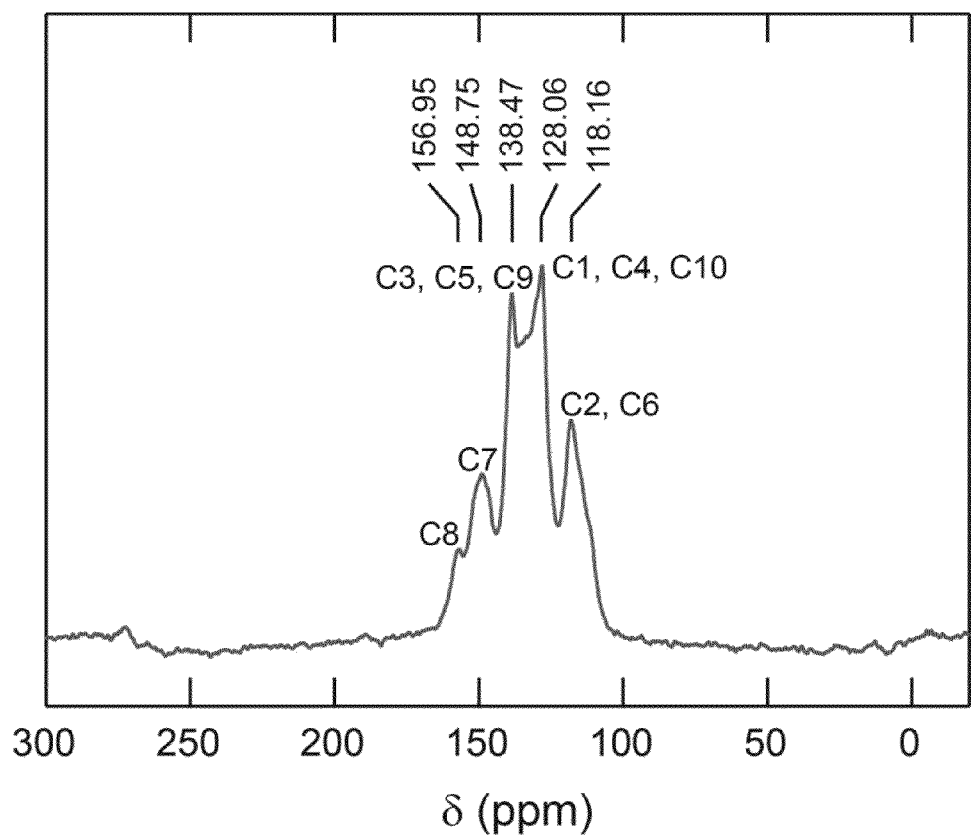
(B)
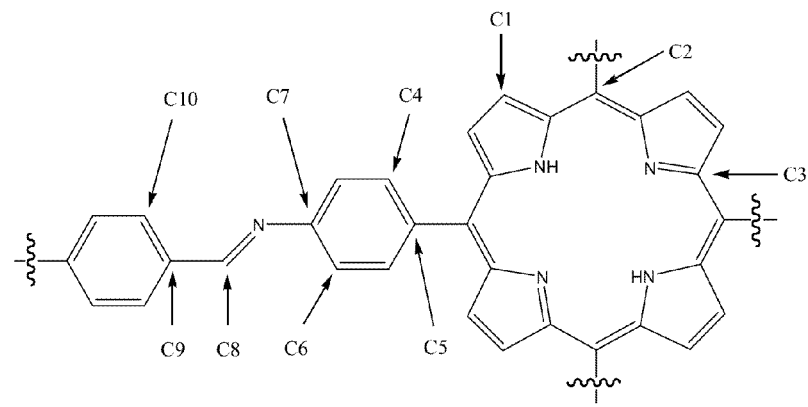
Figure 8A-B (A)
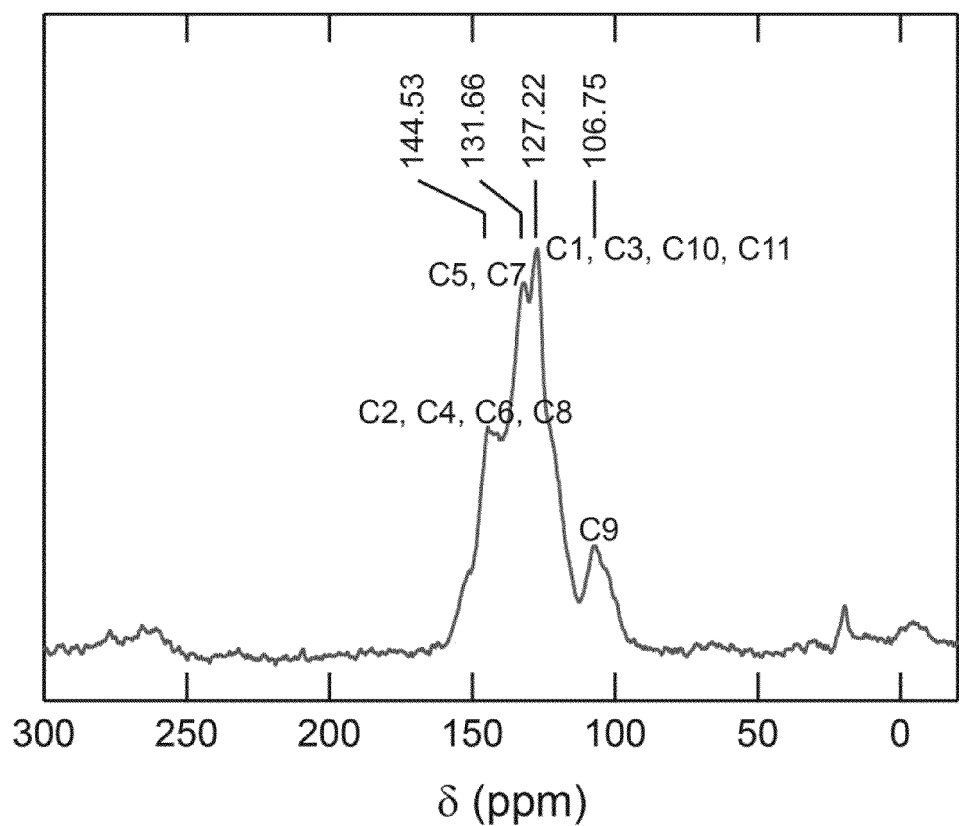
(B)
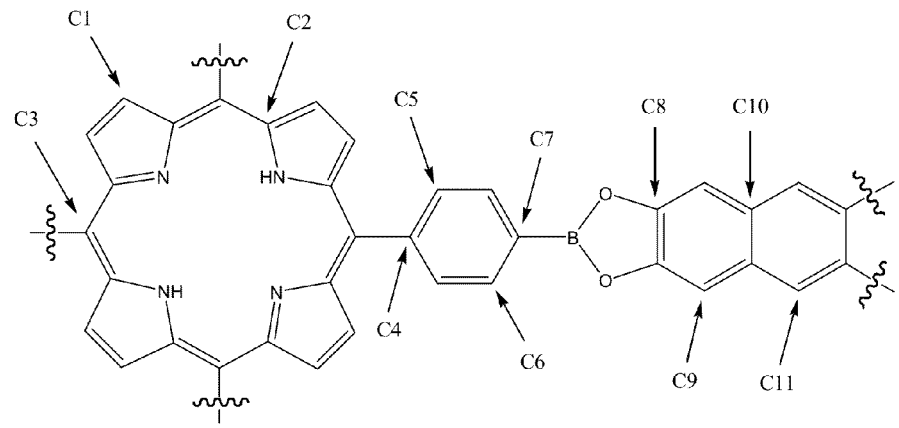
Figure 10A-B

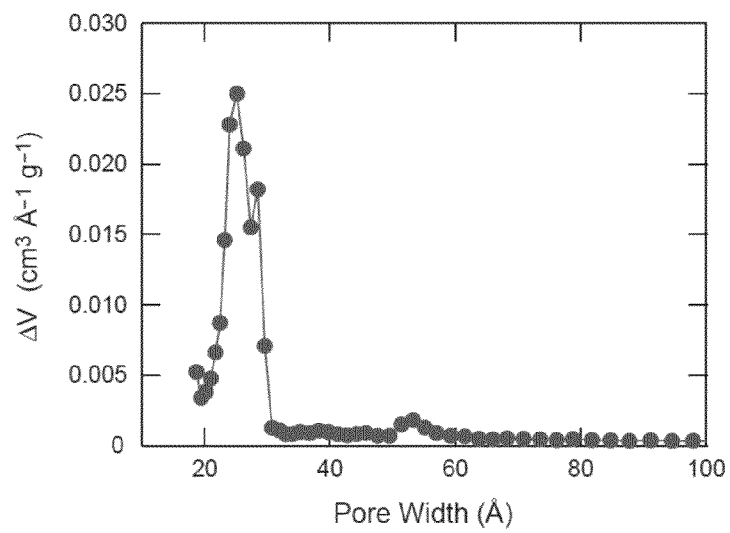
Figure 23
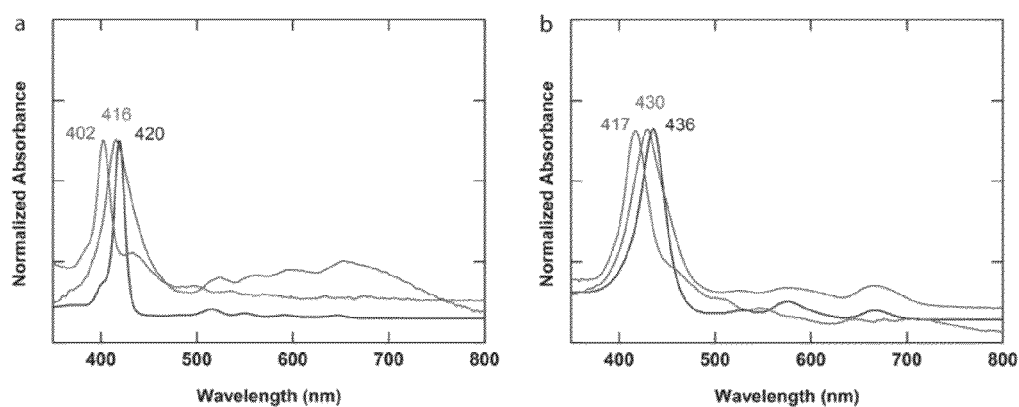
Figure 24a-b

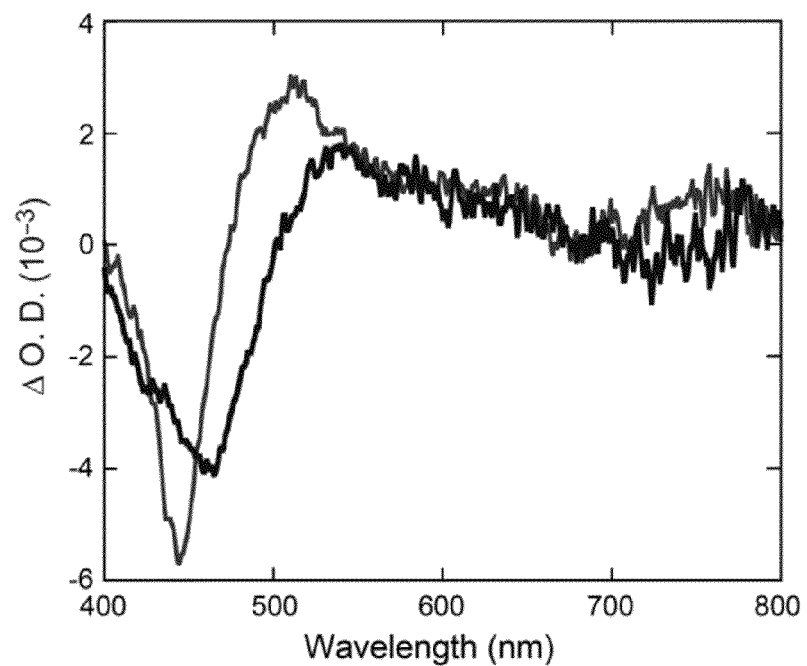
Figure 28
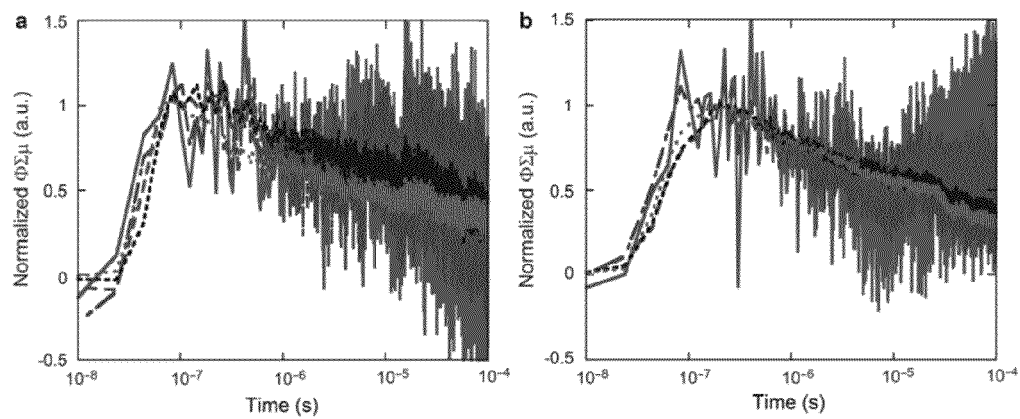
Figure 29a-b

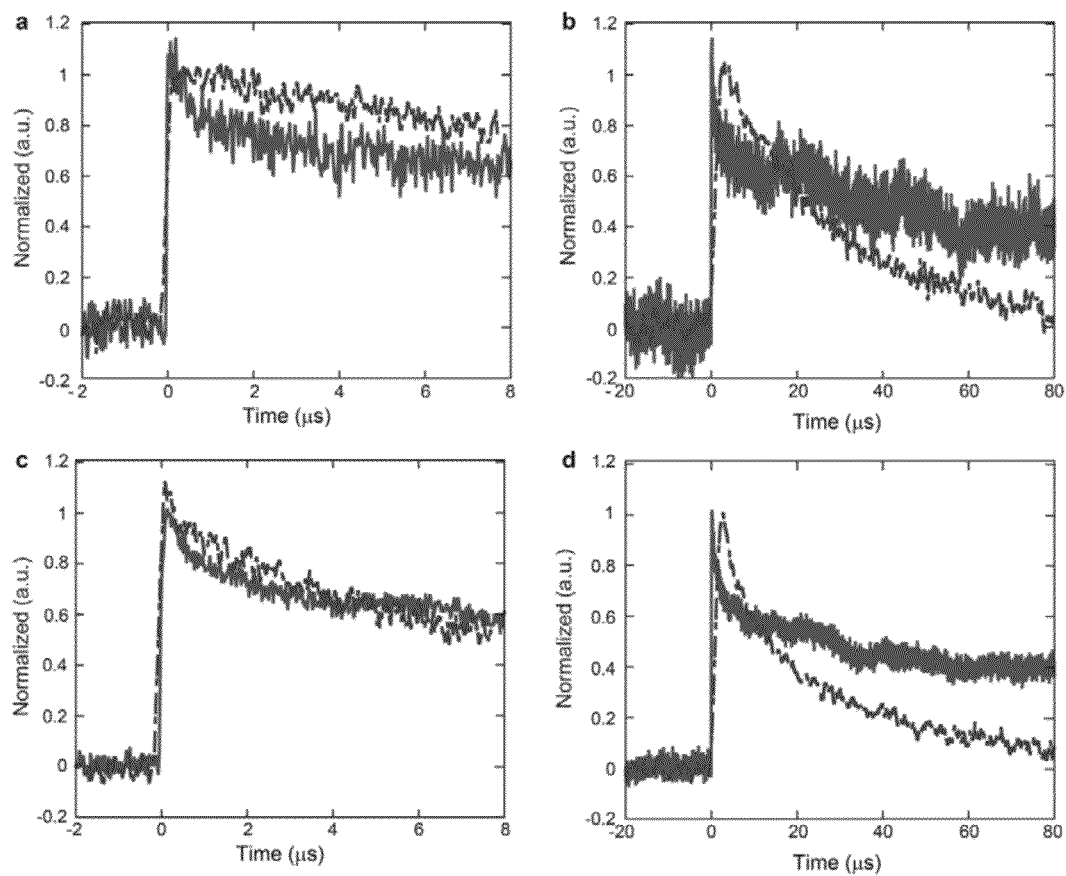
Figure 30a-d

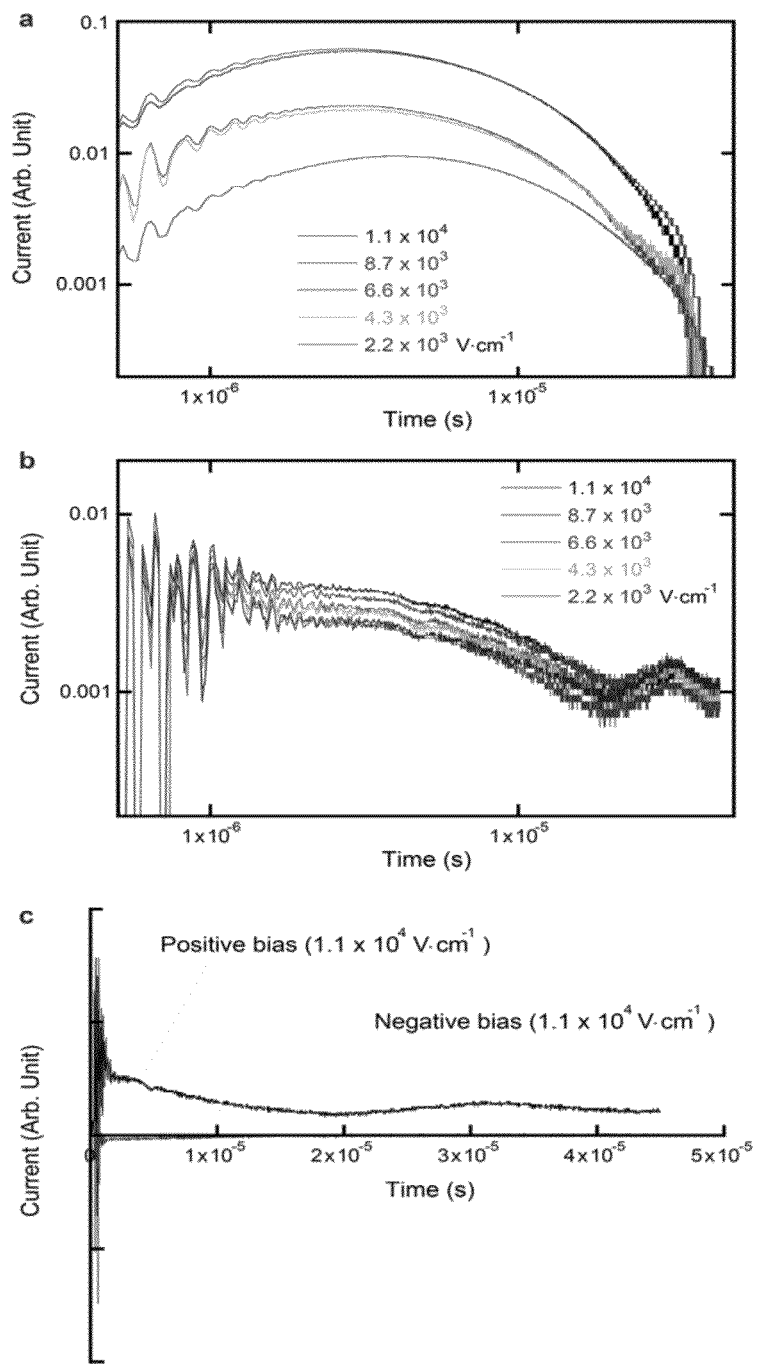
Figure 31a-c

CONDUCTIVE OPEN FRAMEWORKS

CROSS-REFERENCE TO RELATED APPLICATIONS

This application is a U.S. National Stage Application filed under 35 U.S.C. 371 and claims priority to International Application No. PCT/US2011/053423, filed Sep. 27, 2011, which claims priority to U.S. Provisional Application Ser. No. 61/386,927, filed Sep. 27, 2010, the disclosures of which are incorporated herein by reference.

STATEMENT REGARDING FEDERALLY SPONSORED RESEARCH

This invention was made with Government support under Grant No. HDTRA1-08-1-0023, awarded by the United States Department of Defense, Defense Threat Reduction Agency and Grant No. DE-FG36-05GO15001, awarded by the United States Department of Energy. The Government has certain rights in the invention.

TECHNICAL FIELD

The application relates generally to porous materials that comprise organic frameworks. The application also relates to materials that are useful as conductive materials, to store and separate gas molecules, as well as sensors based upon the frameworks.

BACKGROUND

There has been an increasing demand for porous materials in industrial applications such as gas storage, separations, catalysis and conductive materials. Some of the advantages of organic porous materials over their inorganic or metal-organic counterparts, include: lighter molecular weight, easier to functionalize, and generally have better kinetic stability. Moreover, organic porous materials are more environmentally friendly than comparable frameworks.

Current methods to introduce porosity into polymeric structures are largely based on processing the polymers under certain conditions, or by preparing the polymers from colloidal systems. All glassy polymers contain some void space (free volume), although this is usually less than 5% of the total volume. It is possible to "freeze-in" up to 20% additional free volume for some glassy polymers with rigid structures by rapid cooling from the molten state below the glass transition temperature, or by rapid solvent removal from a swollen glassy polymer. High free volume polymers are currently used in industrial membranes for transporting either gases or liquids. The voids in these materials, however, are not interconnected and therefore reflect a low accessible surface area as determined by gas adsorption. Moreover, the pore structure is irregular and not homogeneous.

Another existing class of porous organic materials includes polyacetylenes containing bulky substituent groups. The high gas permeabilities of poly(1-trimethylsilyl-1-propyne) ("PTMSP") has been observed since 1983. This material contained a large free volume (~30%), and was able to separate organic compounds from gases or water. The stability of PTMSP is limited by its rapid loss of microporosity due to non-uniform pore structure, exposure to heat, oxygen, radiation, or UV light, or any combination of the above.

Recently, polymers of intrinsic microporosity (PIMs) were shown to have exceptional porosity for organic polymers. As measured by gas adsorption, PIMs were reported to contain relatively high surface areas (430-850 m²/g). The porosity of PIMs is likely due to their highly rigid and contorted molecular structures which inhibit efficiently packing in space. PIMs, however, display marked hysteresis at low pressures.

SUMMARY

The disclosure provides electrical or proton conductive open organic covalent frameworks comprised of one or more types of cores and one or more types of linking moieties.

In a certain embodiment, a covalent-organic framework (COF) disclosed herein comprises a plurality of cores, wherein each core forms at least one covalent bond to at least one linking moiety; and where the COF comprises a conductive core moiety and/or comprises a conductive linking moiety.

In a further embodiment, a COF disclosed herein contains one or more cores that are substantially planar and which contain one or more substituted or unsubstituted aryls, substituted or unsubstituted aromatic heterocycles, substituted or unsubstituted alkenes, or combinations thereof.

In yet a further embodiment, a COF disclosed herein contains one or more cores which has a structure selected from the group comprising Formula I, II, III, IV, and V:

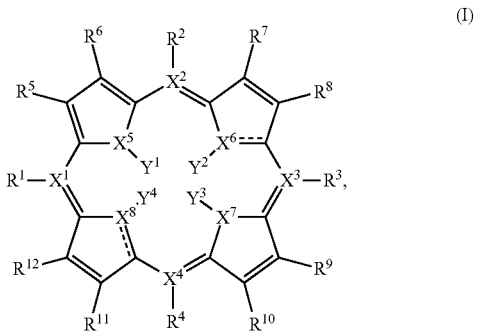

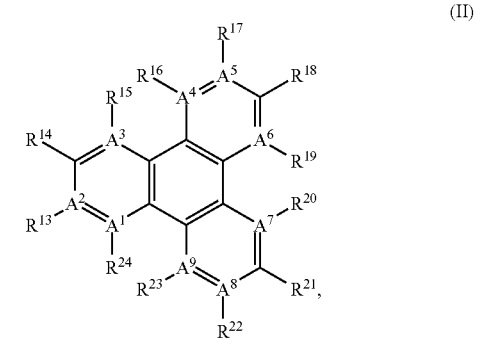

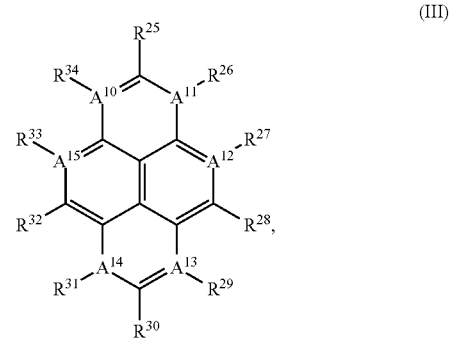

-continued

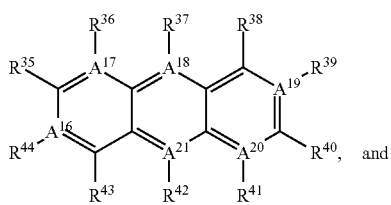
(IV)

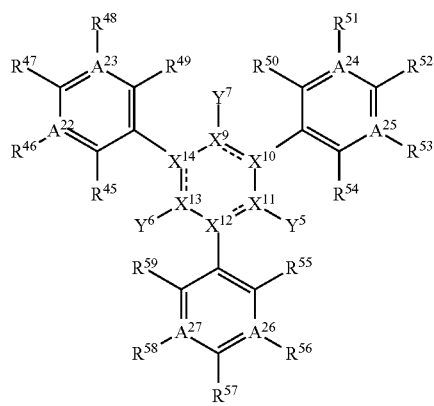
(V)

wherein:

$R^1$-$R^{59}$ are independently selected from the group comprising H, D, FG, ($C_1$-$C_{20}$)alkyl, substituted ($C_1$-$C_{20}$)alkyl, ($C_1$-$C_{20}$)alkenyl, substituted ($C_1$-$C_{20}$)alkenyl, ($C_1$-$C_{20}$)alkynyl, substituted ($C_1$-$C_{20}$)alkynyl, hetero-($C_1$-$C_{20}$)alkyl, substituted hetero-($C_1$-$C_{20}$)alkyl, hetero-($C_1$-$C_{20}$)alkenyl, substituted hetero-($C_1$-$C_{20}$)alkenyl, hetero-($C_1$-$C_{20}$)alkynyl, substituted hetero-($C_1$-$C_{20}$)alkynyl, ($C_1$-$C_{20}$)cycloalkyl, substituted ($C_1$-$C_{20}$)cycloalkyl, aryl, substituted aryl, heterocycle, substituted heterocycle, wherein $R^5$ and $R^6$ are linked together to form a substituted or unsubstituted ring selected from the group comprising cycloalkyl, aryl and heterocycle, wherein $R^7$ and $R^8$ are linked together to form a substituted or unsubstituted ring selected from the group comprising cycloalkyl, aryl and heterocycle, wherein $R^9$ and $R^{10}$ are linked together to form a substituted or unsubstituted ring selected from the group comprising cycloalkyl, aryl and heterocycle, and wherein $R^{11}$ and $R^{12}$ are linked together to form a substituted or unsubstituted ring selected from the group comprising cycloalkyl, aryl and heterocycle;

$X^1$-$X^{13}$ are independently selected from the group comprising carbon, oxygen, sulfur, silicon, phosphorous, and nitrogen;

$Y^1$-$Y^7$ are independently selected from the group comprising H, D, and FG;

$A^1$-$A^{27}$ are independently selected from the group comprising C, N, Si and P;

with the proviso that a X may not exceed its maximum valence by binding a Y, or $R^1$-$R^4$; and with the proviso that a A may not exceed its maximum valence by binding a R.

In a certain embodiment, a COF disclosed herein has one or more cores with a structure of Formula I:

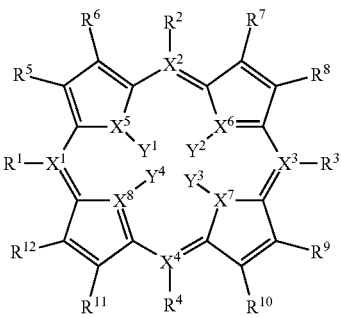
(I)

wherein, $R^1$-$R^{12}$ are independently selected from the group comprising H, D, FG, ($C_1$-$C_6$)alkyl, substituted ($C_1$-$C_6$)alkyl, ($C_1$-$C_6$)alkenyl, substituted ($C_1$-$C_6$)alkenyl, ($C_1$-$C_6$)alkynyl, substituted ($C_1$-$C_6$)alkynyl, hetero-($C_1$-$C_6$)alkyl, substituted hetero-($C_1$-$C_6$)alkyl, hetero-($C_1$-$C_6$)alkenyl, substituted hetero-($C_1$-$C_6$)alkenyl, hetero-($C_1$-$C_6$)alkynyl, substituted hetero-($C_1$-$C_6$)alkynyl, ($C_1$-$C_6$)cycloalkyl, substituted ($C_1$-$C_6$) cycloalkyl, aryl, substituted aryl, heterocycle, substituted heterocycle, wherein $R^5$ and $R^6$ are linked together to form a substituted or unsubstituted ring selected from the group comprising cycloalkyl, aryl and heterocycle, wherein $R^7$ and $R^8$ are linked together to form a substituted or unsubstituted ring selected from the group comprising cycloalkyl, aryl and heterocycle, wherein $R^9$ and $R^{10}$ are linked together to form a substituted or unsubstituted ring selected from the group comprising cycloalkyl, aryl and heterocycle, and wherein $R^{11}$ and $R^{12}$ are linked together to form a substituted or unsubstituted ring selected from the group comprising cycloalkyl, aryl and heterocycle;

$X^1$-$X^8$ are independently selected from the group comprising carbon and nitrogen;

$Y^1$-$Y^4$ are independently selected from the group comprising H, D, and FG; and with the proviso that a X may not exceed its maximum valence by binding a Y, or $R^1$-$R^4$.

In another embodiment, a COF disclosed herein has one or more cores with a structure of Formula Ib:

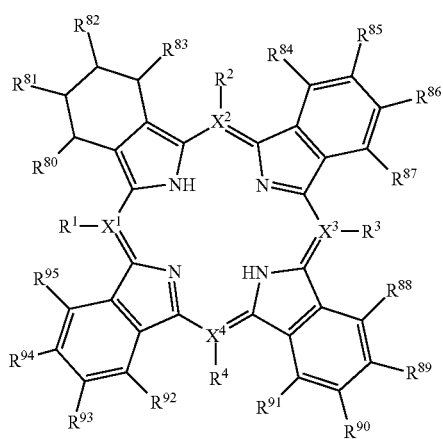
(Ib)

wherein, $R^1$-$R^4$, $R^{80}$-$R^{95}$ are independently selected from the group comprising H, D, FG, ($C_1$-$C_6$)alkyl, substituted ($C_1$-$C_6$)alkyl, ($C_1$-$C_6$)alkenyl, substituted ($C_1$-$C_6$)alkenyl, ($C_1$-$C_6$)alkynyl, substituted ($C_1$-$C_6$)alkynyl, hetero-($C_1$-$C_6$)alkyl, substituted hetero-($C_1$-$C_6$)alkyl, hetero-($C_1$-$C_6$)alkenyl, substituted hetero-($C_1$-$C_6$)alkenyl, hetero-($C_1$-$C_6$)alkynyl, substituted hetero-($C_1$-$C_6$)alkynyl, ($C_1$-$C_6$)cycloalkyl, substituted ($C_1$-$C_6$)cycloalkyl, aryl, substituted aryl, heterocycle, and substituted heterocycle;

$X^1$-$X^4$ are independently selected from the group comprising carbon and nitrogen; and with the proviso that a X may not exceed its maximum valence by binding a R.

In a further embodiment, a COF disclosed herein has one or more cores with a structure of Formula Ia:

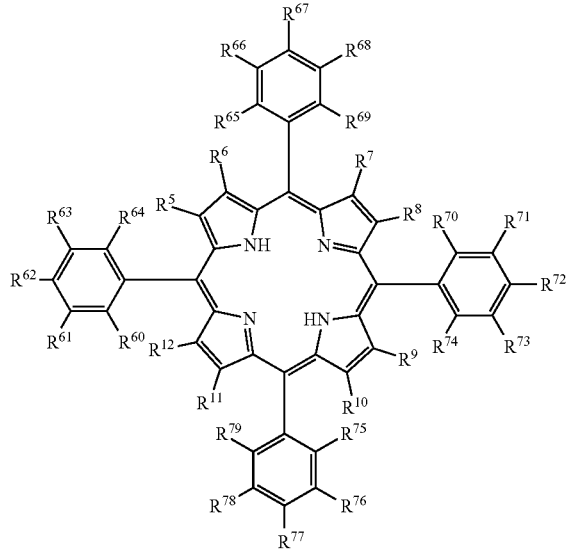

(Ia)

wherein, $R^1$-$R^{12}$, $R^{60}$-$R^{79}$ are independently selected from the group comprising H, D, FG, ($C_1$-$C_6$)alkyl, substituted ($C_1$-$C_6$)alkyl, ($C_1$-$C_6$)alkenyl, substituted ($C_1$-$C_6$)alkenyl, ($C_1$-$C_6$)alkynyl, substituted ($C_1$-$C_6$)alkynyl, hetero-($C_1$-$C_6$)alkyl, substituted hetero-($C_1$-$C_6$)alkyl, hetero-($C_1$-$C_6$)alkenyl, substituted hetero-($C_1$-$C_6$)alkenyl, hetero-($C_1$-$C_6$)alkynyl, substituted hetero-($C_1$-$C_6$)alkynyl, ($C_1$-$C_6$)cycloalkyl, substituted ($C_1$-$C_6$)cycloalkyl, aryl, substituted aryl, heterocycle, substituted heterocycle, wherein $R^5$ and $R^6$ are linked together to form a substituted or unsubstituted ring selected from the group comprising cycloalkyl, aryl and heterocycle, wherein $R^7$ and $R^8$ are linked together to form a substituted or unsubstituted ring selected from the group comprising cycloalkyl, aryl and heterocycle, wherein $R^9$ and $R^{10}$ are linked together to form a substituted or unsubstituted ring selected from the group comprising cycloalkyl, aryl and heterocycle, and wherein $R^{11}$ and $R^{12}$ are linked together to form a substituted or unsubstituted ring selected from the group comprising cycloalkyl, aryl and heterocycle.

In yet a further embodiment, a COF disclosed herein has one or more cores with a structure of Formula Ia:

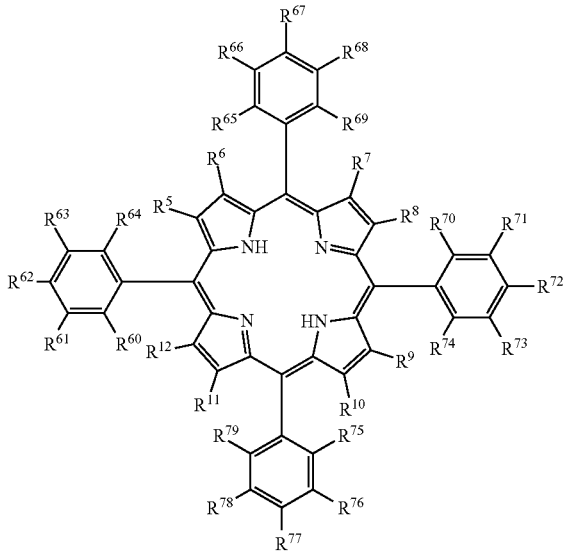

(Ia)

wherein, $R^1$-$R^{12}$, $R^{60}$-$R^{61}$, $R^{63}$-$R^{66}$, $R^{68}$-$R^{71}$, $R^{73}$-$R^{76}$ $R^{78}$-$R^{79}$ are H.

$R^{62}$, $R^{67}$, $R^{72}$, and $R^{77}$ are FG.

In yet a further embodiment, a COF disclosed herein has one or more cores and/or linking moieties that has a linking cluster that contains at least one heteroatom. In another embodiment, a COF disclosed herein has one or more cores and/or linking moieties that has a linking cluster which contains a heteroatom selected from the group comprising B, O, N, S, Si, P, Al, F, Cl, Br, and I. In yet another embodiment, a COF disclosed herein has one or more cores and/or linking moieties that has a linking cluster which contains a B, O and N.

In a certain embodiment, a COF disclosed herein has one or more cores and/or linking moieties that has a linking cluster with the formula

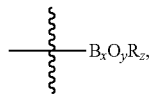

wherein x is number from 1 to 2, y is a number from 1 to 8, z is a number from 1 to 8, and R is selected from the group comprising H, D, and FG.

In another embodiment, a COF disclosed herein contains one or more linking moieties that has an organic-based parent chain which is comprised of one or more substituted or unsubstituted rings; wherein one or more of these rings is further substituted with one or more functional groups, including additional substituted or unsubstituted hydrocarbons and heterocycle groups, or a combination thereof; and wherein the linking moiety contains at least one linking cluster.

In yet another embodiment, a COF disclosed herein has one or more linking moieties with a structure selected from the group comprising Formula II, III, IV, V, VII, VIII, IX, and X:

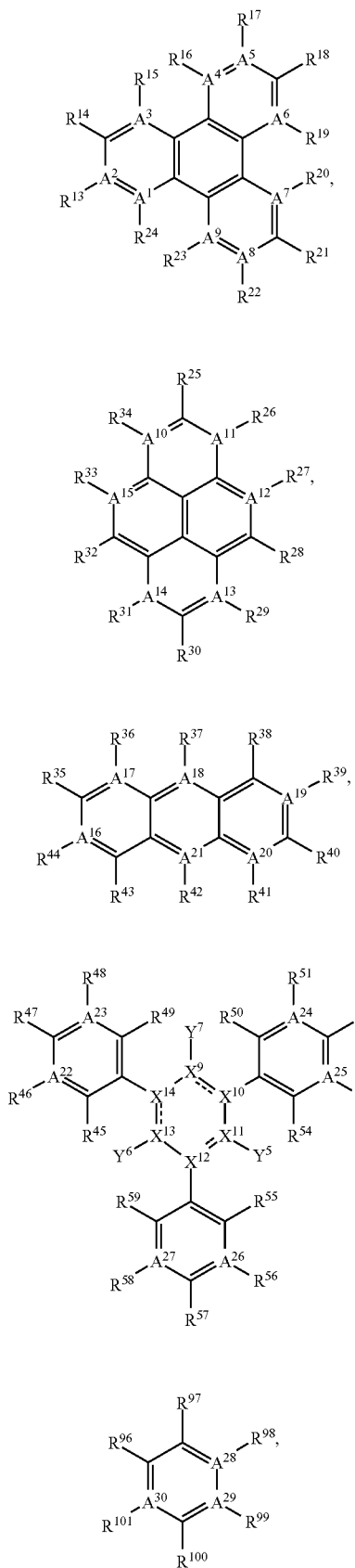

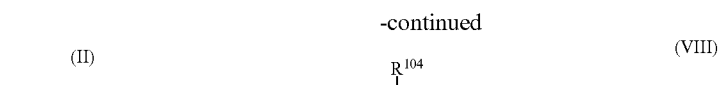
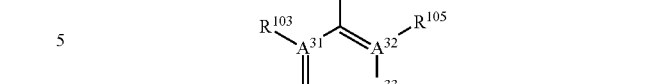
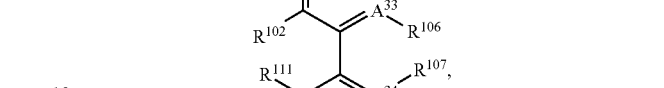
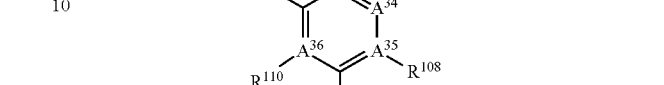
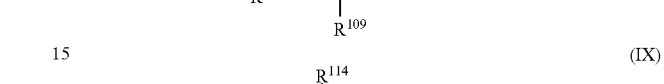
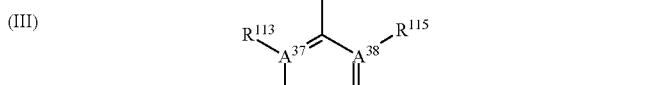
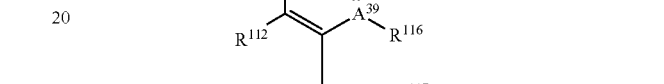
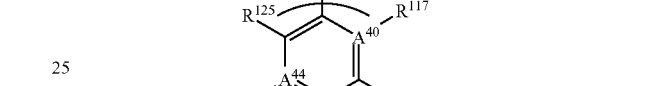
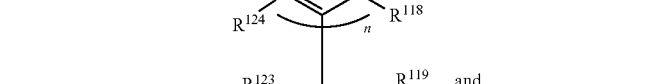
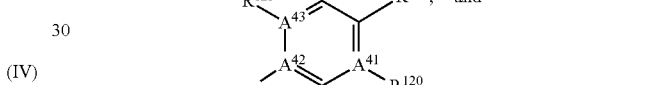
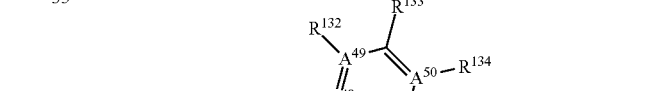
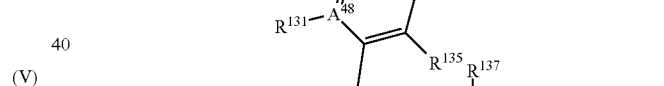
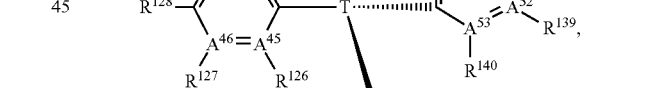
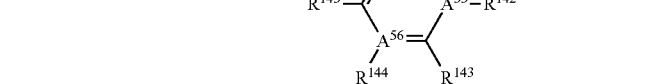

wherein:

$A^1$-$A^{56}$ are independently selected from the group comprising C, Si, N and P;

n is a number from 1 to 8;

T is selected from the group comprising an atom that can assume tetrahedral molecular geometry, a tetrahedral group, and a tetrahedral cluster;

$R^{13}$-$R^{145}$ are independently selected from the group comprising H, D, FG, $(C_1-C_{20})$alkyl, substituted $(C_1-C_{20})$alkyl, $(C_1-C_{20})$alkenyl, substituted $(C_1-C_{20})$alkenyl, $(C_1-C_{20})$alkynyl, substituted $(C_1-C_{20})$alkynyl, hetero-$(C_1-C_{20})$alkyl, substituted hetero-$(C_1$-$C_{20})$alkyl, hetero-$(C_1$-$C_{20})$alkenyl, substituted hetero-$(C_1$-$C_{20})$alkenyl, hetero-$(C_1$-$C_{20})$alkynyl, substituted hetero-$(C_1$-$C_{20})$alkynyl, $(C_1$-$C_{20})$cycloalkyl, substituted $(C_1$-$C_{20})$cycloalkyl, aryl, substituted aryl, heterocycle, and substituted heterocycle;

$X^9$-$X^{14}$ are independently selected from the group comprising carbon, oxygen, sulfur, silicon, phosphorous, and nitrogen;

$Y^5$-$Y^7$ are independently selected from the group comprising H, D, and FG;

with the proviso that a X may not exceed its maximum valence by binding a Y; and with the proviso that an A may not exceed its maximum valence by binding a R.

In a certain embodiment, a COF disclosed herein has one or more linking moieties with a structure of Formula IV:

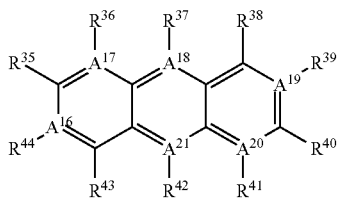

(IV)

wherein, $A^{16}$-$A^{21}$ are independently either C or N;

$R^{35}$-$R^{44}$ are independently selected from the group comprising H, D, FG, $(C_1$-$C_6)$alkyl, substituted $(C_1$-$C_6)$alkyl, $(C_1$-$C_6)$alkenyl, substituted $(C_1$-$C_6)$alkenyl, $(C_1$-$C_6)$alkynyl, substituted $(C_1$-$C_6)$alkynyl, hetero-$(C_1$-$C_5)$alkyl, substituted hetero-$(C_1$-$C_5)$alkyl, hetero-$(C_1$-$C_5)$alkenyl, substituted hetero-$(C_1$-$C_5)$alkenyl, hetero-$(C_1$-$C_5)$alkynyl, substituted hetero-$(C_1$-$C_5)$alkynyl, $(C_1$-$C_8)$cycloalkyl, substituted $(C_1$-$C_8)$cycloalkyl, aryl, substituted aryl, heterocycle, and substituted heterocycle; and with the proviso that an A may not exceed its maximum valence by binding a R.

In a further embodiment, a COF disclosed herein has one or more linking moieties with a structure of Formula IV:

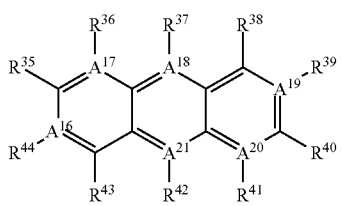

(IV)

wherein, $A^{16}$-$A^{21}$ are C;

$R^{36}$-$R^{48}$, $R^{41}$-$R^{43}$ are H; and $R^{35}$, $R^{44}$, $R^{39}$-$R^{40}$ are FG.

In yet a further embodiment, a COF disclosed herein has one or more linking moieties selected from the group comprising:

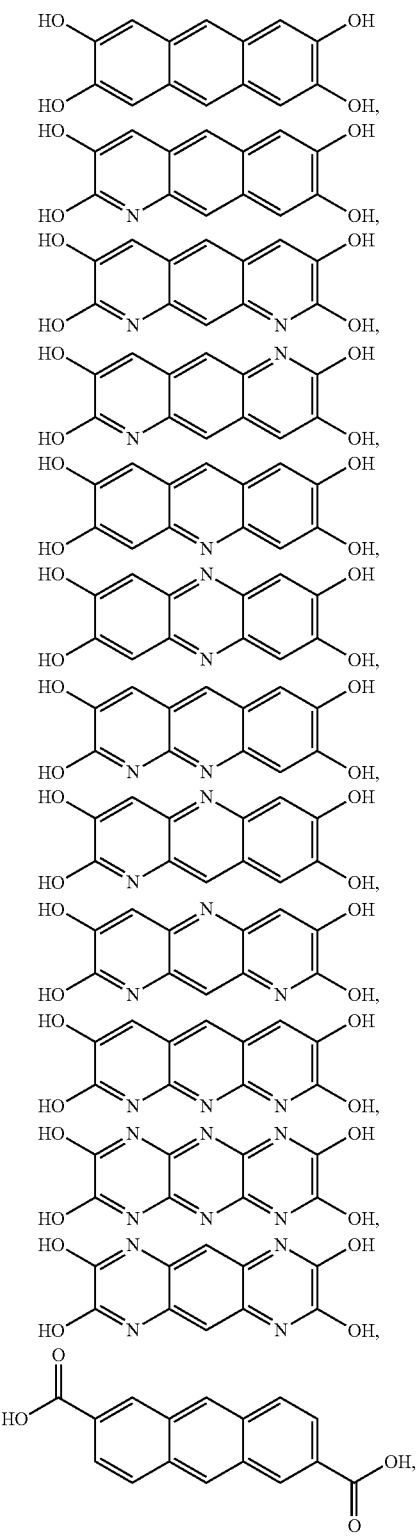

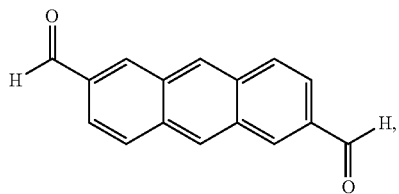

-continued

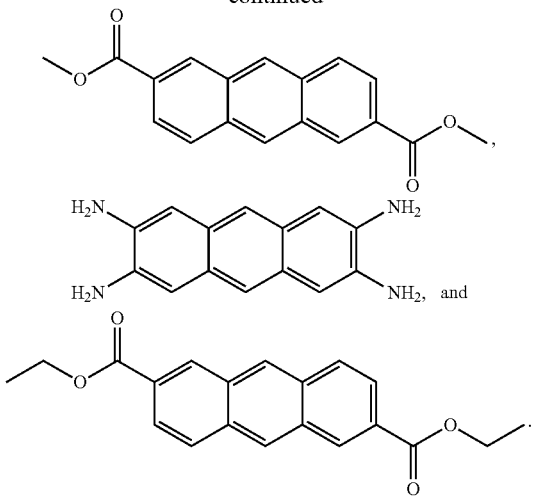

In a further embodiment, a COF disclosed herein has one or more linking moieties with a structure of Formula VII:

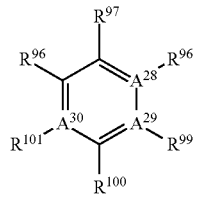

(VII)

wherein, $A^{28}$-$A^{30}$ are independently either C or N;

$R^{96}$-$R^{101}$ are independently selected from the group comprising H, D, FG, $(C_1$-$C_6)$alkyl, substituted $(C_1$-$C_6)$alkyl, $(C_1$-$C_6)$alkenyl, substituted $(C_1$-$C_6)$alkenyl, $(C_1$-$C_6)$alkynyl, substituted $(C_1$-$C_6)$alkynyl, hetero-$(C_1$-$C_5)$alkyl, substituted hetero-$(C_1$-$C_5)$alkyl, hetero-$(C_1$-$C_5)$alkenyl, substituted hetero-$(C_1$-$C_5)$alkenyl, hetero-$(C_1$-$C_5)$alkynyl, substituted hetero-$(C_1$-$C_5)$alkynyl, $(C_1$-$C_8)$cycloalkyl, substituted $(C_1$-$C_8)$cycloalkyl, aryl, substituted aryl, heterocycle, and substituted heterocycle; and with the proviso that an A may not exceed its maximum valence by binding a R.

In yet a further embodiment, a COF disclosed herein has one or more linking moieties with a structure of Formula VII:

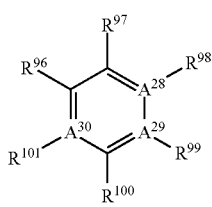

(VII)

wherein, $A^{28}$-$A^{30}$ are C;

$R^{96}$, $R^{98}$-$R^{99}$, $R^{101}$ are independently either an H or D; and $R^{97}$ and $R^{100}$ are FG.

In a certain embodiment, a COF disclosed herein has one or more linking moieties selected from the group comprising:

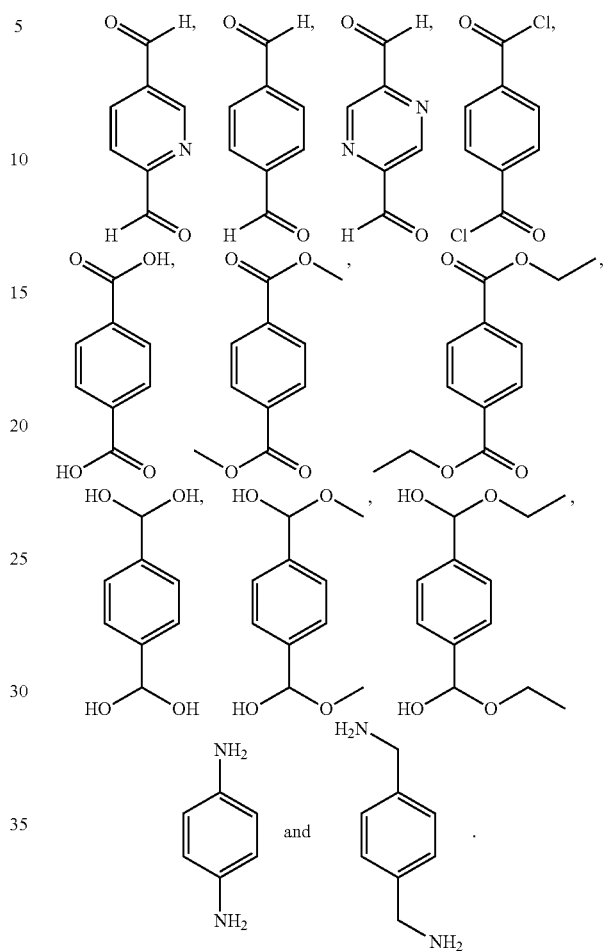

In a further embodiment, a COF disclosed herein has one or more linking moieties that has a linking cluster selected from the group comprising acyl halide, halide, ester, carboxylic acid, amine, hydroxyl, ether, and amide.

In yet a further embodiment, a COF disclosed herein is post-synthesis functionalized to comprise a metal or conductive moiety.

In another embodiment, a COF disclosed herein has hole conducting mobilities of at least 3.0 $cm^2V^{-1}s^{-1}$. In yet another embodiment, a COF disclosed herein has hole conducting mobilities of at least 8.0 $cm^2V^{-1}s^{-1}$.

In a certain embodiment, a COF disclosed herein can hold a charge for at least 75 μs.

In another embodiment, a COF disclosed herein can be used in the manufacture of a flexible display, a semiconductor, a gas storage device, and/or a chemical sensor.

In another embodiment, a COF can be used as substantially described herein with reference to the specification and figures.

DESCRIPTION OF DRAWINGS

FIG. 1A-B shows X-ray analysis of (A) COF-366, and (B) COF-66, with the observed pattern in dark grey, the refined profile in light grey, and the difference plot in medium grey (observed minus refined profiles). The bottom trace is the calculated PXRD pattern from Materials Studio.

FIG. 2A-B shows structural representations of (A) COF-366 based on powder diffraction and modeling projected along their c axis (H atoms are omitted). (B) COF-366 based on powder diffraction and modeling projected along their b axis (H atoms are omitted). Carbon, nitrogen and oxygen are represented as light grey, medium grey and dark grey spheres, respectively.

FIG. 3A-B shows structural representations of (A) COF-66 based on powder diffraction and modeling projected along their c axis (H atoms are omitted). (B) COF-66 based on powder diffraction and modeling projected along their b axis (H atoms are omitted). Carbon, boron, nitrogen and oxygen are represented as light grey, light to medium grey, medium grey and dark grey spheres, respectively.

FIG. 4A-B shows carrier mobility. (A) FP TRMC profile of COF-366 (light grey) and COF-66 (dark grey) at 25° C. upon irradiation with a 355 nm pulse laser at a power of $1.4 \times 10^{16}$ and $2.1 \times 10^{16}$ photons cm$^{-2}$, respectively. (B) Accumulated number of photo induced charge carriers upon 355 nm pulse exposure to COF-366 (dark grey)/COF-66 (light grey) sandwiched by ITO and Al electrodes. Excitation was carried out at the photon density of $9.1 \times 10^{15}$ photons cm$^{-2}$.

FIG. 8A-B shows (A) solid-state $^{13}$C NMR spectrum for COF-366, and (B) the COF-366 structure with the carbons labeled to match the $^{13}$C NMR spectrum.

FIG. 10A-B shows (A) solid-state $^{13}$C NMR spectrum for COF-66, and (B) the COF-66 structure with the carbons labeled to match the $^{13}$C NMR spectrum.

FIG. 23 shows Pore size distribution for COF-66, calculated from a NLDFT fit to the Ar adsorption data for COF-66 in FIG. 22.

FIG. 24A-B shows UV-Vis diffuse reflectance spectra (Kubela-Munk spectrum) indicate that the porphyrin units in both (a) COF-366 (light grey), TAPP (dark grey), TAPP solution in DMF (black) and (b) COF-66 (light grey), TBPP solid (dark grey), TBPP solution in DMF (black) are H-aggregate.

FIG. 28 shows transient photoabsorption spectra at the end-of-pulse observed for COF-366 (light grey) and COF-66 (dark grey) bound in PMMA matrix (COF:PMMA=2:3 w/w) upon exposure to the 355-nm line of Nd:YAG laser ($2.7 \times 10^{16}$ cm$^{-2}$). The light grey and dark grey lines are the COF-366 and COF-66, respectively. This figure indicates the new absorption band around 540 and 510 nm (for COF-66 and COF-366, respectively) in the transient spectra is originated by the formation of radical cations of porphyrin units.

FIG. 29A-B shows normalized FP-TRMC transients observed for (a) COF-66 and (b) COF-366 bound in PMMA matrix (COF: PMMA=2:3 w/w) upon exposure to the 355-nm line of Nd:YAG laser with changing the excitation power from 0.64 (light/medium grey), 0.91 (dark grey), 1.8 (medium grey), 2.7 (black), and 3.6 (light grey)$\times 10^{16}$ cm$^{-2}$.

FIG. 30A-D shows normalized decays of FP-TRMC transient (light grey) and TAS signal (dark grey) at 440 nm observed for (a, b) COF-66 and (c, d) COF-366 bound in PMMA matrix (COF:PMMA=2:3, w/w) upon exposure to the 355-nm line of Nd:YAG laser ($2.7 \times 10^{16}$ cm$^{-2}$). FIG. 30 (a, c) indicates that the transients show good agreement with each other in the shorter time region; therefore, it is possible to obtain the 'pure' conductivity values in this region by subtracting the contribution from the thermal effect. FIG. 30 (b, d) shows the deviation in the two transient curves, especially in the longer time region.

FIG. 31A-C shows current transients observed under the positive bias mode at a variety of electric field strengths in the TOF measurement for (a) COF-66 and (b) COF-366. Excitation was carried out at 355 nm, $9.1 \times 10^{15}$ photons cm$^{-2}$; (c) The linear plot of current transients under positive and negative bias modes at $1.1 \times 10^4$ V·cm$^{-1}$ for COF-66.

DETAILED DESCRIPTION

Figure 5:
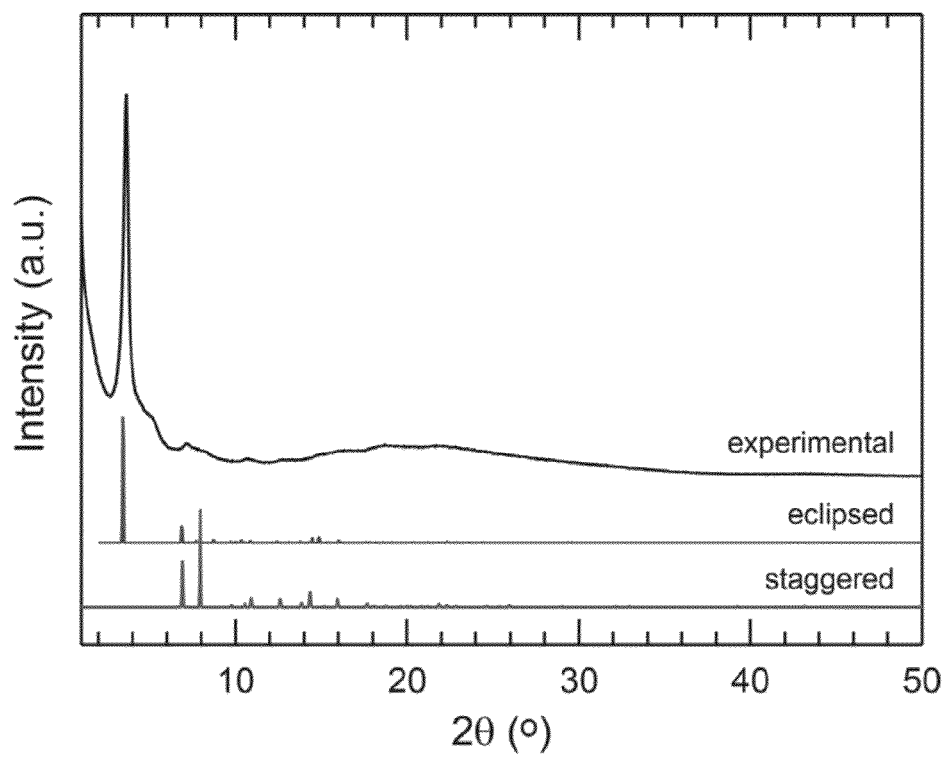
FIG. 5 shows simulated powder patterns for the staggered (dark grey) and eclipsed models (light grey) for COF-366. Experimental diffraction pattern was overlaid (black).

As used herein and in the appended claims, the singular forms "a," "and," and "the" include plural referents unless the context clearly dictates otherwise. Thus, for example, reference to "a pore" includes a plurality of such pores and reference to "the pore" includes reference to one or more pores, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure. Moreover, with respect to similar or identical terms found in the incorporated references and terms expressly defined in this disclosure, the term definitions provided in this disclosure will control in all respects.

Conductive organic materials are highly valued due to their electronic and optoelectronic properties, low cost, low molecular weight, and the relative ease in which they can be fabricated. The flexibility of the structures has also opened up new applications, such as flexible displays. It is widely believed that strong cofacial interaction between polymer chains allows charge carriers to be easily transported from one chain to another. However, linear polymers have only confined lateral overlap, and materials with large intermolecular conduction cross-section have so far remained a challenge to fabricate.

The disclosure provides covalent organic frameworks (COFs) with structures based on covalently linked porphyrin ring units to give sheets in which the porphyrin ring units are stacked laterally to give an efficient conducting interface. Exemplified herein, are two porphyrin ring COFs (COF-66 and COF-366) that were found to have hole conducting mobilities as high as 8.1 and 3.0 $cm^2 V^{-1}s^{-1}$. COF-66, COF-366 and other similar multifunctional conducting COFs, combine thermal stability with high charge mobility and pore accessibility. COF-66 and COF-366 were the first COFs to exhibit such properties, and therefore they provide an important step towards the manufacture of plastic electronics and optoelectronics.

A crucial characteristic of a semiconductor is the ability to control its electrical conductance. The most important conductive property characterizing the charge transport ability is the charge carrier mobility ($\mu$). Highly crystalline structures that have close interactions between segments are required in order to enhance the charge carrier mobility of organic semiconductors. Unlike one-dimensional polymers which usually exhibit small and limited overlap between 'slim' backbones even in the face-to-face stacking mode, two-dimensional flat sheet structures provide an ideal morphology to maximize intermolecular interactions. This is especially the case when all the atoms of one sheet are superimposeable with the atoms of the neighboring sheet. Such assemblages provide a broad path for charge carriers moving from one sheet to another, thereby enabling the eclipsed integration of $\pi$-electronic components into a well-defined 2D layered framework.

COFs are a class of porous crystalline materials that are constructed by linking secondary building units (SBUs) by covalent bonds to produce predetermined structures. According to reticular chemistry principles, the geometrical features of the SBUs determine the topology of the frameworks. Within the COF class of materials, depending on the degree of connectivity and geometry of the selected organic building units, both 3D structures and 2D layered materials can be prepared. By stacking the organic layers of 2D COFs, materials with attractive properties have been prepared. These materials feature a variety of pore sizes and high surface area. Moreover, these materials were found to adsorb gases when they were tested with $H_2$ and $NH_3$. Remarkably, the interlayer distances in these 2D structures were shorter than would be predicted, which would suggest interactions with the aromatic systems between the layers. A 2D COF with an extended $\pi$-conjugated system that has short interlayer distances could be expected to exhibit electronic interactions between the separated sheets. These COFs, therefore, could potentially be good conductors.

The disclosure provides extended $\pi$-conjugated 2D COFs that would allow for close packing of the separated sheets so as to allow for electronic interactions between the separated sheets. By utilizing porphyrin units, two novel COFs (COF-366 and COF-66) were fabricated that exhibited the highest charge carrier mobility, among known organic conducting polymers.

Covalently linked organic networks differ from existing cross-linked polymers and other polymeric materials whose properties are a result of various processing techniques that take advantage of clearly defined molecular architectures that are intrinsic to the material. Accurate control over the position of selected organic units is required in order to allow for optimum exploitation of the material properties.

Existing crystalline covalently linked materials such as diamond, graphite, silicon carbide, carbon nitride, and boron nitride are formed under very high pressures (1-10 GPa) or very high temperatures (500-2400° C.). These extreme synthetic conditions limit the flexibility needed in the formation of extended or functionalized structures, since the structural or chemical integrity of many organic monomer units is not preserved under these conditions.

In physical organic chemistry, synthesizing covalent networks under mild conditions that allows for periodic molecular structures but with long-range order has been problematic in the field for many years. Many attempts to solve this problem revolved around pre-organizing organic moieties via hydrogen bonding or metal-ligand interactions and then diffusing reactive non-metallic cross-linking agents into the channels. After these organic moieties were linked, the linking agents were removed. While forming covalent networks under mild conditions, these networks commonly suffered from incomplete polymerization or loss of crystallinity upon removal of the cross-linking or templating metal agents. The disclosure provided herein solves this long-standing problem by presenting covalent organic frameworks (COFs) in which the building blocks are linked by strong covalent bonds (C—C, C—O, B—O). The methods disclosed herein, indicate that while problematic, it is possible to overcome the long standing "crystallization problem" for covalently linked solids. The disclosure provides successful crystallization methods where a balance between the kinetic and thermodynamic factors can be reached so that reversible covalent bond formation is stabilized, a requirement for extended organic crystal structures. The disclosed COF structures contain light elements (B, C, N, and O) which provide advantages over other similar materials; in that these light element containing materials combine the thermodynamic strength of a covalent bond, as seen in diamond and boron carbides, with the functionality of organic units.

Solving the practical and conceptual challenges of synthesizing covalent networks under mild conditions that allows for periodic molecular structures but with long-range order has been extremely challenging and elusive. Firstly, unlike 0-D and 1-D systems, the insolubility of 2-D and 3-D structures precludes the use of step-wise synthesis, making their isolation in crystalline form very difficult. Secondly, the number of possible structures that may result from linking specific building unit geometries into 2-D or 3-D extended structures is essentially infinite, complicating their synthesis by design. While presenting a challenging synthesis problem, the expected properties of these materials: lightweight, inexpensive starting materials, and potentially high chemical and thermal stabilities would meet long felt needs in the physical chemical industry, such as environmentally friendly conductors for electronic devices, that are not being filled by alternative materials. These industry needs could only be met by employing specific organic units in a periodic array at the molecular scale, where one could specifically tailor structure, functionality, and material properties of these arrays in order to fulfill the particular requirements of the industrial application. In order to perform such applications, would require that the networks be synthesized under mild conditions so as not to destroy the structural or physical functionality of the building blocks in these extended networks.

Covalent organic frameworks of the disclosure are based, in part, by choosing certain building blocks and by using reversible condensation reactions to crystallize 2-D and 3-D COFs, wherein the building blocks are linked by covalent bonds. In addition, the disclosure demonstrates the usefulness of reticular chemistry. The novel COFs disclosed herein, which solved the "crystallization problem," were designed using reticular chemistry principles. For example, using reticular chemistry, nets were developed by linking different cores. The different cores can each be linked to a different number of additional cores (e.g., 2, 3, 4 or more) through a linking moiety. Each net can then be further linked to any number of additional nets.

Accordingly, the disclosure provides novel two- and three-dimensional covalent organic frameworks (3-D COFs) synthesized from molecular building blocks using concepts of reticular chemistry. For example, two nets based on triangular and tetrahedral cores, ctn and bor, were targeted and their respective 3-D COFs synthesized as crystalline solids by condensation reactions.

A covalent organic framework ("COF") refers to a two- or three-dimensional network of covalently bonded cores, wherein the cores are bonded to one another through one or more linking moieties. In one aspect a COF comprises two or more networks covalently bonded to one another. The networks may be comprised of a single type of core structure. The networks alternatively may be comprised of one or more different type of core structures. Moreover, the networks may be comprised of a single type of linking moiety. The networks alternatively may be comprised of one or more different types of linking moieties. These COFs are extended in the same sense that polymers are extended.

The term "covalent organic network" refers collectively to both covalent organic frameworks and to covalent organic polyhedra.

The term "covalent organic polyhedra" refers to a non-extended covalent organic network. Polymerization in such polyhedra does not occur usually because of the presence of capping ligands that inhibit polymerization. Covalent organic polyhedra are covalent organic networks that comprise cores that are linked to each other by one or more linking moieties so that the spatial structure of the network is a polyhedron. Typically, the polyhedra of this variation are 2 or 3 dimensional structures.

A "linking cluster" refers to one or more functional groups that are capable of undergoing reactions with functional groups and/or linking clusters found on another structure so as to form one or more covalent bonds connecting the two or more structures together so as to form a larger linked and/or fused structure. This fused structure may be linked and/or fused with additional structures through additional linking clusters so as to ultimately form 2D or 3D covalent organic frameworks. Any number of reaction mechanisms may be used in forming the one or more covalent bonds between the two or more structures, including, but not limited to, condensation, radical, unimolecular substitution ($S_N^1$), bimolecular substitution ($S_N^2$), nucleophilic aromatic substitution ($S_N^{Ar}$), unimolecular elimination (E1), bimolecular elimination (E2), $E1_cB$ elimination, pericyclic, electrocylic, sigmatropic rearrangements, cycloaddition, and electrophilic aromatic substitution. Typically, the linking cluster is covalently bonded to one or more other linking clusters or functional groups through a condensation reaction.

The term "alkyl" refers to an alkyl group that contains 1 to 30 carbon atoms. Where if there is more than 1 carbon, the carbons may be connected in a linear manner, or alternatively if there are more than 2 carbons then the carbons may also be linked in a branched fashion so that the parent chain contains one or more secondary, tertiary, or quaternary carbons. An alkyl may be substituted or unsubstituted, unless stated otherwise.

The term "alkenyl" refers to an alkenyl group that contains 1 to 30 carbon atoms. While a $C_1$-alkenyl can form a double bond to a carbon of a parent chain, an alkenyl group of three or more carbons can contain more than one double bond. It certain instances the alkenyl group will be conjugated, in other cases an alkenyl group will not be conjugated, and yet other cases the alkenyl group may have stretches of conjugation and stretches of nonconjugation. Additionally, if there is more than 1 carbon, the carbons may be connected in a linear manner, or alternatively if there are more than 3 carbons then the carbons may also be linked in a branched fashion so that the parent chain contains one or more secondary, tertiary, or quaternary carbons. An alkenyl may be substituted or unsubstituted, unless stated otherwise.

The term "alkynyl" refers to an alkynyl group that contains 1 to 30 carbon atoms. While a $C_1$-alkynyl can form a triple bond to a carbon of a parent chain, an alkynyl group of three or more carbons can contain more than one triple bond. Where if there is more than 1 carbon, the carbons may be connected in a linear manner, or alternatively if there are more than 4 carbons then the carbons may also be linked in a branched fashion so that the parent chain contains one or more secondary, tertiary, or quaternary carbons. An alkynyl may be substituted or unsubstituted, unless stated otherwise.

The term "cycloalkyl" refers to an alkyl that contains at least 3 carbon atoms but no more than 12 carbon atoms connected so that it forms a ring. A "cycloalkyl" for the purposes of this disclosure encompass from 1 to 7 cycloalkyl rings, wherein when the cycloalkyl is greater than 1 ring, then the cycloalkyl rings are joined so that they are linked, fused, or a combination thereof. A cycloalkyl may be substituted or unsubstituted, or in the case of more than one cycloalkyl ring, one or more rings may be unsubstituted, one or more rings may be substituted, or a combination thereof.

The term "aryl" refers to a conjugated planar ring system with delocalized pi electron clouds that contain only carbon as ring atoms. An "aryl" for the purposes of this disclosure encompass from 1 to 7 aryl rings wherein when the aryl is greater than 1 ring the aryl rings are joined so that they are linked, fused, or a combination thereof. An aryl may be substituted or unsubstituted, or in the case of more than one aryl ring, one or more rings may be unsubstituted, one or more rings may be substituted, or a combination thereof.

The term "heterocycle" refers to ring structures that contain at least 1 noncarbon ring atom. A "heterocycle" for the purposes of this disclosure encompass from 1 to 7 heterocycle rings wherein when the heterocycle is greater than 1 ring the heterocycle rings are joined so that they are linked, fused, or a combination thereof. A heterocycle may be aromatic or nonaromatic, or in the case of more than one heterocycle ring, one or more rings may be nonaromatic, one or more rings may be aromatic, or a combination thereof. A heterocycle may be substituted or unsubstituted, or in the case of more than one heterocycle ring one or more rings may be unsubstituted, one or more rings may be substituted, or a combination thereof. Typically, the noncarbon ring atom is either N, O, S, Si, Al, B, or P. In case where there is more than one noncarbon ring atom, these noncarbon ring atoms can either be the same element, or combination of different elements, such as N and O. Examples of heterocycles include, but are not limited to: a monocyclic heterocycle such as, aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide; and polycyclic heterocycles such as, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, and quinolizidine. In addition to the polycyclic heterocycles described above, heterocycle includes polycyclic heterocycles wherein the ring fusion between two or more rings includes more than one bond common to both rings and more than two atoms common to both rings. Examples of such bridged heterocycles include quinuclidine, diazabicyclo[2.2.1]heptane and 7-oxabicyclo[2.2.1]heptane.

The terms "heterocyclic group", "heterocyclic moiety", "heterocyclic", or "heterocyclo" used alone or as a suffix or prefix, refers to a heterocycle that has had one or more hydrogens removed therefrom.

The term "heterocyclyl" used alone or as a suffix or prefix, refers a monovalent radical derived from a heterocycle by removing one hydrogen therefrom. Heterocyclyl includes, for example, monocyclic heterocyclyls, such as, aziridinyl, oxiranyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydrofuranyl, thiophenyl, piperidinyl, 1,2,3,6-tetrahydro-pyridinyl, piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-1H-azepinyl, homopiperazinyl, 1,3-dioxepanyl, 4,7-dihydro-1,3-dioxepinyl, and hexamethylene oxidyl. In addition, heterocyclyl includes aromatic heterocyclyls or heteroaryl, for example, pyridinyl, pyrazinyl, pyrimidinyl, pyridazinyl, thienyl, furyl, furazanyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4oxadiazolyl. Additionally, heterocyclyl encompasses polycyclic heterocyclyls (including both aromatic or non-aromatic), for example, indolyl, indolinyl, isoindolinyl, quinolinyl, tetrahydroquinolinyl, isoquinolinyl, tetrahydroisoquinolinyl, 1,4-benzodioxanyl, coumarinyl, dihydrocumarinyl, benzofuranyl, 2,3-dihydrobenzofuranyl, isobenzofuranyl, chromenyl, chromanyl, isochromanyl, xanthenyl, phenoxathiinyl, thianthrenyl, indolizinyl, isoindolyl, indazolyl, purinyl, phthalazinyl, naphthyridinyl, quinoxalinyl, quinazolinyl, cinnolinyl, pteridinyl, phenanthridinyl, perimidinyl, phenanthrolinyl, phenazinyl, phenothiazinyl, phenoxazinyl, 1,2-benzisoxazolyl, benzothiophenyl, benzoxazolyl, benzthiazolyl, benzimidazolyl, benztriazolyl, thioxanthinyl, carbazolyl, carbolinyl, acridinyl, pyrolizidinyl, and quinolizidinyl. In addition to the polycyclic heterocyclyls described above, heterocyclyl includes polycyclic heterocyclyls wherein the ring fusion between two or more rings includes more than one bond common to both rings and more than two atoms common to both rings. Examples of such bridged heterocycles include, but is not limited to, quinuclidinyl, diazabicyclo[2.2.1]heptyl; and 7-oxabicyclo[2.2.1]heptyl.

The term "hetero-aryl" used alone or as a suffix or prefix, refers to a heterocyclyl having aromatic character. Examples of heteroaryls include, but is not limited to, pyridine, pyrazine, pyrimidine, pyridazine, thiophene, furan, furazan, pyrrole, imidazole, triazole, oxazole, pyrazole, isothiazole, isoxazole, 1,2,3-triazole, tetrazole, 1,2,3-thiadiazole, 1,2,3-oxadiazole, 1,2,4-triazole, 1,2,4-thiadiazole, 1,2,4-oxadiazole, 1,3,4-triazole, 1,3,4-thiadiazole, and 1,3,4-oxadiazole.

The term "hetero-" when used as a prefix, such as, hetero-alkyl, hetero-alkenyl, hetero-alkynyl, or hetero-hydrocarbon, for the purpose of this disclosure refers to the specified hydrocarbon having one or more carbon atoms replaced by non-carbon atoms as part of the parent chain. Examples of such noncarbon atoms include, but are not limited to, N, O, S, Si, Al, B, and P. If there is more than one noncarbon atom in the hetero-hydrocarbon chain then this atom may be the same element or may be a combination of different elements, such as N and O.

The term "unsubstituted" with respect to hydrocarbons, heterocycles, and the like, refers to structures wherein the parent chain contains no substituents.

The term "substituted" with respect to hydrocarbons, heterocycles, and the like, refers to structures wherein the parent chain contains one or more substituents.

The term "substituent" refers to an atom or group of atoms substituted in place of a hydrogen atom. For purposes of this disclosure, a substituent would include deuterium atoms.

The term "hydrocarbons" refers to groups of atoms that contain only carbon and hydrogen. Examples of hydrocarbons that can be used in this disclosure include, but are not limited to, alkanes, alkenes, alkynes, aryls, and benzyls.

The term "functional group" or "FG" refers to specific groups of atoms within molecules that are responsible for the characteristic chemical reactions of those molecules. While the same functional group will undergo the same or similar chemical reaction(s) regardless of the size of the molecule it is a part of, its relative reactivity can be modified by nearby functional groups. The atoms of functional groups are linked to each other and to the rest of the molecule by covalent bonds. Examples of FG that can be used in this disclosure, include, but are not limited to, substituted or unsubstituted alkyls, substituted or unsubstituted alkenyls, substituted or unsubstituted alkynyls, substituted or unsubstituted aryls, substituted or unsubstituted hetero-alkyls, substituted or unsubstituted hetero-alkenyls, substituted or unsubstituted hetero-alkynyls, substituted or unsubstituted hetero-aryls, substituted or unsubstituted heterocycles, halos, haloformyls, oxygen containing groups (e.g. hydroxyls, anhydrides, carbonyls, carboxyls, carbonates, carboxylates, aldehydes, esters, hydroperoxy, peroxy, ethers, and orthoesters), nitrogen-containing groups (e.g. carboxamides, amines, imines, imides, azides, azos, cyanates, isocyanates, nitrates, nitriles, isonitriles, nitrosos, nitros, nitrosooxy), sulfur-containing groups (sulfhydryls, sulfides, disulfides, sulfinyls, sulfos, thiocyanates, isothiocyanates, and carbonothioyls), phosphorous-containing groups (e.g. phosphinos, phosphonos, and phosphates), silicon-containing groups ($Si(OH)_3$, $Si(SH)_4$, silanes, silyls, and siloxanes), boron containing groups (e.g. boronic acid, boronic esters, and boronic ethers), and metal or metalloid-containing groups (e.g. $Ge(OH)_3$, $Ge(SH)_4$, $AsO_3H$, $AsO_4H$, $As(SH)_3$, $Sn(OH)_3$, $Sn(CH_3)_3$, and $Sn(Bu)_3$).

As used herein, a wavy line intersecting another line in a chemical formula where this line is connected to an atom on one end and nothing on the other end indicates that this atom is covalently bonded to another atom that is present but not being shown.

A bond that is represented by a straight line and a dashed line indicates that this bond can be a single covalent bond or alternatively a doubly covalent bond.

A "core" refers to an organic compound which can form one or more covalent bonds with a linking moiety through a linking cluster. Generally, a core comprises a substantially planar parent chain that is comprised mainly of aryls, heterocylces, heteroalkenyls, heteroalkynyls or a combination thereof; wherein the parent chain may be unsubstituted or substituted with one or more functional groups, including substituted or unsubstituted hydrocarbons, heterocycles, or a combination thereof; and wherein the core can form one or more covalent bonds with one or more linking clusters of one or more linking moieties. Typically cores are planar conjugated structures that contain from two to eight aryls, aromatic heterocycles, or combination thereof. Examples of core structures include, but are not limited to, porphyrin, porphyrin analogs, corrinoid, corrinoid analogs, naphthalene, naphthalene analogs, anthracene, anthracene analogs, phenathrene, phenathrene analogs, pyrene, pyrene analogs, linked 2 to 8 aryl rings, linked 2 to 8 aromatic heterocyle rings, fused 2 to 8 aryl and aromatic heterocycle rings, and linked 2 to 8 aryl and aromatic heterocycle rings.

A "linking moiety" refers to an organic compound which can form one or more covalent bonds with a core through a linking cluster. Generally, a linking moiety comprises a parent chain of a hydrocarbon, hetero-alkane, hetero-alkene, hetero-alkyne, or heterocycles; where this parent chain may be substituted with one or more functional groups, including additional substituted or unsubstituted hydrocarbons, and heterocycles, or a combination thereof; and wherein the linking moiety contains at least one linking cluster. In the case of heterocycles, hetero-alkanes, hetero-alkenes, and hetero-alkynes, one or more heteroatoms can function as a linking cluster. Examples of such heteroatoms include, but are not limited to, nitrogen, oxygen, sulfur, boron, phosphorus, silicon or aluminum atoms making up the ring. Moreover, a heterocycle, hetero-alkane, hetero-alkene, or hetero-alkyne, can also be functionalized with one or more linking clusters.

Moreover, a heterocycle, hetero-alkane, hetero-alkene, or hetero-alkyne, can also be functionalized with one or more ligands to add or increase denticity of the hetero-based parent chain. In the case of hydrocarbons, typically one or more of the linking clusters of the hydrocarbon-based linking moiety can arise from functionalizing the hydrocarbon parent chain with one or more functional groups that can then act as a linking cluster. Examples of such groups, include, but are not limited to, carboxylic acids, hydroxyls, amines, imines, thiols, phosphines, ketones, aldehydes, halides, cyanos, boronic acid and nitros. In certain cases, portions of a hydrocarbon itself can function as a linking cluster, for example by forming carbenes and carbocations. It is also well known that functional groups that can be linking clusters that are also Lewis bases, have lone pair electrons available and/or can be deprotonated to form stronger Lewis bases. The deprotonated version of these linking clusters, therefore, are encompassed by disclosure and anywhere a ligand that is depicted in a non-deprotenated form, the deprotenated form should be presumed to be included, unless stated otherwise. For example, although the structural Formulas presented herein are illustrated as having carboxylic acid ligands, for the purposes of this disclosure, those illustrated structures should be interpreted as including both carboxylic acid and/or carboxylate ligands.

The term "post framework reactants" refers to all known substances that are directly involved in a chemical reaction. Post framework reactants typically are substances, either elemental or compounds, which have not reached the optimum number of electrons in their outer valence levels and/or have not reached the most favorable energetic state due to ring strain, bond length, low bond dissociation energy, and the like. Some examples of post framework reactants include, but are not limited to:

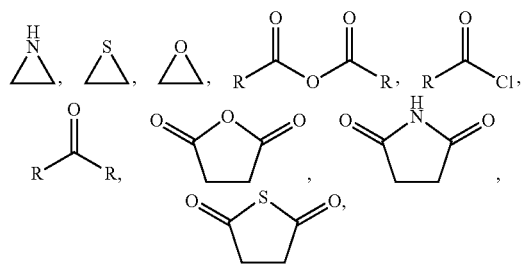

I—R, Br—R, $CR_3$—Mg—Br, $CH_2R$-$L_1$, $CR_3$, Na—R, and K—R; and wherein each R is independently selected from the group comprising: H, sulfonates, tosylates, azides, triflates, ylides, alkyl, aryl, OH, alkoxy, alkenes, alkynes, phenyl and substitutions of the foregoing, sulfur-containing groups (e.g., thioalkoxy, thionyl chloride), silicon-containing groups, nitrogen-containing groups (e.g., amides and amines), oxygen-containing groups (e.g., ketones, carbonates, aldehydes, esters, ethers, and anhydrides), halogen, nitro, nitrile, nitrate, nitroso, amino, cyano, ureas, boron-containing groups (e.g., sodium borohydride, and catecholborane), phosphorus-containing groups (e.g., phosphorous tribromide), and aluminum-containing groups (e.g., lithium aluminum hydride).

The disclosure provides covalently linked organic networks of any number of net structures (e.g., frameworks). The covalently linked organic network comprises a plurality of cores wherein at least two cores contain one or more linking clusters capable of forming one or more covalent bonds with one or more linking clusters of one or more linking moieties. The cores are linked to one another by at least one linking moiety. Variations of the covalently linked organic networks (both the frameworks and polyhedra) can provide surface areas from about 1 to about 20,000 m²/g or more, typically about 2000 to about 18,000 m²/g, but more commonly about 3,000 to about 6,000 m²/g.

Typically each core is linked to at least one, typically two, distinct cores through one or more linking moieties. In a variation of this embodiment, the covalently linked organic networks are COFs that have extended structures. In a further refinement these COFs are crystalline materials that may be either polycrystalline or even single crystals. The cores may be the same throughout the net (i.e., a homogenous net) or may be different or alternating types of cores (i.e., a heterogeneous net). Since the COFs are extended structures, variations may form into analogous nets to the nets found in metallic organic frameworks as described in Reticular Chemistry: Occurrence and Taxonomy of Nets and Grammar for the Design of Frameworks, Acc. Chem. Res. 2005, 38, 176-182. The entire disclosure of this article is hereby incorporated by reference.

In an embodiment, a COF disclosed herein is generated from cores that have the same structure. In another embodiment, a COF disclosed herein is generated from at least two cores that have a different structure.

In a further embodiment, a COF disclosed herein is generated from one or more cores comprised of fused aryl rings. In a certain embodiment, a COF disclosed herein is generated from one or more cores comprised of fused aromatic heterocycles. In yet a further embodiment, a COF disclosed herein is generated from one or more cores comprised of fused aryl and aromatic heterocycle rings. In another embodiment, a COF disclosed herein is generated from one or more cores that have a porphyrin or porphyrin analog based structure.

In a certain embodiment, a COF disclosed herein is generated from one or more cores that have a structure selected from the group comprising Formula I, II, III, IV, and V:

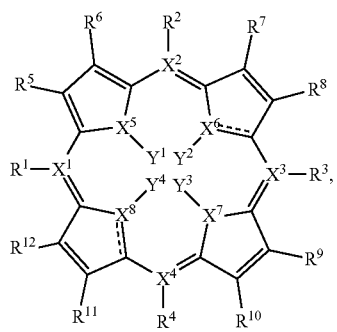

(I)

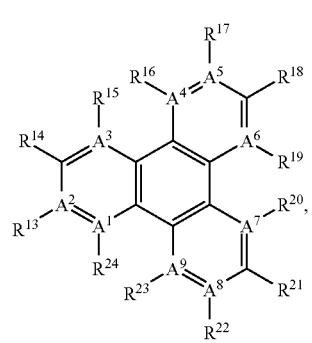

(II)

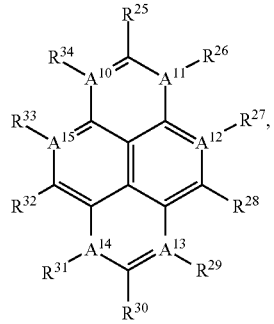

(III)

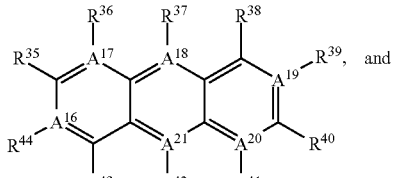

(IV)

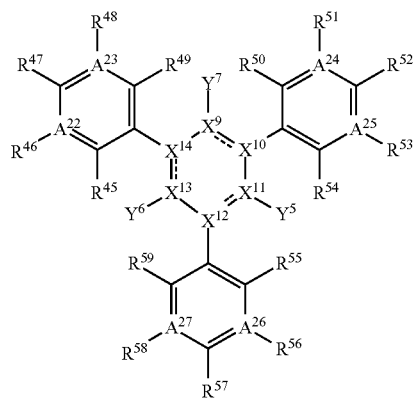

(V)

wherein:
$R^1$-$R^{59}$ are independently selected from the group comprising H, D, FG, $(C_1-C_{20})$alkyl, substituted $(C_1-C_{20})$alkyl, $(C_1-C_{20})$alkenyl, substituted $(C_1-C_{20})$alkenyl, $(C_1-C_{20})$alkynyl, substituted $(C_1-C_{20})$alkynyl, hetero-$(C_1-C_{20})$alkyl, substituted hetero-$(C_1-C_{20})$alkyl, hetero-$(C_1-C_{20})$alkenyl, substituted hetero-$(C_1-C_{20})$alkenyl, hetero-$(C_1-C_{20})$alkynyl, substituted hetero-$(C_1-C_{20})$alkynyl, $(C_1-C_{20})$cycloalkyl, substituted $(C_1-C_{20})$cycloalkyl, aryl, substituted aryl, heterocycle, substituted heterocycle, wherein $R^5$ and $R^6$ are linked together to form a substituted or unsubstituted ring selected from the group comprising cycloalkyl, aryl and heterocycle, wherein $R^7$ and $R^8$ are linked together to form a substituted or unsubstituted ring selected from the group comprising cycloalkyl, aryl and heterocycle, wherein $R^9$ and $R^{16}$ are linked together to form a substituted or unsubstituted ring selected from the group comprising cycloalkyl, aryl and heterocycle, and wherein $R^{11}$ and $R^{12}$ are linked together to form a substituted or unsubstituted ring selected from the group comprising cycloalkyl, aryl and heterocycle;

$X^1$-$X^{13}$ are independently selected from the group comprising carbon, oxygen, sulfur, silicon, phosphorous, and nitrogen;

$Y^1$-$Y^7$ are independently selected from the group comprising H, D, and FG;

$A^1$-$A^{27}$ are independently selected from the group comprising C, N, Si or P;

with the proviso that a X may not exceed its maximum valence by binding a Y, or $R^1$-$R^4$; and with the proviso that a A may not exceed its maximum valence by binding a R.

In another embodiment, a COF disclosed herein is generated from one or more cores that have a structure of Formula I:

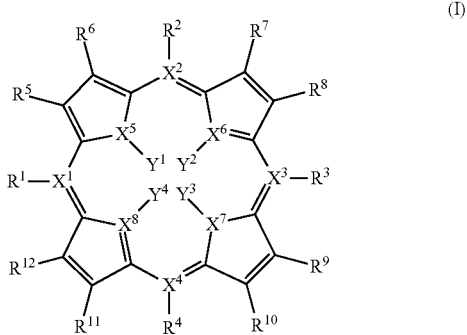

(I)

wherein, $R^1$-$R^{12}$ are independently selected from the group comprising H, D, FG, $(C_1$-$C_6)$alkyl, substituted $(C_1$-$C_6)$alkyl, $(C_1$-$C_6)$alkenyl, substituted $(C_1$-$C_6)$alkenyl, $(C_1$-$C_6)$alkynyl, substituted $(C_1$-$C_6)$alkynyl, hetero-$(C_1$-$C_6)$alkyl, substituted hetero-$(C_1$-$C_6)$alkyl, hetero-$(C_1$-$C_6)$alkenyl, substituted hetero-$(C_1$-$C_6)$alkenyl, hetero-$(C_1$-$C_6)$alkynyl, substituted hetero-$(C_1$-$C_6)$alkynyl, $(C_1$-$C_6)$cycloalkyl, substituted $(C_1$-$C_6)$cycloalkyl, aryl, substituted aryl, heterocycle, substituted heterocycle, wherein $R^5$ and $R^6$ are linked together to form a substituted or unsubstituted ring selected from the group comprising cycloalkyl, aryl and heterocycle, wherein $R^7$ and $R^8$ are linked together to form a substituted or unsubstituted ring selected from the group comprising cycloalkyl, aryl and heterocycle, wherein $R^9$ and $R^{10}$ are linked together to form a substituted or unsubstituted ring selected from the group comprising cycloalkyl, aryl and heterocycle, and wherein $R^{11}$ and $R^{12}$ are linked together to form a substituted or unsubstituted ring selected from the group comprising cycloalkyl, aryl and heterocycle;

$X^1$-$X^8$ are independently selected from the group comprising carbon or nitrogen;

$Y^1$-$Y^4$ are independently selected from the group comprising H, D, FG; and with the proviso that a X may not exceed its maximum valence by binding a Y, or $R^1$-$R^4$.

In a further embodiment, the covalent organic framework is generated from one or more cores of Formula I that have a structure of Formula Ia:

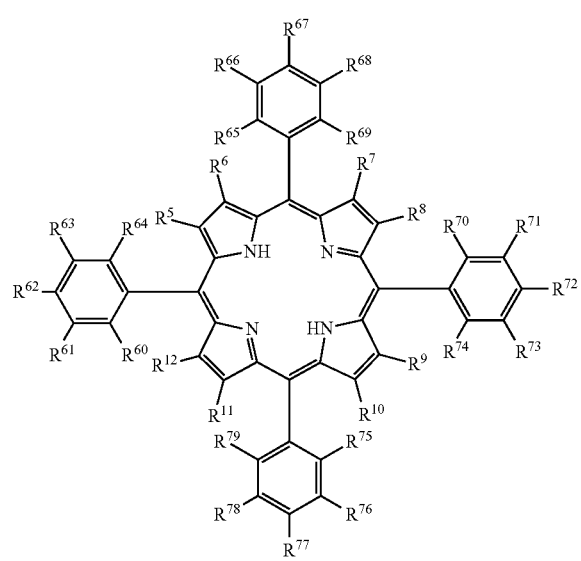

(Ia)

wherein, $R^1$-$R^{12}$, $R^{60}$-$R^{79}$ are independently selected from the group comprising H, D, FG, $(C_1$-$C_6)$alkyl, substituted $(C_1$-$C_6)$alkyl, $(C_1$-$C_6)$alkenyl, substituted $(C_1$-$C_6)$alkenyl, $(C_1$-$C_6)$alkynyl, substituted $(C_1$-$C_6)$alkynyl, hetero-$(C_1$-$C_6)$alkyl, substituted hetero-$(C_1$-$C_6)$alkyl, hetero-$(C_1$-$C_6)$alkenyl, substituted hetero-$(C_1$-$C_6)$alkenyl, hetero-$(C_1$-$C_6)$alkynyl, substituted hetero-$(C_1$-$C_6)$alkynyl, $(C_1$-$C_6)$cycloalkyl, substituted $(C_1$-$C_6)$cycloalkyl, aryl, substituted aryl, heterocycle, substituted heterocycle, wherein $R^5$ and $R^6$ are linked together to form a substituted or unsubstituted ring selected from the group comprising cycloalkyl, aryl and heterocycle, wherein $R^7$ and $R^8$ are linked together to form a substituted or unsubstituted ring selected from the group comprising cycloalkyl, aryl and heterocycle, wherein $R^9$ and $R^{10}$ are linked together to form a substituted or unsubstituted ring selected from the group comprising cycloalkyl, aryl and heterocycle, and wherein $R^{11}$ and $R^{12}$ are linked together to form a substituted or unsubstituted ring selected from the group comprising cycloalkyl, aryl and heterocycle In further embodiment, the covalent organic framework is generated from one or more cores of Formula Ia:

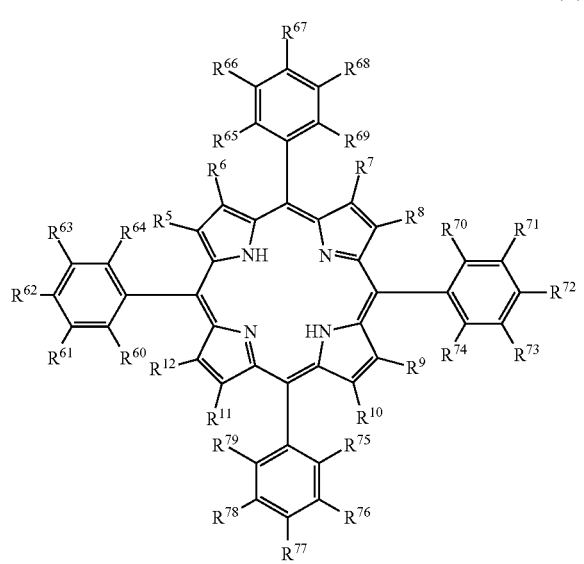

(Ia)

wherein, $R^1$-$R^{12}$, $R^{60}$-$R^{61}$, $R^{63}$-$R^{66}$, $R^{68}$-$R^{71}$, $R^{73}$-$R^{76}$, $R^{78}$-$R^{79}$ are H.

$R^{62}$, $R^{67}$, $R^{72}$, and $R^{77}$ are FG.

In a certain embodiment, a COF disclosed herein is generated from one or more cores of Formula I that have a structure of Formula Ib:

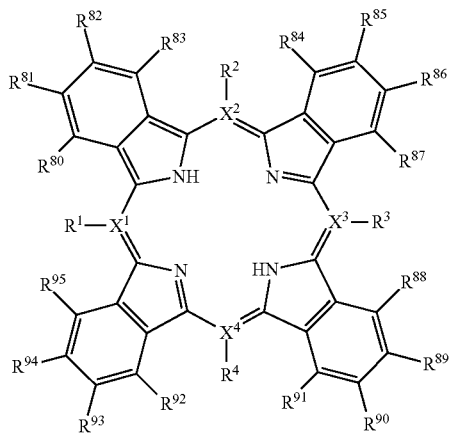
(Ib)

wherein, $R^1$-$R^4$, $R^{80}$-$R^{95}$ are independently selected from the group comprising H, D, FG, $(C_1$-$C_6)$alkyl, substituted $(C_1$-$C_6)$alkyl, $(C_1$-$C_6)$alkenyl, substituted $(C_1$-$C_6)$alkenyl, $(C_1$-$C_6)$alkynyl, substituted $(C_1$-$C_6)$alkynyl, hetero-$(C_1$-$C_6)$alkyl, substituted hetero-$(C_1$-$C_6)$alkyl, hetero-$(C_1$-$C_6)$alkenyl, substituted hetero-$(C_1$-$C_6)$alkenyl, hetero-$(C_1$-$C_6)$alkynyl, substituted hetero-$(C_1$-$C_6)$alkynyl, $(C_1$-$C_6)$cycloalkyl, substituted $(C_1$-$C_6)$cycloalkyl, aryl, substituted aryl, heterocycle, and substituted heterocycle;

$X^1$-$X^4$ are independently selected from the group comprising carbon and nitrogen; and with the proviso that a X may not exceed its maximum valence by binding a R.

In another embodiment, a core and/or linking moiety disclosed herein comprises a compound having structural Formula (II):

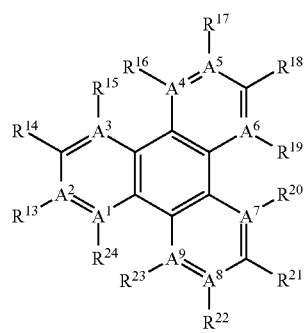
(II)

wherein, $A^1$-$A^9$ are independently either C or N;

$R^{13}$-$R^{24}$ are independently selected from the group comprising H, D, FG, $(C_1$-$C_6)$alkyl, substituted $(C_1$-$C_6)$alkyl, $(C_1$-$C_6)$alkenyl, substituted $(C_1$-$C_6)$alkenyl, $(C_1$-$C_6)$alkynyl, substituted $(C_1$-$C_6)$alkynyl, hetero-$(C_1$-$C_5)$alkyl, substituted hetero-$(C_1$-$C_5)$alkyl, hetero-$(C_1$-$C_5)$alkenyl, substituted hetero-$(C_1$-$C_5)$alkenyl, hetero-$(C_1$-$C_6)$alkynyl, substituted hetero-$(C_1$-$C_5)$alkynyl, $(C_1$-$C_8)$cycloalkyl, substituted $(C_1$-$C_8)$cycloalkyl, aryl, substituted aryl, heterocycle, and substituted heterocycle; and with the proviso that an A may not exceed its maximum valence by binding a R.

In a further embodiment, a core and/or linking moiety of Formula (II) has the structure:

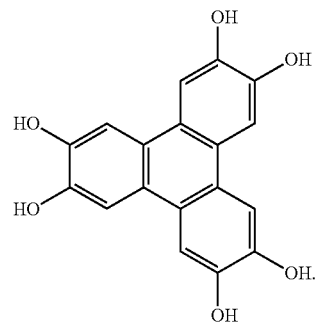 [SMILES: Oc1cc2c3cc(O)c(O)cc3c3cc(O)c(O)cc3c2cc1O]

In another embodiment, a core and/or linking moiety disclosed herein comprises a compound having structural Formula (III):

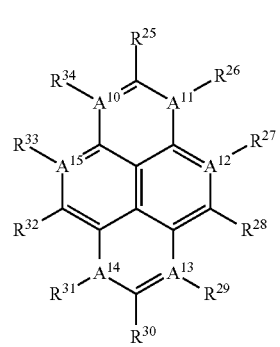
(III)

wherein, $A^{10}$-$A^{15}$ are independently either C or N;

$R^{25}$-$R^{34}$ are independently selected from the group comprising H, D, FG, $(C_1$-$C_6)$alkyl, substituted $(C_1$-$C_6)$alkyl, $(C_1$-$C_6)$alkenyl, substituted $(C_1$-$C_6)$alkenyl, $(C_1$-$C_6)$alkynyl, substituted $(C_1$-$C_6)$alkynyl, hetero-$(C_1$-$C_5)$alkyl, substituted hetero-$(C_1$-$C_5)$alkyl, hetero-$(C_1$-$C_5)$alkenyl, substituted hetero-$(C_1$-$C_5)$alkenyl, hetero-$(C_1$-$C_5)$alkynyl, substituted hetero-$(C_1$-$C_5)$alkynyl, $(C_1$-$C_8)$cycloalkyl, substituted $(C_1$-$C_8)$cycloalkyl, aryl, substituted aryl, heterocycle, and substituted heterocycle; and with the proviso that an A may not exceed its maximum valence by binding a R.

In a further embodiment, a core and/or linking moiety of Formula (III) has the structure selected from the group comprising:

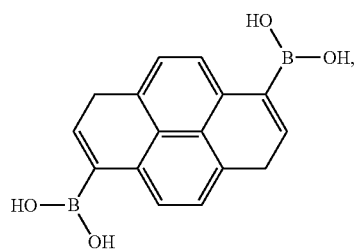

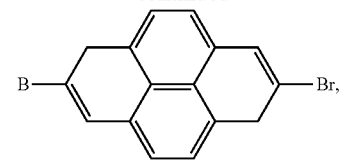

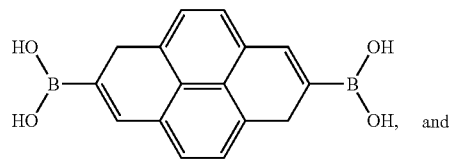

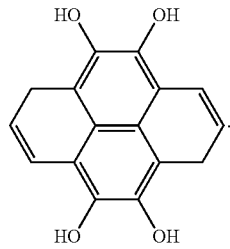

In a further embodiment, a core and/or linking moiety disclosed herein comprises a compound having structural Formula (IV):

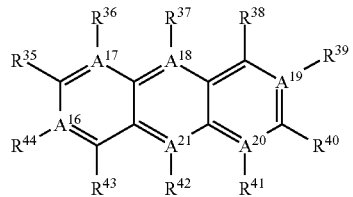

wherein, $A^{16}$-$A^{21}$ are independently either C or N;

$R^{35}$-$R^{44}$ are independently selected from the group comprising H, D, FG, ($C_1$-$C_6$)alkyl, substituted ($C_1$-$C_6$)alkyl, ($C_1$-$C_6$)alkenyl, substituted ($C_1$-$C_6$)alkenyl, ($C_1$-$C_6$)alkynyl, substituted ($C_1$-$C_6$)alkynyl, hetero-($C_1$-$C_5$)alkyl, substituted hetero-($C_1$-$C_5$)alkyl, hetero-($C_1$-$C_5$)alkenyl, substituted hetero-($C_1$-$C_5$)alkenyl, hetero-($C_1$-$C_5$)alkynyl, substituted hetero-($C_1$-$C_5$)alkynyl, ($C_1$-$C_8$)cycloalkyl, substituted ($C_1$-$C_8$)cycloalkyl, aryl, substituted aryl, heterocycle, and substituted heterocycle; and with the proviso that an A may not exceed its maximum valence by binding a R.

In another embodiment, a core and/or linking moiety disclosed herein comprises a compound having structural Formula (V):

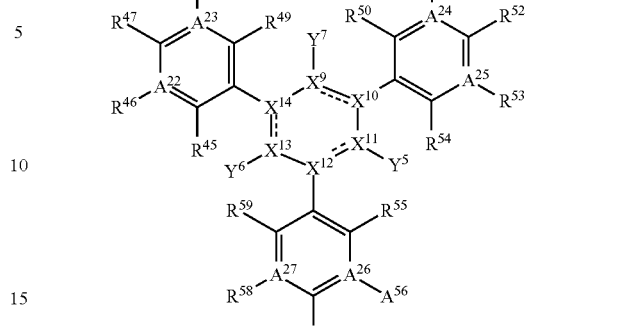

wherein, $X^9$-$X^{14}$ are independently either C, N or P;

$Y^5$-$Y^7$ are independently either H, D, or FG;

$A^{22}$-$A^{27}$ are independently either C or N;

$R^{45}$-$R^{59}$ are independently selected from the group comprising H, D, FG, ($C_1$-$C_6$)alkyl, substituted ($C_1$-$C_6$)alkyl, ($C_1$-$C_6$)alkenyl, substituted ($C_1$-$C_6$)alkenyl, ($C_1$-$C_6$)alkynyl, substituted ($C_1$-$C_6$)alkynyl, hetero-($C_1$-$C_5$)alkyl, substituted hetero-($C_1$-$C_5$)alkyl, hetero-($C_1$-$C_5$)alkenyl, substituted hetero-($C_1$-$C_5$)alkenyl, hetero-($C_1$-$C_5$)alkynyl, substituted hetero-($C_1$-$C_5$)alkynyl, ($C_1$-$C_8$)cycloalkyl, substituted ($C_1$-$C_8$) cycloalkyl, aryl, substituted aryl, heterocycle, and substituted heterocycle;

with the proviso that an A may not exceed its maximum valence by binding a R; and with the proviso that an X may not exceed its maximum valence by binding a Y.

In one embodiment, the linking moiety of the COF comprises an organic-based parent chain comprising alkyl, hetero-alkyl, alkenyl, hetero-alkenyl, alkynyl, hetero-alkynyl, one or more cycloalkyl rings, one or more cycloalkenyl rings, one or more cycloalkynyl rings, one of more aryl rings, one or more heterocycle rings, or any combination of the preceding groups, including larger ring structures composed of linked and/or fused ring systems of different types of rings; wherein this organic-based parent chain may be further substituted with one or more functional groups, including additional substituted or unsubstituted hydrocarbons and heterocycle groups, or a combination thereof; and wherein the linking moiety contains at least one (e.g. 1, 2, 3, 4, 5, 6, . . . ) linking cluster.

In yet a further embodiment, the linking moiety of the COF has an organic-based parent chain that is comprised of one or more substituted or unsubstituted rings; wherein one or more of these rings is further substituted with one or more functional groups, including additional substituted or unsubstituted hydrocarbons and heterocycle groups, or a combination thereof; and wherein the linking moiety contains at least one (e.g. 1, 2, 3, 4, 5, 6, . . . ) linking cluster.

In yet a further embodiment, the linking moiety of the COF has an organic-based parent chain that is comprised of one or more substituted or unsubstituted rings; wherein one or more of these rings are further substituted with one or more functional groups, including additional substituted or unsubstituted hydrocarbons and heterocycle groups, or a combination thereof; and wherein the linking moiety contains at least one (e.g. 1, 2, 3, 4, 5, 6, . . . ) linking cluster that is either a carboxylic acid, ester, aldehyde, amine, thiol, cyano, nitro, hydroxyl, or heterocycle ring heteroatom, such as the N in pyridine.

In another embodiment, the linking moiety of the COF has an organic-based parent chain that is comprised of one or more substituted or unsubstituted rings; wherein one or more of these rings are further substituted with one or more functional groups, including additional substituted or unsubstituted hydrocarbons and heterocycle groups, or a combination thereof; and wherein the linking moiety contains at least one (e.g. 1, 2, 3, 4, 5, 6, . . . ) linking cluster that is either a carboxylic acid, ester, aldehyde, amine, or hydroxyl.

In another embodiment, the linking moiety of the COF has an organic-based parent chain that is comprised of one or more substituted or unsubstituted rings; wherein one or more of these rings are further substituted with one or more functional groups, including additional substituted or unsubstituted hydrocarbons and heterocycle groups, or a combination thereof; and wherein the linking moiety contains at least one (e.g. 1, 2, 3, 4, 5, 6, . . . ) aldehyde or hydroxyl linking cluster.

In another embodiment, the linking moiety of the COF has an organic-based parent chain that is comprised of one or more substituted or unsubstituted rings; wherein one or more of these rings are further substituted with two or more functional groups, including additional substituted or unsubstituted hydrocarbon and heterocycle groups, or a combination thereof; and wherein the linking moiety contains at least two (e.g. 2, 3, 4, 5, 6, . . . ) aldehyde or hydroxyl linking clusters.

In yet another embodiment, the linking moiety of the COF has an organic-based parent chain that is comprised of one or more substituted or unsubstituted rings; wherein one or more of these rings are further substituted with two or more functional groups, including additional substituted or unsubstituted hydrocarbon and heterocycle groups, or a combination thereof; and wherein the linking moiety contains at least four (e.g. 4, 5, 6, . . . ) hydroxyl clusters.

In a certain embodiment, the COF is generated from one or more linking moieties comprising structures of Formula II, III, IV, V, VII, VIII, IX, and X:

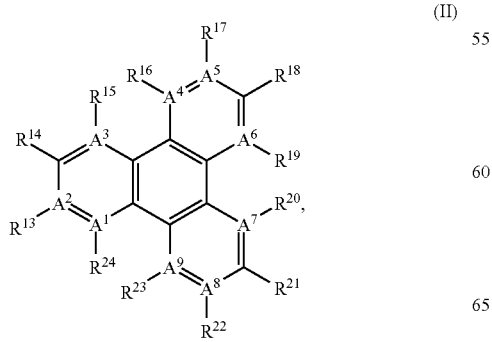
(II)

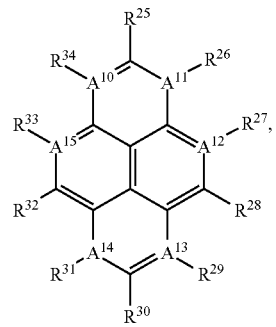
(III)

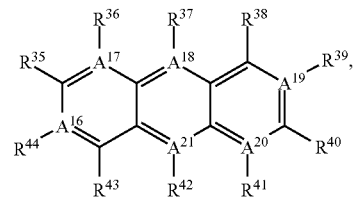
(IV)

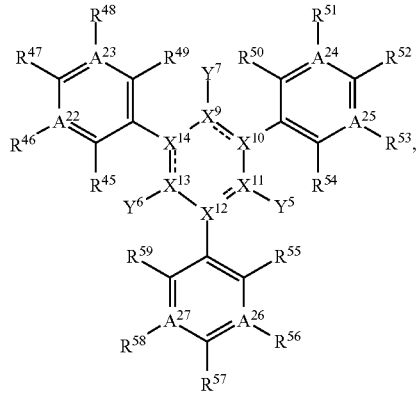
(V)

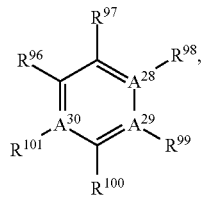
(VII)

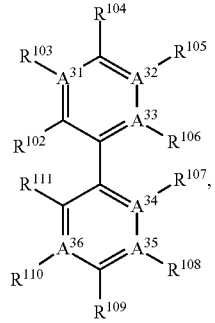
(VIII)

-continued

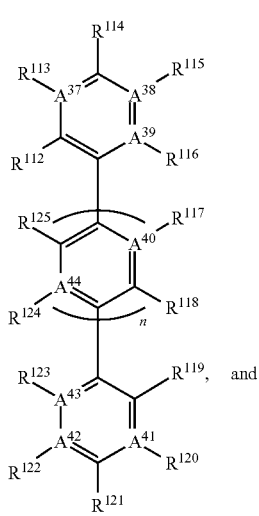

(IX)

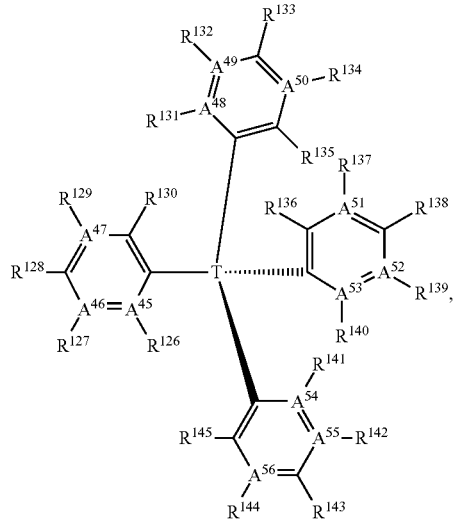

(X)

wherein:
$A^1$-$A^{56}$ are independently selected from the group comprising C, Si, N and P;
n is a number from 1 to 8;
T is an atom that can assume tetrahedral molecular geometry (e.g., carbon, silicon, germanium, tin), a tetrahedral group, or a tetrahedral cluster;
$R^{13}$-$R^{145}$ are independently selected from the group comprising H, D, FG, ($C_1$-$C_{20}$)alkyl, substituted ($C_1$-$C_{20}$)alkyl, ($C_1$-$C_{20}$)alkenyl, substituted ($C_1$-$C_{20}$)alkenyl, ($C_1$-$C_{20}$)alkynyl, substituted ($C_1$-$C_{20}$)alkynyl, hetero-($C_1$-$C_{20}$)alkyl, substituted hetero-($C_1$-$C_{20}$)alkyl, hetero-($C_1$-$C_{20}$)alkenyl, substituted hetero-($C_1$-$C_{20}$)alkenyl, hetero-($C_1$-$C_{20}$)alkynyl, substituted hetero-($C_1$-$C_{20}$)alkynyl, ($C_1$-$C_{20}$)cycloalkyl, substituted ($C_1$-$C_{20}$)cycloalkyl, aryl, substituted aryl, heterocycle, and substituted heterocycle;
$X^9$-$X^{14}$ are independently selected from the group comprising carbon, oxygen, sulfur, silicon, phosphorous, and nitrogen;
$Y^5$-$Y^7$ are independently selected from the group comprising H, D, and FG;
with the proviso that a X may not exceed its maximum valence by binding a Y; and
with the proviso that an A may not exceed its maximum valence by binding a R.

In yet a further embodiment, a linking moiety capable of linking a one or more cores disclosed herein comprises a compound having structural Formula (IV):

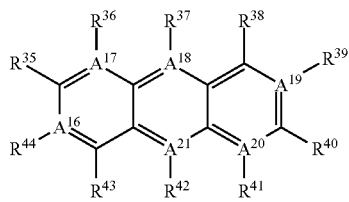

(IV)

wherein,
$A^{16}$-$A^{21}$ are C;
$R^{36}$-$R^{48}$, $R^{41}$-$R^{43}$ are H; and
$R^{35}$, $R^{44}$, $R^{39}$-$R^{40}$ are FG.

In a further embodiment, a linking moiety of Formula (IV) capable of linking a one or more cores disclosed herein is a compound selected from the group comprising:

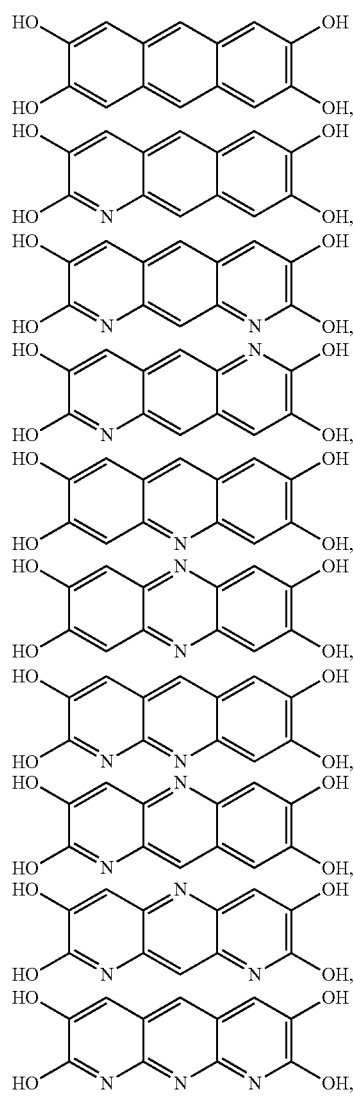

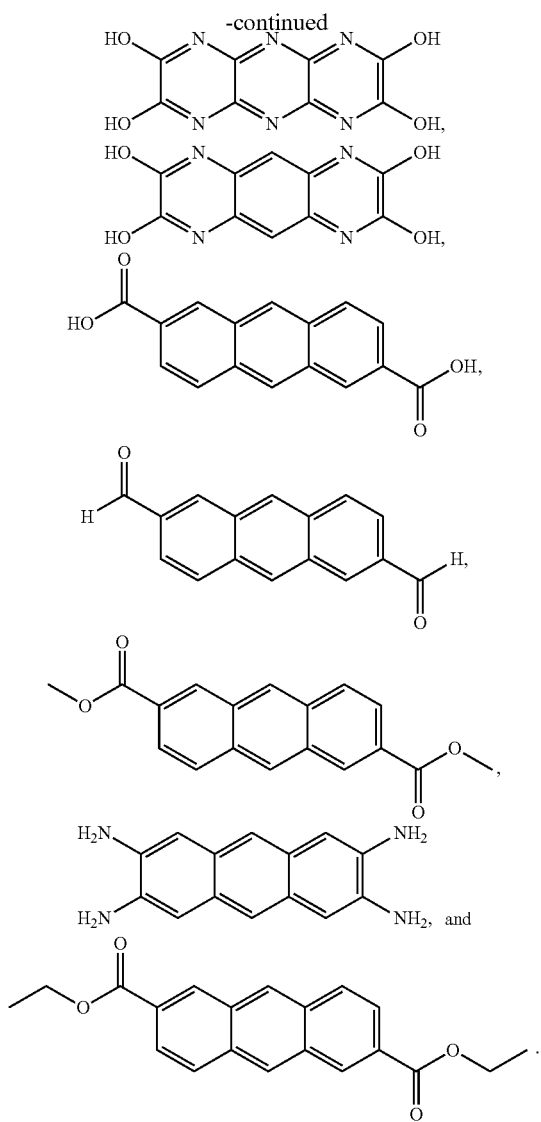

In another embodiment, a linking moiety capable of linking a one or more cores disclosed herein comprises a compound having structural Formula (VII):

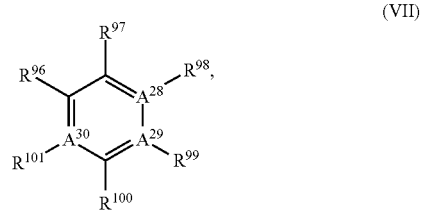

wherein, $A^{28}$-$A^{30}$ are independently either C or N;

$R^{96}$-$R^{101}$ are independently selected from the group comprising H, D, FG, $(C_1$-$C_6)$alkyl, substituted $(C_1$-$C_6)$alkyl, $(C_1$-$C_6)$alkenyl, substituted $(C_1$-$C_6)$alkenyl, $(C_1$-$C_6)$alkynyl, substituted $(C_1$-$C_6)$alkynyl, hetero-$(C_1$-$C_5)$alkyl, substituted hetero-$(C_1$-$C_5)$alkyl, hetero-$(C_1$-$C_5)$alkenyl, substituted hetero-$(C_1$-$C_5)$alkenyl, hetero-$(C_1$-$C_6)$alkynyl, substituted hetero-$(C_1$-$C_5)$alkynyl, $(C_1$-$C_8)$cycloalkyl, substituted $(C_1$-$C_8)$cycloalkyl, aryl, substituted aryl, heterocycle, and substituted heterocycle; and with the proviso that an A may not exceed its maximum valence by binding a R.

In a further embodiment, a linking moiety capable of linking a one or more cores disclosed herein comprises a compound having structural Formula (VII):

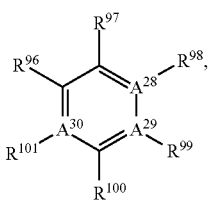

wherein, $A^{28}$-$A^{30}$ are C;

$R^{96}$, $R^{98}$-$R^{99}$, $R^{101}$ are independently either an H or D; and $R^{97}$ and $R^{100}$ are FG.

In a further embodiment, a linking moiety of Formula (VII) capable of linking a one or more cores disclosed herein is a compound selected from the group comprising:

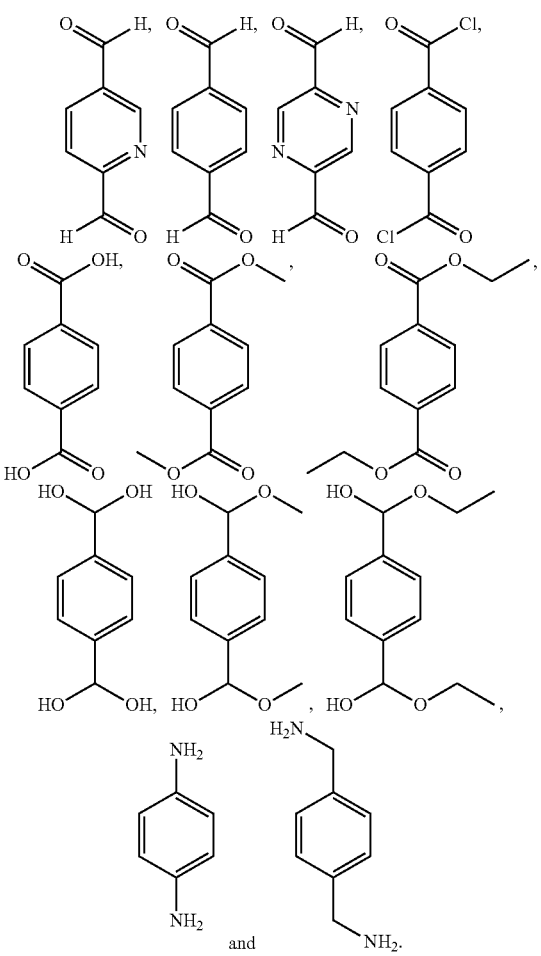

In another embodiment, a linking moiety capable of linking a one or more cores disclosed herein comprises a compound having structural Formula (VIII):

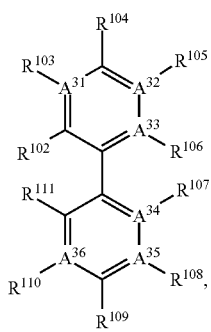

(VIII)

wherein, $A^{31}$-$A^{36}$ are independently either C or N;

$R^{102}$-$R^{111}$ are independently selected from the group comprising H, D, FG, $(C_1$-$C_6)$alkyl, substituted $(C_1$-$C_6)$alkyl, $(C_1$-$C_6)$alkenyl, substituted $(C_1$-$C_6)$alkenyl, $(C_1$-$C_6)$alkynyl, substituted $(C_1$-$C_6)$alkynyl, hetero-$(C_1$-$C_5)$alkyl, substituted hetero-$(C_1$-$C_5)$alkyl, hetero-$(C_1$-$C_5)$alkenyl, substituted hetero-$(C_1$-$C_5)$alkenyl, hetero-$(C_1$-$C_5)$alkynyl, substituted hetero-$(C_1$-$C_5)$alkynyl, $(C_1$-$C_8)$cycloalkyl, substituted $(C_1$-$C_8)$cycloalkyl, aryl, substituted aryl, heterocycle, and substituted heterocycle; and with the proviso that an A may not exceed its maximum valence by binding a R.

In another embodiment, a linking moiety capable of linking a one or more cores disclosed herein comprises a compound having structural Formula (IX):

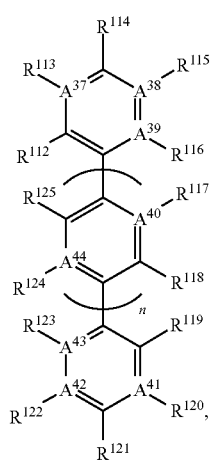

(IX)

wherein, n is a number from 1 to 8;

$A^{37}$-$A^{44}$ are independently either C or N;

$R^{112}$-$R^{125}$ are independently selected from the group comprising H, D, FG, $(C_1$-$C_6)$alkyl, substituted $(C_1$-$C_6)$alkyl, $(C_1$-$C_6)$alkenyl, substituted $(C_1$-$C_6)$alkenyl, $(C_1$-$C_6)$alkynyl, substituted $(C_1$-$C_6)$alkynyl, hetero-$(C_1$-$C_5)$alkyl, substituted hetero-$(C_1$-$C_5)$alkyl, hetero-$(C_1$-$C_5)$alkenyl, substituted hetero-$(C_1$-$C_5)$alkenyl, hetero-$(C_1$-$C_5)$alkynyl, substituted hetero-$(C_1$-$C_5)$alkynyl, $(C_1$-$C_8)$cycloalkyl, substituted $(C_1$-$C_8)$ cycloalkyl, aryl, substituted aryl, heterocycle, and substituted heterocycle; and with the proviso that an A may not exceed its maximum valence by binding a R.

In another embodiment, a linking moiety capable of linking a one or more cores disclosed herein comprises a compound having structural Formula (X):

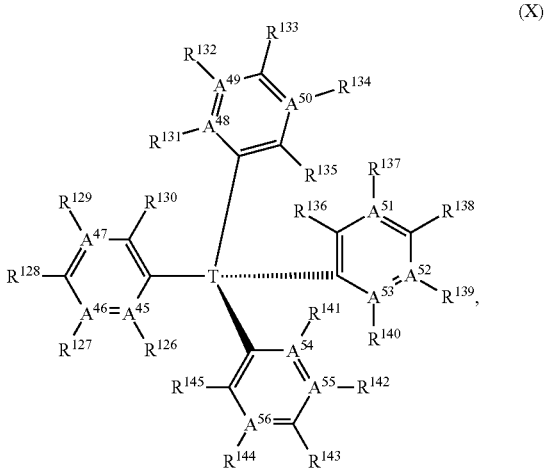

(X)

wherein,

T is either a C, Si, or Ge;

$A^{45}$-$A^{56}$ are independently either C or N;

$R^{126}$-$R^{145}$ are independently selected from the group comprising H, D, FG, $(C_1$-$C_6)$alkyl, substituted $(C_1$-$C_6)$alkyl, $(C_1$-$C_6)$alkenyl, substituted $(C_1$-$C_6)$alkenyl, $(C_1$-$C_6)$alkynyl, substituted $(C_1$-$C_6)$alkynyl, hetero-$(C_1$-$C_5)$alkyl, substituted hetero-$(C_1$-$C_5)$alkyl, hetero-$(C_1$-$C_5)$alkenyl, substituted hetero-$(C_1$-$C_5)$alkenyl, hetero-$(C_1$-$C_5)$alkynyl, substituted hetero-$(C_1$-$C_5)$alkynyl, $(C_1$-$C_8)$cycloalkyl, substituted $(C_1$-$C_8)$ cycloalkyl, aryl, substituted aryl, heterocycle, and substituted heterocycle;

with the proviso that an A may not exceed its maximum valence by binding a R.

The linking moiety may have two or more linking clusters (e.g., three or more linking clusters) to obtain 2D and 3D-frameworks including cages and ring structures.

The disclosure provides a COF comprising two or more cores covalently bonded to one or more linking moieties through one or more linking clusters. In a certain embodiment, one or more linking clusters contain one or more atoms selected from the group comprising carbon, boron, oxygen, nitrogen and phosphorus. In another embodiment one or more linking clusters contain oxygen or nitrogen.

In a further embodiment, a core and/or linking moiety contains at least one boron-containing linking cluster. In another embodiment, a core and/or linking moiety contains a boron-containing linking cluster which forms a covalent bond with a boron-lacking linking cluster. In a further embodiment, a core and/or linking moiety contains a boron-containing linking cluster which forms a covalent bond with a boron-lacking linking cluster through a condensation reaction.

In a certain embodiment, a core and/or linking moiety disclosed herein has at least one (e.g. 1, 2, 3, 4, 5, 6, . . . ) linking cluster with the formula

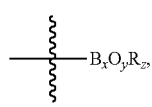

wherein x is number from 1 to 2, y is a number from 1 to 8, z is a number from 1 to 8, and R is a H, D, or FG. In another embodiment, a core is linked to one or more linking moieties by at least 2, at least 3 or at least 4 boron containing linking clusters. In a further embodiment, the boron-containing linking cluster comprises at least 2 or at least 4 oxygens capable of forming a link. For example, a boron-containing linking cluster disclosed herein comprises Formula (VI):

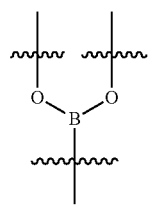

(VI)

The COFs of the disclosure may optionally further comprise a guest species. Such a guest species may increase the surface area of the covalently linked organic networks. In a similar manner, the covalently linked organic networks of the disclosure further comprise an adsorbed chemical species. Such adsorbed chemical species include for example, ammonia, carbon dioxide, carbon monoxide, hydrogen, amines, methane, oxygen, argon, nitrogen, organic dyes, polycyclic organic molecules, metal ions, inorganic clusters, organometallic clusters, and combinations thereof.

A method for forming COFs of the disclosure is provided by the following schemes, reactions, and working Examples. Moreover, the schemes, reactions and working Examples provided herein, while setting forth exemplified methods to make and/or synthesize the COFs of the disclosure, these schemes, reactions and working Examples are not presented as the definitive methods to make the COFs of the disclosure. The disclosure encompasses obvious variations of the synthesis reactions, schemes, and/or working Examples presented herein, including but not limited to, varying the reaction conditions (e.g. adding, removing, and/or modifying heating and/or cooling steps, adding, removing, and/or modifying distillation steps, adding, removing, and/or modifying the atmosphere of one or more reactions, using or not using molecular sieves, etc.); removing, adding, or substituting solvents; adding or replacing catalysts; changing and/or modifying linking cluster functional groups (e.g. converting a functional group to a different functional group, modifying an existing functional group to make it more reactive, modifying an existing functional group so as to make it reactive under certain reaction conditions); protecting and de-protecting functional groups of the cores and/or linking moieties; and adding, replacing, or removing purification steps.

Generally, depending on the composition of the linking clusters, various reaction mechanisms can be utilized to form one or more covalent bonds between one or more cores and one or more linking moieties. Examples of such reaction mechanisms include, but are not limited to, condensation, radical, $S_N^1$, $S_N^2$, $S_N^{Ar}$, E1, E2, E1$_{cB}$ elimination, pericyclic, electrocylic, sigmatropic rearrangements, cycloaddition, and electrophilic aromatic substitution.

Moreover, by taking advantage of linking clusters that react differently under the same conditions or alternatively under different conditions, one can tailor COFs so as to directionally, or not directionally, covalently bond one or more cores with one or more linking moieties so as to form heterogeneous nets. For example, a core which has linking clusters with different reactivities can react with different linking clusters from a linking moiety in a predictive manner. The reactivities of such linking clusters can vary not only based on composition, but also based on steric effects, electronic effects, neighboring atom effects, and/or a combination thereof.

Typically, but not exclusively, one or more covalent bonds are formed between one or more cores and one or more linking moieties by using condensation reactions, for example, enamine formation, imine formation, Claisen condensation, aldol condensation, Knoevenagel condensation, and boronic acid-based condensation reactions. Additionally, typical reactions that can be used to form one or more covalent bonds between one or more cores and one or more linking moieties include, but are not limited to, Suzuki couplings, Chan-Lam couplings, Liebeskind-Srogl couplings, general $S_N^1$-based reactions, general $S_N^2$-based reactions, olefin metathesis, and conjugate addition based reactions.

The preparation of the frameworks of the disclosure can be carried out in either an aqueous or non-aqueous solvent system. The solvent may be polar or non-polar, or a combination thereof, as the case may be. The reaction mixture or suspension comprises a solvent system, linking moieties, and cores. The reaction solution, mixture or suspension may further contain a catalyst. The reaction mixture may be heated at an elevated temperature or maintained at ambient temperature, depending on the reaction components.

Examples of non-aqueous solvents that can be used in the reaction to make the framework and/or used as non-aqueous solvent for a post synthesized framework reaction, include, but is not limited to: n-hydrocarbon based solvents, such as pentane, hexane, octadecane, and dodecane; branched and cyclo-hydrocarbon based solvents, such as cycloheptane, cyclohexane, methyl cyclohexane, cyclohexene, cyclopentane; aryl and substituted aryl based solvents, such as benzene, toluene, xylene, chlorobenzene, nitrobenzene, cyanobenzene, naphthalene, and aniline; mixed hydrocarbon and aryl based solvents, such as, mixed hexanes, mixed pentanes, naptha, and petroleum ether; alcohol based solvents, such as, methanol, ethanol, n-propanol, isopropanol, propylene glycol, 1,3-propanediol, n-butanol, isobutanol, 2-methyl-1-butanol, tert-butanol, 1,4-butanediol, 2-methyl-1-petanol, and 2-pentanol; amide based solvents, such as, dimethylacetamide, dimethylformamide (DMF), formamide, N-methylformamide, N-methylpyrrolidone, and 2-pyrrolidone; amine based solvents, such as, piperidine, pyrrolidine, collidine, pyridine, morpholine, quinoline, ethanolamine, ethylenediamine, and diethylenetriamine; ester based solvents, such as, butylacetate, sec-butyl acetate, tert-butyl acetate, diethyl carbonate, ethyl acetate, ethyl acetoacetate, ethyl lactate, ethylene carbonate, hexyl acetate, isobutyl acetate, isopropyl acetate, methyl acetate, propyl acetate, and propylene carbonate; ether based solvents, such as, di-tert-butyl ether, diethyl ether, diglyme, diisopropyl ether, 1,4-dioxane, 2-methyltetrahydrofuran, tetrahydrofuran (THF), and tetrahydropyran; glycol ether based solvents, such as, 2-butoxyethanol, dimethoxyethane, 2-ethoxyethanol, 2-(2-ethoxyethoxy)ethanol, and 2-methoxyethanol; halogenated based solvents, such as, carbon tetrachloride, cholorbenzene, chloroform, 1,1-dichloroethane, 1,2-dichloroethane, 1,2-dichloroethene, dichloromethane (DCM), diiodomethane, epichlorohydrin, hexachlorobutadiene, hexafluoro-2-propanol, perfluorodecalin, perfluorohexane, tetrabromomethane, 1,1,2,2-tetrachloroethane, tetrachloroethylene, 1,3,5-trichlorobenzene, 1,1,1-trichloroethane, 1,1,2-trichloroethane, trichloroethylene, 1,2,3-trichloropropane, trifluoroacetic acid, and 2,2,2-trifluoroethanol; inorganic based solvents, such as hydrogen chloride, ammonia, carbon disulfide, thionyl chloride, and phosphorous tribromide; ketone based solvents, such as, acetone, butanone, ethylisopropyl ketone, isophorone, methyl isobutyl ketone, methyl isopropyl ketone, and 3-pentanone; nitro and nitrile based solvents, such as, nitroethane, acetonitrile, and nitromethane; sulfur based solvents, dimethyl sulfoxide (DMSO), methylsulfonylmethane, sulfolane, isocyanomethane, thiophene, and thiodiglycol; urea, lactone and carbonate based solvents, such as 1-3-dimethyl-3,4,5,6-tetrahydro-2(1H)-pyrimidinone (DMPU), 1-3-dimethyl-2-imidazolidinone, butyrolactone, cis-2,3-butylene carbonate, trans-2,3-butylene carbonate, 2,3-butylene carbonate; carboxylic acid based solvents, such as formic acid, acetic acid, chloroacetic acid, trichloroacetic acid, trifluoroacetic acid, propanoic acid, butanoic acid, caproic acid, oxalic acid, and benzoic acid; boron and phosphorous based solvents, such as triethyl borate, triethyl phosphate, trimethyl borate, and trimethyl phosphate; deuterium containing solvents, such as deuterated acetone, deuterated benzene, deuterated chloroform, deuterated dichloromethane, deuterated DMF, deuterated DMSO, deuterated ethanol, deuterated methanol, and deuterated THF; and any appropriate mixtures thereof.

In another embodiment, the nonaqueous solvent used as the solvent system in synthesizing the framework has a pH less than 7. In a further embodiment, the solvent system used to synthesize the framework is an aqueous solution that has a pH less than 7. In another embodiment, the nonaqueous solvent used as the solvent system in synthesizing the framework has a pH greater than 7. In a further embodiment, the solvent system used to synthesize the framework is an aqueous solution that has a pH greater than 7. In a further embodiment, the solvent system used to synthesize the framework is an aqueous solution or non aqueous solution that has a neutral pH. In yet a further embodiment, the solvent system used to synthesize the frameworks contains mesitylene. In another embodiment, the solvent system used to synthesize the frameworks contains acetic acid. In a further embodiment, the solvent system used to synthesize the frameworks contains an alcohol.

Those skilled in the art will be readily able to determine an appropriate solvent or appropriate mixture of solvents based on the starting reactants and/or where the choice of a particular solvent(s) is not believed to be crucial in obtaining the materials of the disclosure.

The COF crystalline product may be either polycrystalline or a single crystal. For example, after the chemical reactions a porous, semicrystalline to crystalline organic material with high surface area is produced.

The COFs of the disclosure can assume any framework/structure. For example, using the methods of the disclosure, COFs having any of the following framework type codes can be obtained: ABW ACO AEI AEL AEN AET AFG AFI AFN AFO AFR AFS AFT AFX AFY AHT ANA APC APD AST ASV ATN ATO ATS ATT ATV AWO AWW BCT*BEA BEC BIK BOG BPH BRE CAN CAS CDO CFI CGF CGS CHA CHI CLO CON CZP DAC DDR DFO DFT DOH DON EAB EDI EMT EON EPI ERI ESV ETR EUO EZT FAR FAU FER FRA GIS GIU GME GON GOO HEU IFR IHW ISV ITE ITH ITW IWR IWV IWW JBW KFI LAU LEV LIO LIT LOS LOV LTA LTL LTN MAR MAZ MEI MEL MEP MER MFI MFS MON MOR MOZ MSE MSO MTF MTN MTT MTW MWW NAB NAT NES NON NPO NSI OBW OFF OSI OSO OWE PAR PAU PHI PON RHO RON RRO RSN RTE RTH RUT RWR RWY SAO SAS SAT SAV SBE SBS SBT SFE SFF SFG SFH SFN SFO SGT SIV SOD SOS SSY STF STI STT SZR TER THO TON TSC TUN UEI UFI UOZ USI UTL VET VFI VNI VSV WEI WEN YUG ZON.

In another aspect, the covalent-organic frameworks set forth above may include an interpenetrating covalent-organic framework that increases the surface area of the covalent-organic framework. Although the frameworks of the disclosure may advantageously exclude such interpenetration, there are circumstances when the inclusion of an interpenetrating framework may be used to increase the surface area.

It is further contemplated that a COF of the disclosure may be generated by first utilizing a plurality of linking moieties having different functional groups, wherein at least one of these functional groups may be modified, substituted, or eliminated with a different functional group post-synthesis of the COF. In other words, at least one linking moiety comprises a functional group that may be post-synthesized reacted with a post framework reactant to further increase the diversity of the functional groups of the COF.

After the COFs are synthesized, the COFs may be further modified by reacting with one or more post framework reactants that may or may not have denticity. In a certain embodiment, the COFs as-synthesized are not reacted with a post framework reactant. In another embodiment, the COFs as-synthesized are reacted with at least one post framework reactant. In yet another embodiment, the COFs as-synthesized are reacted with at least two post framework reactants. In a further embodiment, the COFs as-synthesized are reacted with at least one post framework reactant that will result in adding denticity to the framework.

It is contemplated by this disclosure that chemical reactions that modify, substitute, or eliminate a functional group post-synthesis of the framework with post framework reactant may use one or more similar or divergent chemical reaction mechanisms depending on the type of functional group and/or post framework reactant used in the reaction. Examples of chemical reaction mechanisms contemplated by this disclosure include, but is not limited to, condensation, radical, $S_N^1$, $S_N^2$, $S_N^{Ar}$, E1, E2, $E1_{c}B$ elimination, nucleophilic internal substitution ($S_N^i$), pericyclic, electrocylic, sigmatropic rearrangements, cycloaddition, and electrophilic aromatic substitution, electrophilic addition, oxidation, reduction, cycloaditton, ring closing metathesis (RCM), pericylic, electrocylic, rearrangement, carbene, carbenoid, cross coupling, and degradation.

All the aforementioned linking moieties and/or cores that possess appropriate reactive functionalities can be chemically transformed by a suitable reactant post framework synthesis to add further functionalities to the COF. By modifying the organic moieties and/or cores within the COF post-synthesis, access to functional groups that were previously inaccessible or accessible only through great difficulty and/or cost is possible and facile.

It is yet further contemplated by this disclosure that to enhance chemoselectivity it may be desirable to protect one or more functional groups that would generate unfavorable products upon a chemical reaction desired for another functional group, and then deprotect this protected group after the desired reaction is completed. Employing such a protection/deprotection strategy could be used for one or more functional groups.

Other agents can be added to increase the rate of the reactions disclosed herein, including adding catalysts, bases, and acids.

In another embodiment, the post framework reactant is selected to have a property selected from the group comprising, binds a metal ion, increases the hydrophobicity of the framework, modifies the gas sorption of the framework, modifies the pore size of the framework, and tethers a catalyst to the framework.

In one embodiment, the post framework reactant can be a saturated or unsaturated heterocycle.

In another embodiment, the post framework reactant has 1-20 carbons with functional groups including atoms such as N, S, and O.

In yet another embodiment, the post framework reactant is selected to modulate the size of the pores in the framework.

In another embodiment, the post framework reactant is selected to increase the hydrophobicity of the framework.

In yet a further embodiment, the post framework reactant is selected to increase or add catalytic efficiency to the framework.

In yet a further embodiment, the post framework reactant is selected to increase the charge mobility of the framework.

In another embodiment, the post framework reactant is selected to increase the time the framework holds a charge.

In another embodiment, a post framework reactant is selected so that organometallic complexes can be tethered to the framework. Such tethered organometallic complexes can be used, for example, as heterogeneous catalysts In yet another embodiment, the post framework reactant is selected to modulate gas separation of the framework. In a certain embodiment, the post framework reactant creates an electric dipole moment on the surface of the framework when it chelates a metal ion.

In one embodiment of the disclosure, a gas storage material comprising a COF is provided. Advantageously, the COF includes one or more sites for storing gas molecules. Gases that may be stored in the gas storage material of the disclosure include gas molecules comprising available electron density for attachment to the one or more sites on the surface are of a pore or interpenetrating porous network. Such electron density includes molecules having multiple bonds between two atoms contained therein or molecules having a lone pair of electrons. Suitable examples of such gases include, but are not limited to, the gases comprising a component selected from the group comprising ammonia, argon, carbon dioxide, carbon monoxide, hydrogen, and combinations thereof. In a particularly useful variation the gas storage material is a hydrogen storage material that is used to store hydrogen ($H_2$). In another particularly useful variation, the gas storage material is a carbon dioxide storage material that may be used to separate carbon dioxide from a gaseous mixture.

In a variation of this embodiment, the gaseous storage site comprises a pore in a COF. In a refinement, this activation involves removing one or more chemical moieties (guest molecules) from the COF. Typically, such guest molecules include species such as water, solvent molecules contained within the COF, and other chemical moieties having electron density available for attachment.

The COFs provided herein include a plurality of pores for gas adsorption. In one variation, the plurality of pores has a unimodal size distribution. In another variation, the plurality of pores have a multimodal (e.g., bimodal) size distribution.

Sorption is a general term that refers to a process that results in the association of atoms or molecules with a target material. Sorption includes both adsorption and absorption. Absorption refers to a process in which atoms or molecules move into the bulk of a porous material, such as the absorption of water by a sponge. Adsorption refers to a process in which atoms or molecules move from a bulk phase (that is, solid, liquid, or gas) onto a solid or liquid surface. The term adsorption may be used in the context of solid surfaces in contact with liquids and gases. Molecules that have been adsorbed onto solid surfaces are referred to generically as adsorbates, and the surface to which they are adsorbed as the substrate or adsorbent. Adsorption is usually described through isotherms, that is, functions which connect the amount of adsorbate on the adsorbent, with its pressure (if gas) or concentration (if liquid). In general, desorption refers to the reverse of adsorption, and is a process in which molecules adsorbed on a surface are transferred back into a bulk phase.

Although it is known that porous compounds adsorb guest molecules, the mechanism of adsorption is complicated. For the fundamental studies developments of a new class of materials whose structure are well organized are prerequisites, because one needs to consider specific interaction between adsorbent and adsorptive. Recently discovered crystalline porous materials of COFs are good candidates to acquire general knowledge systematically. That is, not only apparent surface area and pore volume but also pore size distribution and adsorption sites needs to be analyzed by use of Ar isotherms.

Two COFs have been examined as standards for Ar storage materials. Since these compounds possess various pore diameters and functionalities, systematic studies on Ar sorption behavior should be possible. Gas sorption isotherms were taken under low pressure region (up to 760 Torr) at 87 K.

These materials would be used as standard compounds for sorption instruments, and obtained results would be helpful to improve various industrial plants (i.e. separation or recovery of chemical substance).

The advantage of COFs over well studied activated carbons is related to the robust porous structures and the ease to functionalize the pore and surface by choosing appropriate organic linkers and/or metal ions. Collected data should be applicable to DFT calculation to estimate pore size distribution, which is attractive method in isotherm analyses.

The ability of gas sorption has been examined by measuring Ar isotherms, and several materials are already synthesized in gram scale order successfully.

These materials and theoretical knowledge should be desired by chemical industry companies who are running gas separation and storage systems.

In one embodiment, the materials provided herein may be used for methane storage and purification of natural gases. The advantage of COFs over well studied activated carbons is related to the robust porous structures and the ease to functionalize the pore and surface by choosing appropriate organic linkers. Improvements in this disclosure are that i) optimized pore size for $CH_4$ sorption has been discovered and ii) functionalized compounds show good sorption capacities. These discoveries will lead COFs to become more selective and more efficient gas sorption and purification adsorbents. The ability of gas sorption has been examined by measuring $CH_4$ isotherms under wide range pressure. Some compound showed high capacity rather than zeolite 13× and MAXSORB (carbon powder) which are widely used as adsorbents or separation agents.

These materials should be desired by companies who wish to have new porous materials for gas storage and separation, because these materials have optimized pore structures and/or functionalized pore systems which are important factors to control affinity with $CH_4$ molecules. Indeed, appropriate affinity between $CH_4$ and adsorbents should be effective for purification of natural gas without poisoning of the materials' surface.

In another embodiment, the materials may be used for gas storage and separation. The advantage of COFs over well studied activated carbons and zeolites is related to the robust porous structures and the ease to functionalize the pore and surface by choosing appropriate organic linkers and/or metal ions. Some improvements in this disclosure are that i) optimized pore size for $CO_2$ sorption has been discovered and ii) functionalized compounds show good sorption capacities. These discoveries will lead COFs to become more selective and more efficient gas sorption and separation adsorbents. Provided herein are porous Covalent Organic Frameworks (COFs) having functionalized pore, high surface area, and high chemical and thermal stability as adsorbents for reversible carbon dioxide storage. Considering that removal of $CO_2$ (i.e. green house gas) is an important issue from the environmental points of view, development of feasible $CO_2$ storage materials is pressing issue.

These materials should be desired by companies who wish to have new porous materials for gas storage and separation, because these materials have optimized pore structures and/or functionalized pore systems which are important factors to control affinity with $CO_2$ molecules. Indeed, appropriate affinity between $CO_2$ and adsorbents should be effective for removal of $CO_2$ without poisoning of the materials' surface.

Provided herein are porous COFs having functionalized pores, high surface area, and high chemical and thermal stability as adsorbents for reversible hydrogen storage. These materials could be widely applicable to store significant amounts of $H_2$ in a safe and practical way.

In another embodiment, the materials may be used in an $H_2$ tank for hydrogen-powered fuel cells.

The advantage of COFs over well studied activated carbons is related to the robust porous structures and the ease to functionalize the pore and surface by choosing appropriate organic linkers and/or metal ions. Aspects of this disclosure are that i) optimized pore size for $H_2$ sorption has been discovered and ii) functionalized compounds show good sorption capacities. These discoveries will lead COFs to become more selective and more efficient $H_2$ storage materials.

These materials should be desired by car companies who wish to have new porous materials for $H_2$-powered fuel cells.

The disclosure also provides chemical sensors (e.g. resistometric sensors) capable of sensing the presence of an analyte of interest. There is considerable interest in developing sensors that act as analogs of the mammalian olfactory system. However, sensor systems are easily contaminated. The porous structures of the disclosure provide a defined interaction area that limits contamination. For example, various polymers are used in sensor systems including conductive polymers (e.g., poly(anilines) and polythiophenes), composites of conductive polymers and non-conductive polymers and composites of conductive materials and non-conductive materials. In resistometric systems conductive leads are separated by the conductive material such that a current traverse between the leads and through the sensor material. Upon binding to an analyte, the resistance in the material changes and detectable signal is thus generated. Using the COFs of the disclosure, the area surrounding the sensor material is limited and serves as a "filter" to limit contaminants from contacting the sensor material, thus increasing sensor specificity.

In yet another embodiment, the disclosure provides electrical devices comprising COFs of the disclosure for use in displays and screens as well as other components.

The following non-limiting examples illustrate the various embodiments provided herein. Those skilled in the art will recognize many variations that are within the spirit of the subject matter provided herein and scope of the claims.

EXAMPLES

Synthesis Reactions and Associated Schemes

All reactions were performed under argon using either glovebox or Schlenk line techniques. Acetone (99.8%, extra dry) was purchased from Acros Chemicals. Mesitylene (98%) was purchased from Fluka and was not dried prior to use. Tetrahydrofuran (HPLC grade, Aldrich) was passed through a MBraun Solvent Purification System before use (Alumina and Molecular sieves columns). Deuterated solvents (Cambridge Isotope Laboratories) for nuclear magnetic resonance (NMR) spectroscopic analyses were used as received. All other starting materials and solvents, unless otherwise specified, were obtained from Aldrich Chemical Co. and used without further purification. Analytical thin-layer chromatography (TLC) was performed on glass plates, precoated with silica gel 60-$F_{254}$ (Merck 5554). Tetra(p-amino-phenyl) porphyrin (TAPP) and 2,3,4,5-tetrahydroxyanthrancene (THAn) were synthesized using published procedures. Pyrex glass tube charged with reagents and flash frozen with liquid $N_2$ were evacuated using a Schlenk line by fitting the open end of the tube inside a short length of standard rubber hose that was further affixed to a ground glass tap which could be close to insulate this assembly from dynamic vacuum when the desired internal pressure was reached. Tubes were sealed under the desired static vacuum using an oxygen-propane torch. $^1H$ and $^{13}C$ NMR spectra were recorded on a Bruker Avance 500 MHz spectrometer at ambient temperature, unless otherwise noted. The chemical shifts are reported in ppm relative to the signals corresponding to the residual non-deuterated solvents ($CDCl_3$: δ 7.26 ppm, DMSO-$d_6$: δ 2.50 ppm). High-resolution electrospray ionization mass spectra (HRMS-ESI) were measured on a Micromass Q-TOF Ultima mass spectrometer. The reported molecular mass (m/z) values were the most abundant monoisotopic mass. Fourier transform infrared (FT-IR) spectra (4000-400 $cm^{-1}$) were obtained from KBr pellets using a Shimadzu IRAffinity-1 FT-IR system.

Scheme I demonstrates the synthesis of 5,10,15,20-tetrakis-[4-(4,4,5,5-tetramethyl-[1,3,2]dioxaborolan-2-yl)-phenyl]-porphyrin (Intermediate 1).

Scheme I

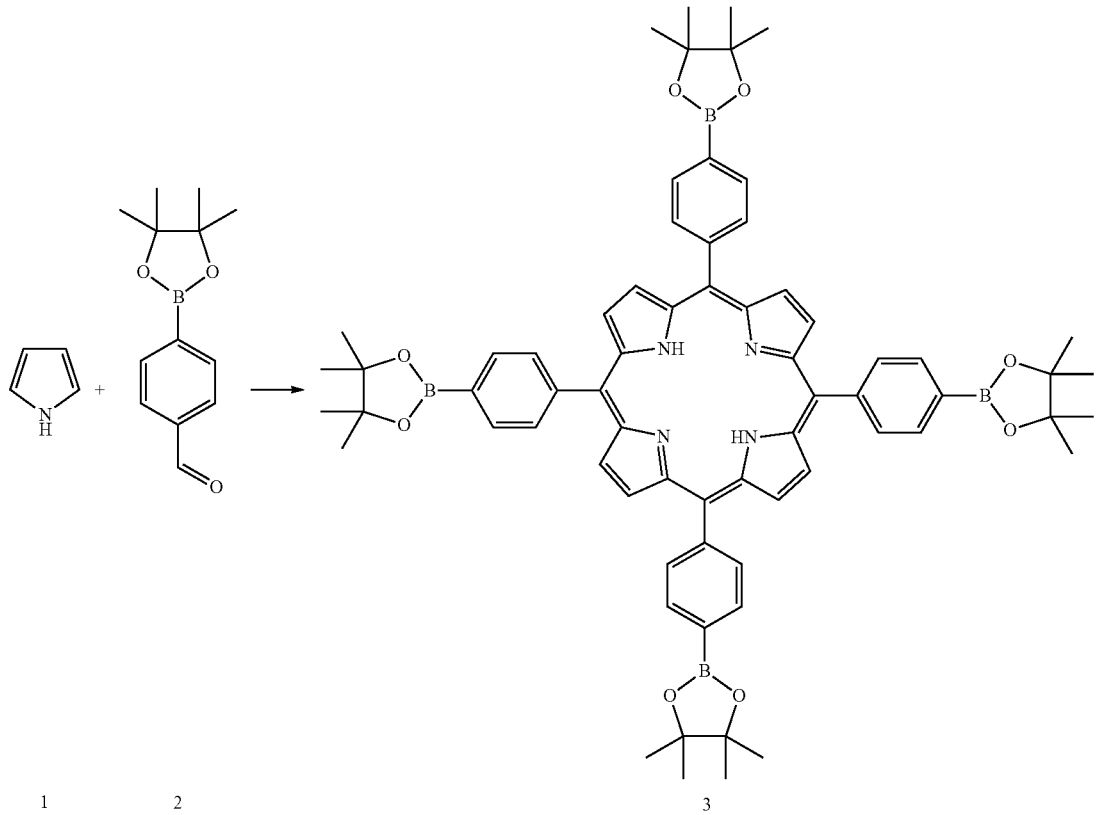

1    2    3

5,10,15,20-Tetrakis-[4-(4,4,5,5-tetramethyl-[1,3,2]dioxaborolan-2-yl)-phenyl]-porphyrin (Intermediate 1) 3: Under an atmosphere of Argon, $BF_3 \cdot Et_2O$ (1.0 mL) was added to a solution of pyrrole 1 (1.8 mL, 26.0 mmol) and aldehyde 2 (6.0 g, 26.0 mmol) dissolved in chloroform (900 mL). After stirring for 2 h at ambient temperature, p-chloranil (10.5 g, 42 mmol) was added. The mixture was stirred at ambient temperature for 1 hour, and then triethylamine (2 mL) was added to quench $BF_3 \cdot Et_2O$. The mixture was passed through a bed of silica on a sintered Büchner funnel, and then washed with chloroform until the filtrate appeared colorless. After the filtrate was concentrated in vacuo, the resulting crude solid was triturated with excess methanol, filtered, and washed thoroughly with methanol (500 mL) to afford compound 3 as a purple solid (3.8 g, yield=13%) $^1H$ NMR (500 MHz, $CD_2Cl_2$, 298K): δ 8.85 (s, 8H, pyrrole-H), 8.23 (AB q, $J_{AB}$=8.0 Hz, 10.0 Hz, 16H, Ar—H), 1.53 (s, 48H, Me—H). $^{13}C$ NMR (125 MHz, $CD_2Cl_2$, 298 K): δ 145.08, 135.11, 133.03, 120.12, 84.14, 177.25, 25.08. HRMS-ESI: Calculated for $C_{68}H_{74}B_4N_4O_8$ [M+H]$^+$ m/z=1119.5957. found m/z=1119.6047.

Scheme II demonstrates the synthesis of tetra(p-boronic acid-phenyl)porphyrin (TBPP), a core of the disclosure.

Scheme II

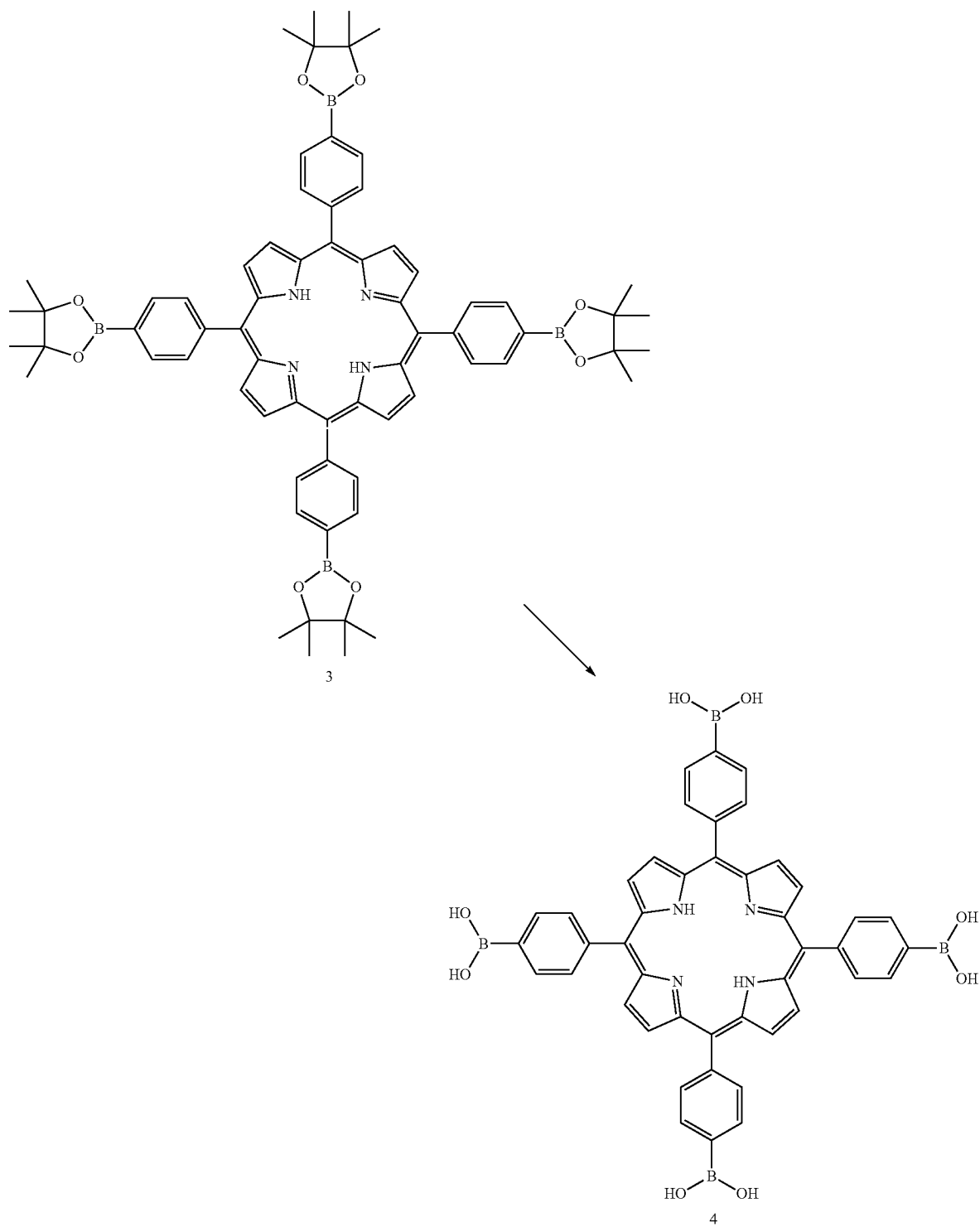

Tetra(p-boronic acid-phenyl)porphyrin (TBPP) 4: Sodium periodate (6.0 g) was added to a solution of 3 (2.5 g, 2.2 mmol) in THF/H$_2$O (4:1) (100 mL). After stirring the solution at 60° C. for 30 mL, 1M HCl (20 mL) was added. The mixture was stirred at ambient temperature for about 16 hours. The solvent was removed in vacuo. The resulting crude solid was resuspended in water, filtered, and washed thoroughly with water (200 mL). The crude solid was then washed with chloroform (300 mL) to dissolve unreacted 3 and partially deprotected products to obtain substantially pure 4 as a dark purple solid (830 mg, 47%) $^1$H NMR (500 MHz, DMSO-d$_6$, 298 K): δ PPM 8.21 (AB q, 16H, J$_{AB}$=7.7 Hz, 11.0 Hz, Ar—H) 8.39

(brs, 8H, B—OH), 8.83 (s, 8H, pyrrole-H), −2.70 (s, 2H, pyrrole-N—H). $^{13}$C NMR (125 MHz, DMSO-$d_6$, 298 K): δ 148.05, 139.40, 138.50, 125.40, 82.10. HRMS-ESI: Calculated for $C_{44}H_{35}B_4N_4O_8$ [M+H]$^+$ m/z=791.2827. found m/z=791.2867.

COFs of the disclosure were synthesized by solvothermal reactions. In the case of COF-366, the formation of the imine bond between the porphyrin and the terephthaldehyde was confirmed by FT-IR spectroscopy and $^{13}$C cross-polarization with magic-angle spinning (CP-MAS) NMR spectroscopic techniques. The FT-IR spectrum clearly reveals the C=N stretching of imine species ($v_{C=N}$=1620 and 1249 cm$^{-1}$), while the $^{13}$C CP-MAS NMR spectrum has a resonance at 156.95 ppm for the carbon of C=N bond.

Scheme III presents the synthesis of two COFs of the disclosure (COF-366 and COF-66).

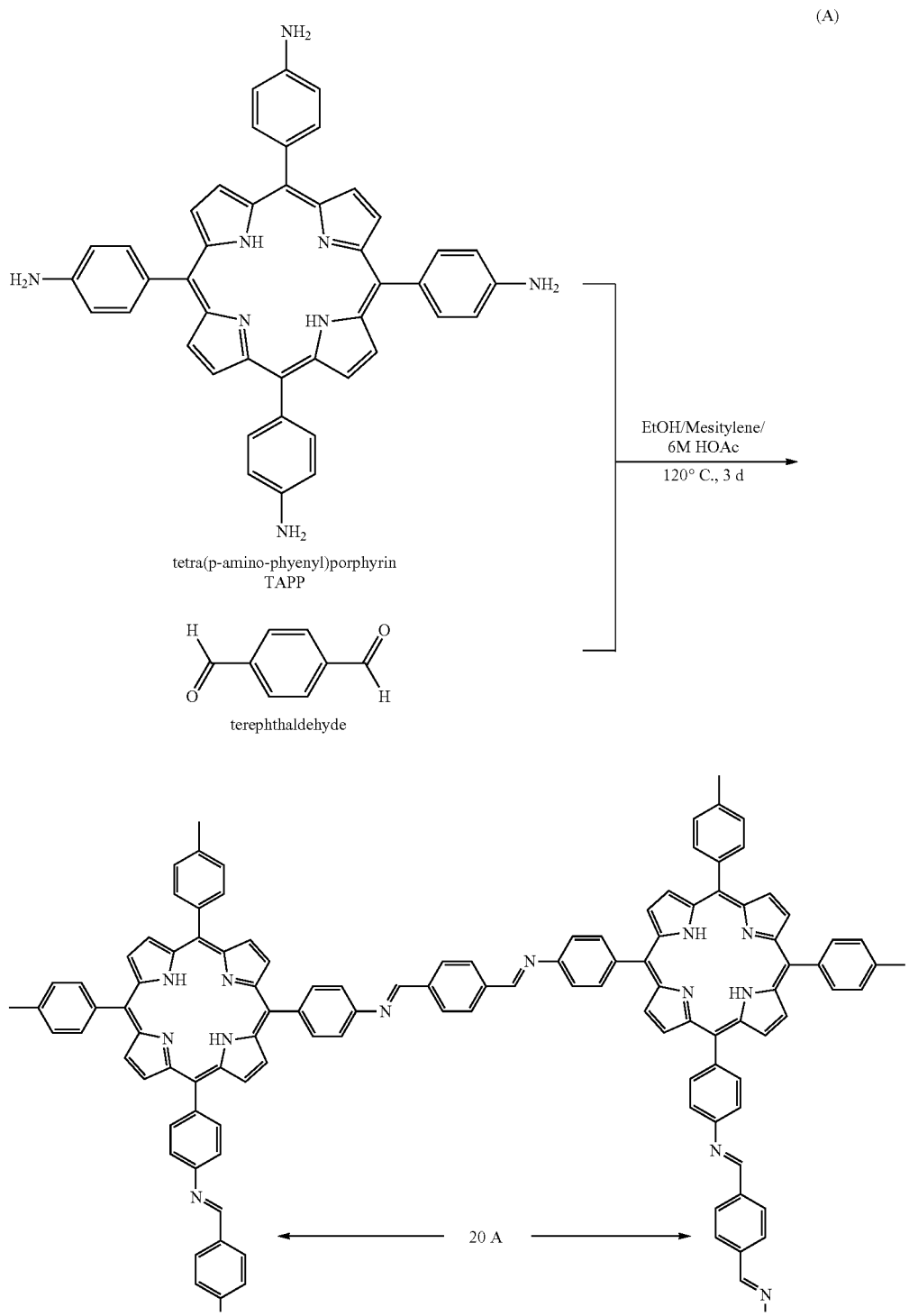

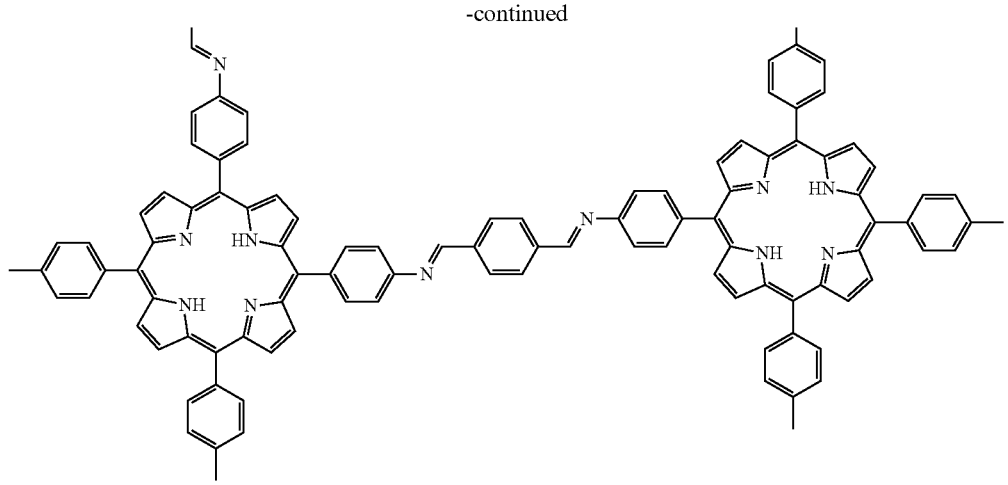
COF-366
C$_{60}$H$_{38}$N$_8$
(B)
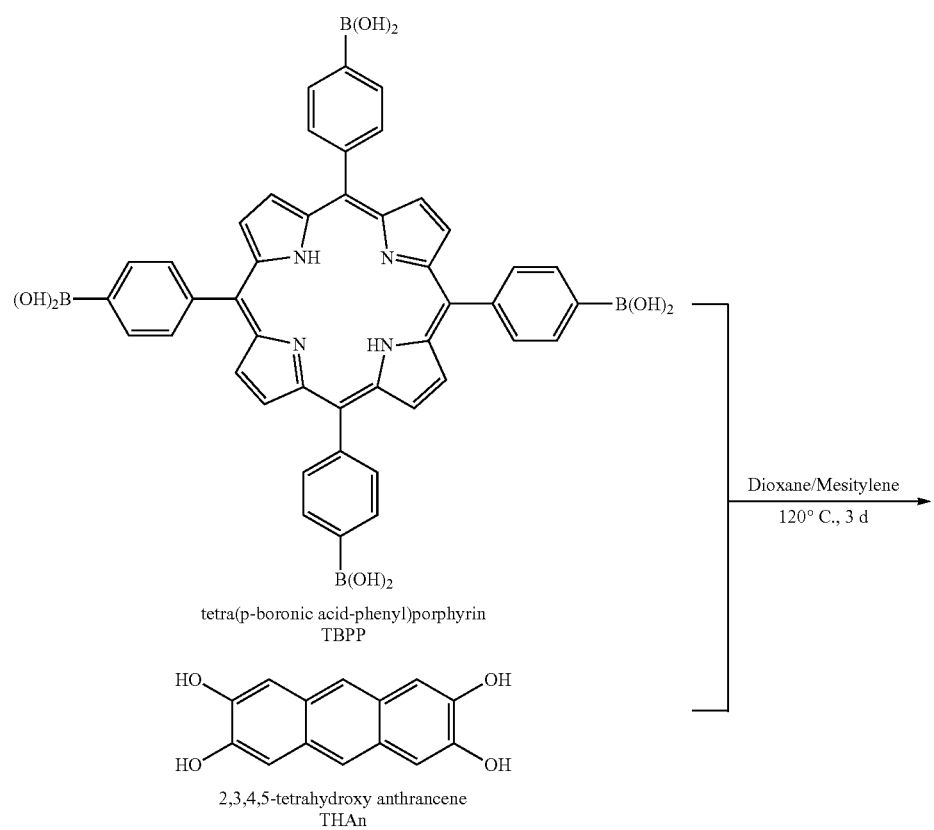
tetra(p-boronic acid-phenyl)porphyrin
TBPP
2,3,4,5-tetrahydroxy anthrancene
THAn
Dioxane/Mesitylene
120° C., 3 d

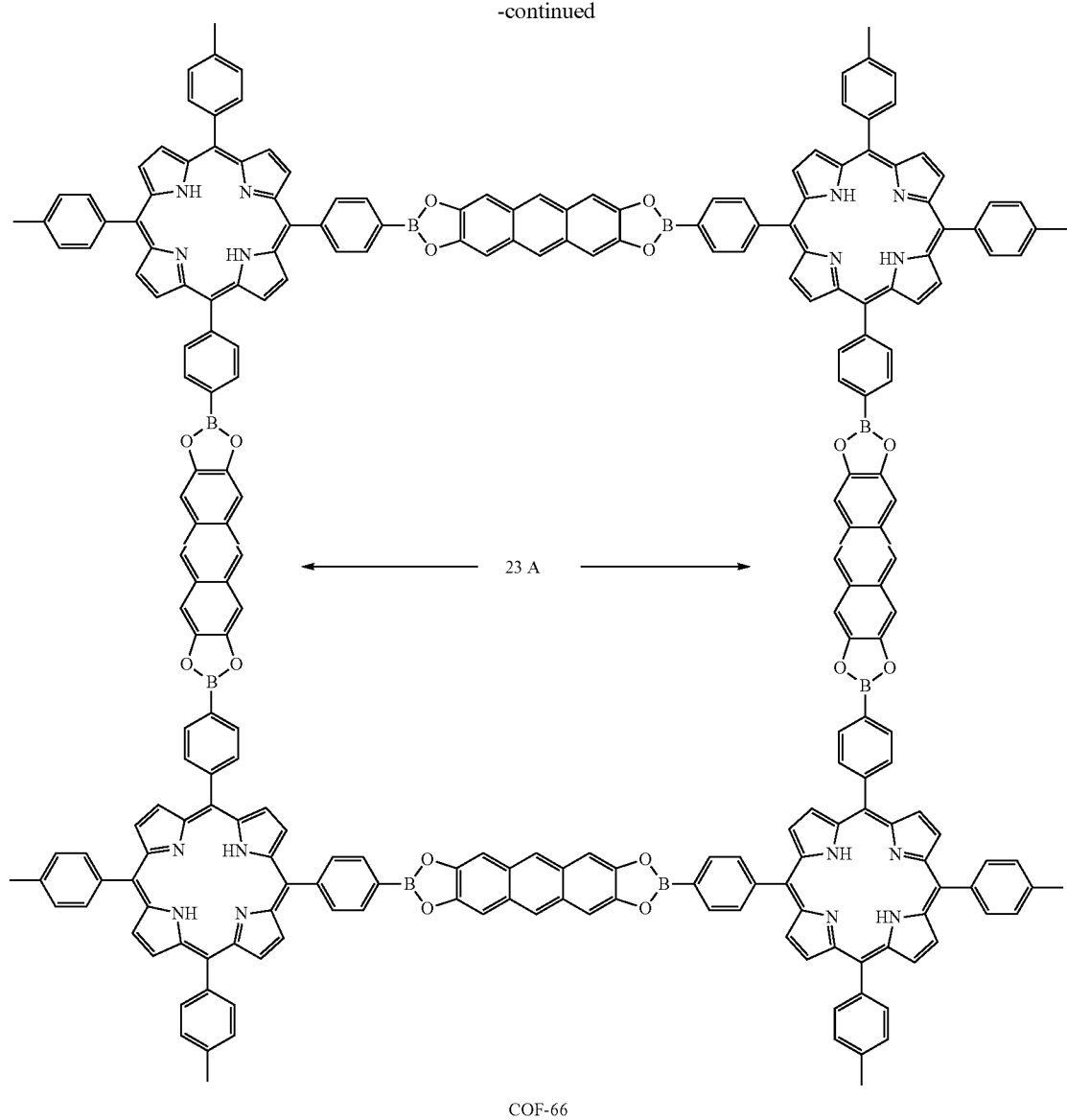

COF-66
C$_{72}$H$_{42}$B$_4$N$_4$O$_8$

COF-366:

A Pyrex tube was charged with terephthaldehyde (5.6 mg, 0.04 mmol), tetra(p-amino-phenyl)porphyrin (TAPP) (13.5 mg, 0.02 mmol), 0.5 mL of ethanol, 0.5 mL of mesitylene, and 0.1 mL of 6 M aqueous acetic acid. The tube was flash frozen at 77 K (liquid N$_2$ bath), evacuated to an internal pressure of 150 mTorr and then flame sealed. The reaction was heated at 120° C. for 72 h. The resulting purple solid was isolated by centrifugation, and washed with 1,4-dioxane, tetrahydrofuran, and acetone. The purple solid was dried at ambient temperature at $10^{-2}$ mTorr for 12 h to afford the title product as a powder (14 mg; yield=79%) IR (KBr, cm$^{-1}$) 3426 (br), 1620 (s), 1512 (m), 1466 (m), 1420 (w), 1381 (m), 1288 (m), 1249 (m), 1180 (s), 1118 (w), 802 (s), 733 (w), 656 (w), 556 (w).

COF-66:

A mixture of tetra(p-boronic acid-phenyl) porphyrin (TBPP) (15.8 mg, 0.02 mmol) and 2,3,4,5-tetrahydroxyanthracene (THAn) (10.0 mg, 0.04 mmol) in a mixture of 0.5 mL dioxane and 0.5 mL mesitylene was heated at 120° C. for 72 h. The resulting solid was collected by centrifugation, washed with anhydrous dioxane, and anhydrous acetone. The solid was then dried at ambient temperature at $10^{-2}$ mTorr for 12 h to afford the title product as a greenish purple powder. (14 mg; yield=72%) IR (KBr, cm$^{-1}$) 3425 (br), 1651 (m), 1604 (s), 1596 (m), 1536 (w), 1495 (m), 1458 (m), 1342 (vs), 1234 (vs), 1164 (s), 980 (w), 863 (m), 832 (w), 710 (w), 644 (w).

Powder X-Ray Diffraction Analyses:

Powder X-ray diffraction data were collected using a Bruker D8-advance θ-2θ diffractometer in reflectance Bragg-Brentano geometry employing θ-2θ filtered Cu Kα line focused radiation at 1600 W (40 kV, 40 mA) power and equipped with a position sensitive detector (PSD) with an electronic window of 6°. Samples were mounted on zero background sample holders by dropping powders from a wide-blade spatula and then leveling the sample surface with a razor blade. Given that the particle size of the 'as synthesized' samples were already found to be quite monodisperse no sample grinding or sieving was used prior to analysis. The best counting statistics were achieved by collecting samples using a 0.02° 2θ step scan from 1-50° with exposure time of 1s per step. No peaks could be resolved from the baseline for 2θ>35° therefore this region was not considered for further analysis.

Powder X-ray diffraction patterns (FIG. 1) of the two new COFs demonstrated their crystalline nature. In both cases, a strong diffraction peak appears at low angle–2θ=3.0° and 3.5°, respectively—along with some other peaks with lower diffraction intensities. No diffraction peaks were observed which could be attributed to starting materials. The observed diffraction peaks are relatively broad. Broadening in powder X-ray diffraction peaks is associated with several factors, including particle size, strain defects of the perfect lattice, and/or instrumental. There are many examples in the literature of porous materials exhibiting diffraction patterns with broad peaks, including for instance, ordered mesoporous silicas. These materials exhibit only long-range order, with a well-defined framework and pore systems, but the exact location of the silicon and oxygen atoms cannot be determined precisely. In the present cases, the broadening of the peaks can be attributed to a number of defects in the perfect crystal lattice, as well as to the particle size effects. The possibility of a lack of short-range order in the structure cannot be ruled out. Nevertheless, in contrast with the mesoporous silicas, where the number of possible combinations for the Si and O atoms positions in the frameworks is infinite, in the case of the COFs, the structural models are made based on geometrical features of the employed building blocks, which reduces the number of possibilities and allows us to propose crystalline materials models which explain the observed properties.

Structural Modeling:

All the models, including cell parameters and atomic positions were generated using the Materials Studio software package, employing the Materials Visualizer module. The porphyrin units were initially located with their centroid at the vertex positions of the sql layer type, obtained from the Reticular Chemistry Structure Resource (http://rcsr.anu.edu.au/layers/sql). Accordingly, all the models were constructed in the tetragonal system, with the layers lying on the ab plane. For the eclipsed models (AA stacking sequence) primitive unit cells were selected, while for the models with staggered porphyrins (AB stacking sequence) the models were constructed in body-centered cells. The space groups with the maximum possible symmetry were selected. An energetic minimization was performed to optimize the geometry of the building units, employing the universal forcefield implemented in the Forcite module of Materials Studio. During this process, the unit cell parameters for each model were also optimized. In Table 1 the values of the optimized unit cell parameters and the space group for the models constructed are summarized.

TABLE 1

Crystal data of simulated crystal structure in the eclipsed form (tetragonal space group).

| | COF-366 | | COF-66 | |
|---|---|---|---|---|
| Space group | eclipsed P4/m | staggered I4/m | eclipsed P4/mmm | staggered I4/mmm |
| a (Å) | 25.696189 | 25.598137 | 30.231459 | 30.23724 |
| c (Å) | 12.541469 | 12.354903 | 3.510071 | 6.600061 |

To elucidate the lattice packing, a model was constructed by using the Materials Studio software package. The square geometry of the porphyrin unit suggests the formation of the square layers with sql topology. Accordingly, modeling was performed in the tetragonal system, with the layers lying on the ab plane. Regarding the stacking of the layers, two extreme possibilities were evaluated—these are (i) a fully eclipsed model, with an AA stacking sequence, and (ii) a staggered model with an AB stacking sequence of layers, each layer translated from the next one by one half of the a and b lattice parameters. These two models were constructed in the space groups P4/mmm and I4/mmm, respectively, for COF-66, and in the space groups P4/m and I4/m, for COF-366. A geometrical energy minimization was performed using the universal force field implemented in the forcite module of Materials Studio, to optimize the geometry of the building molecules, as well as the unit cell parameters. When the powder diffraction patterns for the models were calculated and compared to the experimental ones, excellent agreements was observed with the fully eclipsed model in the case of both materials. A full profile pattern matching (Pawley) refinement was then carried out to refine the unit cell parameters for both structures, obtaining good agreement factors for both compounds. Therefore, both the materials may be described as being composed of square layers, laying on the ab plane and stacking along the 001 direction with interlayer distances between the centroids of the stacked porphyrin units of 5.64 and 3.81 Å for COF-366 and COF-66, respectively. Hollow channels are produced, running along the c axis, with a diameter of 20.2 and 23.2 Å for COF-366 (FIG. 2) and COF-66 (FIG. 3) respectively, as calculated using the Platon cavity routine.

Figure 6:
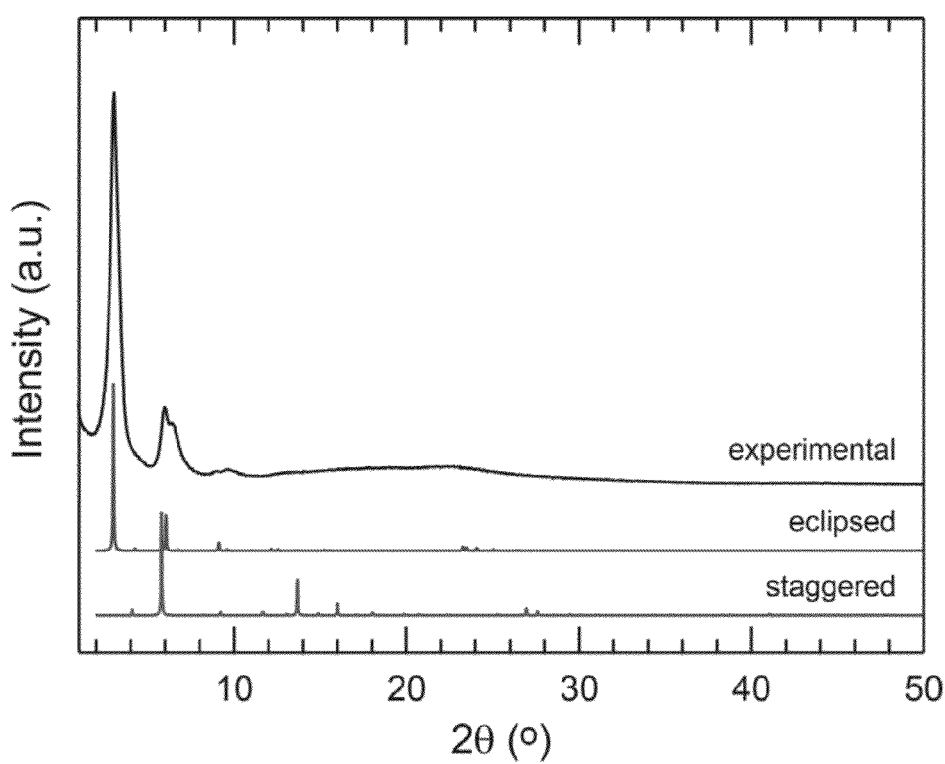
FIG. 6 shows simulated powder patterns for the staggered (dark grey) and eclipsed models (light grey) for COF-66. Experimental diffraction pattern was overlaid (black).

The corresponding powder patterns for the four models were calculated (FIGS. 5 and 6) and compared with the experimental ones, finding the best agreement for the eclipsed models. With them, a full profile pattern (Pawley) refinement was performed against the experimental powder patterns obtaining the refined unit cell parameters.

In Tables 2 and 3 the refined cell parameters and the fractional atomic coordinates of the two final models can be found.

TABLE 2

Refined unit cell parameters and fractional atomic coordinates for COF-366.
Name COF-366
Space group P4/m
a (Å) 25.4173
c (Å) 12.3767

| Atom name | x | y | z |
|---|---|---|---|
| C1 | 0.30609 | 0.0081 | 0.23573 |
| C2 | 0.2828 | 0.03394 | 0.3233 |
| C3 | 0.22839 | 0.03302 | 0.33919 |
| C4 | 0.46566 | 0.04299 | 0.14765 |
| C5 | 0.19469 | 0.00888 | 0.26464 |
| C6 | 0.13678 | 0.00741 | 0.28212 |
| N7 | 0.35909 | 0.01095 | 0.22387 |
| C8 | 0.21759 | 0.98255 | 0.16918 |
| C9 | 0.27181 | 0.98019 | 0.15746 |
| C10 | 0.38863 | 0.98257 | 0.15385 |
| C11 | 0.48003 | 0.9487 | 0.14551 |
| C12 | 0.44548 | 0.99162 | 0.14828 |
| N13 | 0.05918 | 0.94476 | 0.28741 |
| C14 | 0.11159 | 0.95463 | 0.28794 |
| C15 | 0.13996 | 0.90823 | 0.28992 |
| C16 | 0.05499 | 0.89156 | 0.28647 |
| C17 | 0.10434 | 0.8684 | 0.28609 |

TABLE 3

Refined unit cell parameters and fractional atomic coordinates for COF-66.
Name COF-66
Space group P4/mmm
a (Å) 28.984
c (Å) 3.8133

| Atom name | x | y | z |
| --- | --- | --- | --- |
| C1  | 0.11501 | 0.00000  | 0.00000 |
| C2  | 0.16629 | 0.00000  | 0.00000 |
| C3  | 0.09167 | −0.04104 | 0.00000 |
| C4  | 0.41990 | 0.95312  | 0.00000 |
| C5  | 0.45999 | 0.97645  | 0.00000 |
| N6  | 0.04698 | 0.95302  | 1.00000 |
| C7  | 0.08128 | 0.88719  | 1.00000 |
| C8  | 0.19128 | 1.03942  | 1.00000 |
| C9  | 0.23746 | 1.03975  | 1.00000 |
| O10 | 0.33844 | 1.04063  | 1.00000 |
| C11 | 0.61940 | 1.02279  | 1.00000 |
| C12 | 0.26067 | 1.00000  | 1.00000 |
| B13 | 0.31205 | 1.00000  | 1.00000 |
| C14 | 0.50000 | 0.04661  | 0.00000 |

Laser Flash Photolysis Time-Resolved Microwave Conductivity (FP-TRMC):

Flash-photolysis time-resolved microwave conductivity was performed using an in situ TRMC system. A resonant cavity was used to obtain a high degree of sensitivity in the conductivity measurement. The resonant frequency and microwave power were set at ~9.1 GHz and 3 mW, respectively, so that the electric field of the microwave was small enough not to disturb the charge carrier motion. The charge carriers were photochemically generated using the third harmonic generation (THG, λ=355 nm) light pulses from a Spectra-Physics model Quanta-Ray Nd: YAG laser (5-8 ns pulse duration) with an incident photon densities of $1.4-2.1\times10^{16}$ $cm^{-2}$. The TRMC signal, picked up by a diode (rise time<1 ns), was monitored by a Tektronics model TDS3052B digital oscilloscope. The observed conductivities were normalized, given by a photocarrier generation yield (φ) multiplied by sum of the charge carrier mobilities (Σμ), according to the equation, $\phi\Sigma\mu=(1/eAI_0F_{light})(\Delta P_r/P_r)$, where, e, A, $I_0$, $F_{light}$, $P_r$, and $\Delta P_r$ are the unit charge of a single electron, sensitivity factor ($S^{-1}$ cm), incident photon density of the excitation laser (photons $cm^{-2}$), filling factor ($cm^{-1}$), and reflected microwave power and its change, respectively. All the experiments were performed at room temperature in air. The values of φ were determined by conventional current integration technique in a vacuum chamber. Time-of-flight devices [Al/thin film sample/Indium Tin Oxide (ITO)] were irradiated by 355 nm laser with a photon density of $9.1\times10^{15}$ $cm^{-2}$. The applied bias was changed from 2 to 10 V.

The transient charge-carrier conductions of COF-366 and COF-66 were investigated by performing laser flash photolysis time-resolved microwave conductivity (FP-TRMC) measurements at 25° C. on irradiation with a 355-nm pulse laser at 3.5-3.6 mJ $cm^{-2}$ $pulse^{-1}$. The transient conductivity profile shows a rapid rise in current with a maximum Σμ value of $4.1\times10^{-5}$ $cm^2V^{-1}s^{-1}$ (COF-366) and $1.7\times10^{-5}$ $cm^2$ $V^{-1}s^{-1}$ (COF-66) at a photon density of $9.1\times10^{15}$ photons $cm^{-2}$, respectively (FIG. 4a). In order to determine the numbers of charge carriers, the time-of-flight transient was integrated at different bias voltages (FIG. 4b). The number of charge carriers estimated, by extrapolation from the bias at 0 V, were $3.2\times10^9$ (COF-66), $4.5\times10^9$ (COF-366), leading to the charge carrier generation yields Φ, expressed as the number of charge carriers/photon—of $1.5\times10^{-5}$ and $1.7\times10^{-5}$, respectively. Time-of-flight transient current integration measurements performed on a 1.5-μm thick COF-366 or COF-66/poly (methyl methacrylate) (PMMA) films (60/40 in wt %) between Al and indium tin oxide (ITO) electrodes reveal hole conduction in the case of both COFs. It transpires that COF-366 and COF-66 are p-type semiconductors with hole mobilities (Σμ) of 8.1 and 3.0 $cm^2V^{-1}s^{-1}$, respectively. The mobilities are high; both values are even higher than that of the inorganic amorphous silicon (~1 $cm^2V^{-1}s^{-1}$), one order of magnitude higher than that of the 'state-of-the-art' PBTTT (0.72 $cm^2V^{-1}s^{-1}$)[8] and P3HT (0.1~0.5 $cm^2V^{-1}s^{-1}$)[5] and at least four orders of magnitude higher than those of common conjugated polymers ($10^{-5}$~$10^{-6}$ $cm^2$ $V^{-1}s^{-1}$)[30], thus marking (FIG. 4a-b) COF-366 and COF-66 as the highest-mobility highly-ordered organic semiconductors yet known.

Generally, single crystals perform better in charge carrier transport as a result of the slowing down of the translational motion of charge carriers at the interfaces, impurities, boundaries, etc. In our measurements, without the long distant translational motion of charge carriers, the mobilities of the charge carriers are consistent with those in the crystals. Given the high mobility values of (8.1 $cm^2V^{-1}s^{-1}$), the electric field strength of microwave in the cavity of TRMC measurement (~10 V $cm^{-1}$), and the turn over interval of the microwave in the cavity (9 GHz of the probing microwave and Q value of the cavity ~2500), the spatial size of the oscillating motion of charge carriers in the TRMC measurement was estimated as ~5 nm at a maximum. Thus, it is presumed that the value estimated by TRMC will coincide with the value in the single crystal, if the average ordered structure of microcrystalline COFs is longer than 5 nm. The high-mobility carrier conduction is related to the eclipsed arrangements and n-conjugated intra-layer structures, accounting for the high mobility present in COF-366 than in COF-66.

Figure 7:
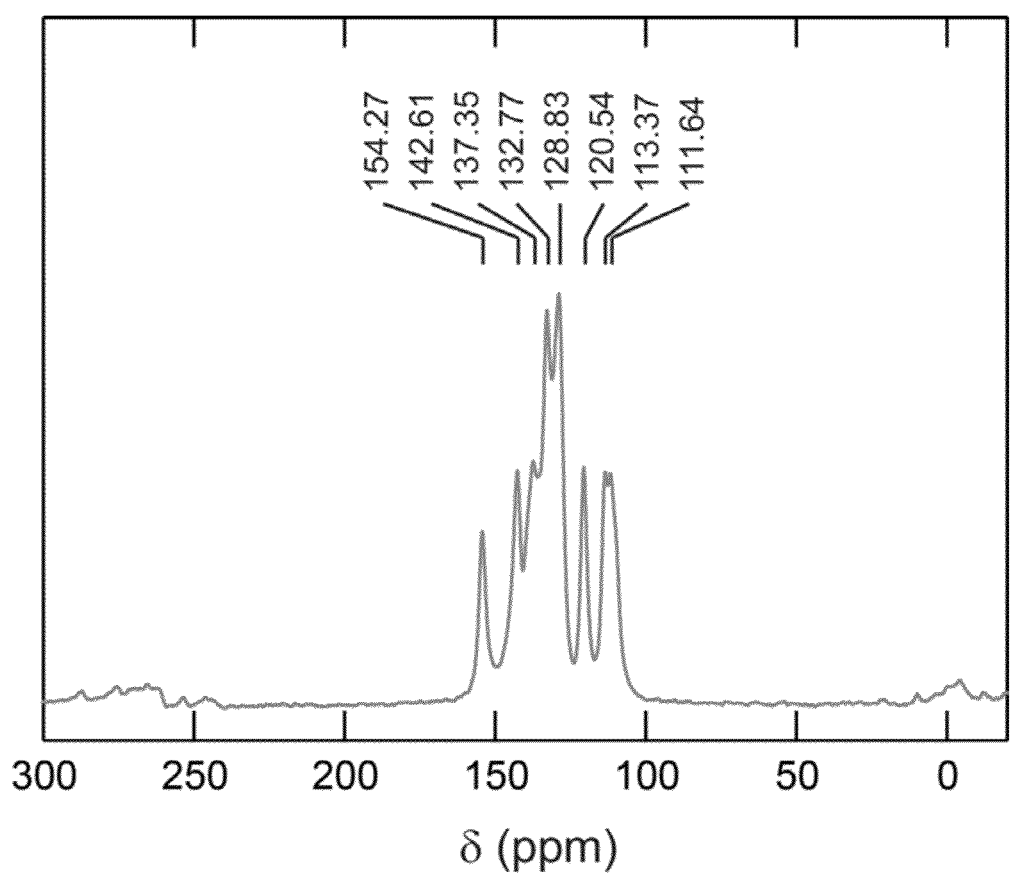
FIG. 7 shows solid-state $^{13}$C NMR spectrum for TAPP.
Figure 9:
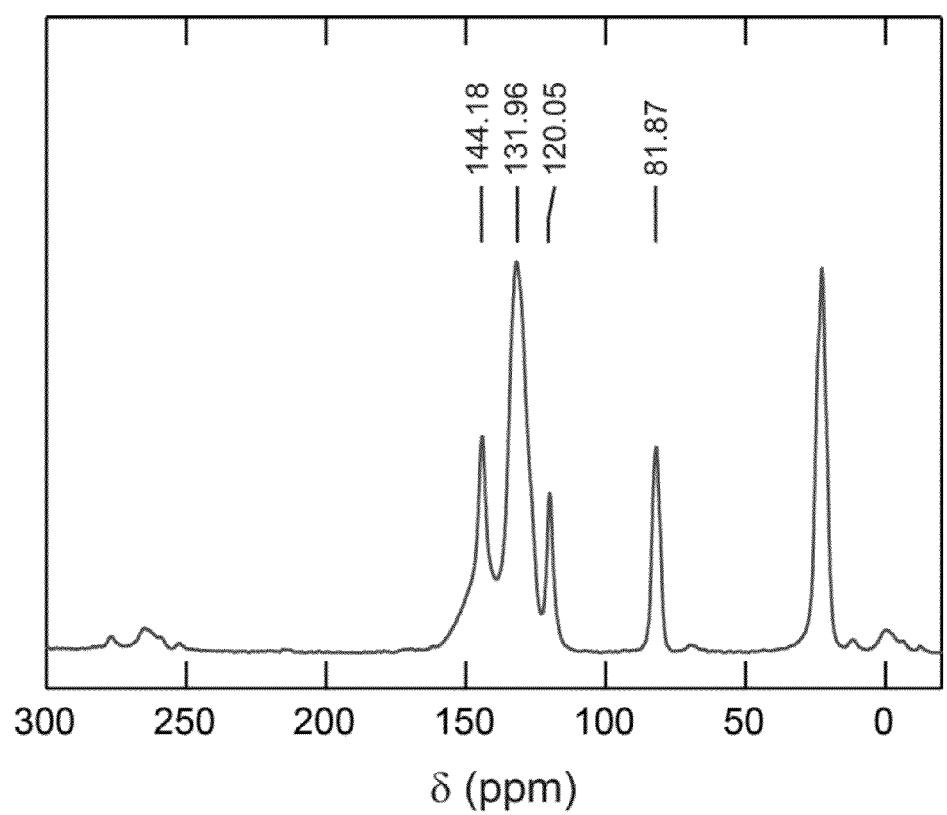
FIG. 9 shows Solid-state $^{13}$C NMR spectrum for TBPP.

High Resolution solid-state nuclear magnetic resonance (NMR):

NMR spectra were recorded at ambient pressure on a Bruker DSX-300 spectrometer using a standard Bruker magic angle-spinning (MAS) probe with 4 mm (outside diameter) zirconia rotors. The magic angle was adjusted by maximizing the number and amplitudes of the signals of the rotational echoes observed in the $^{79}$Br MAS FID signal from KBr. Cross-polarization with MAS (CP-MAS) used to acquire $^{13}$C data at 75.47 MHz. The $^1$H and $^{13}$C ninety-degree pulse widths were both 4 μs. The CP contact time varied from 1.5 to 5 ms. High power two-pulse phase modulation (TPPM) $^1$H decoupling was applied during data acquisition. The decoupling frequency corresponded to 72 kHz. The MAS sample-spinning rate was 10 kHz. Recycle delays between scans varied between 3 and 10 s, depending upon the compound as determined by observing no apparent loss in the $^{13}$C signal from one scan to the next. The $^{13}$C chemical shifts are given relative to tetramethylsilane as zero ppm, calibrated using the methylene carbon signal of adamantine assigned to 37.77 ppm as secondary reference. Various COFs and cores were studied using $^{13}$C NMR, and the tracings are provided as follows: TAPP (FIG. 7), COF-366 (FIG. 8), TBPP (FIG. 9), and COF-66 (FIG. 10).

Figure 11:
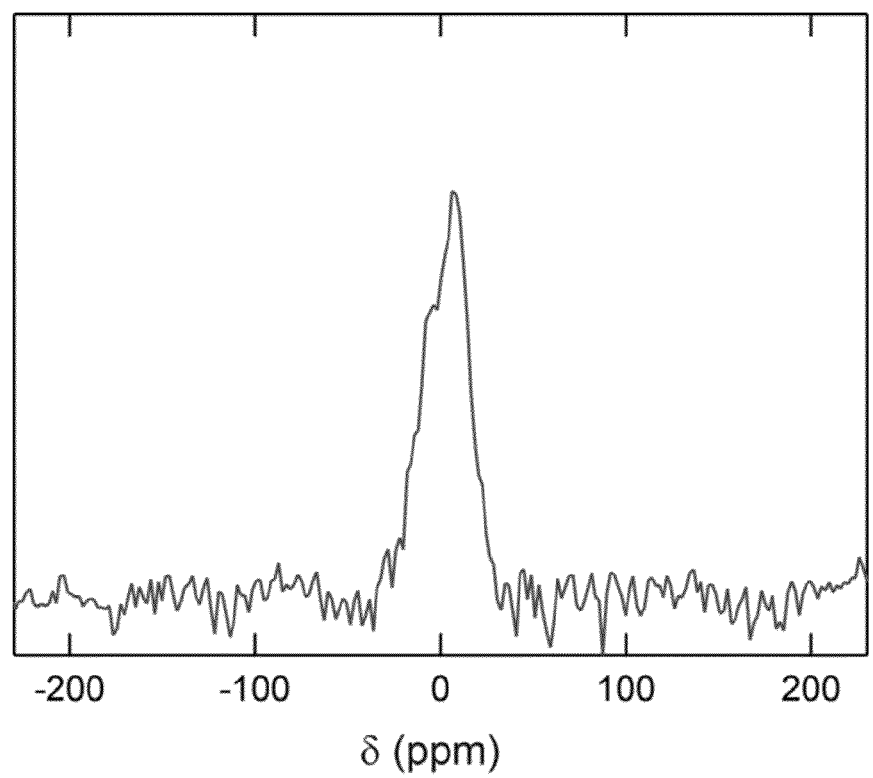
FIG. 11 shows the $^{11}$B MAS NMR spectrum for TBPP.
Figure 12:
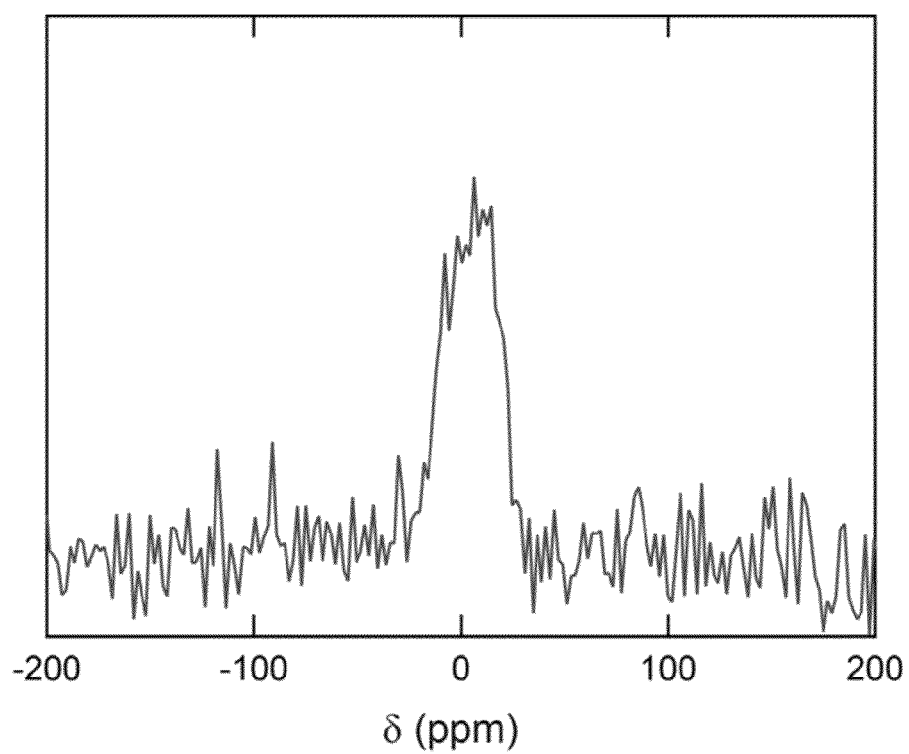
FIG. 12 shows the $^{11}$B MAS NMR spectrum for COF-66

$^{11}$B MAS Nuclear Magnetic Resonance Spectroscopy for TBPP and COF-66:

Multiple quantum MAS (MQ/MAS) spectroscopy was used to acquire $^{11}$B data at 96.29 MHz. The $^{11}$B solution-state ninety-degree pulse width was 2 μs. TPPM $^1$H decoupling was applied during data acquisition. The decoupling frequency corresponded to 72 kHz. The MAS spinning rate was 14.9 kHz. A recycle delay of 3 s was used. The $^{11}$B chemical shifts are given relative to $BF_3$ etherate as zero ppm, calibrated using aqueous boric acid at pH=4.4 assigned to −19.6 ppm as a secondary reference. The $^{11}$B MAS NMR tracing for TBPP is presented in FIG. 11 and the $^{11}$B MAS NMR tracing for COF-66 is presented in FIG. 12.

Figure 13:
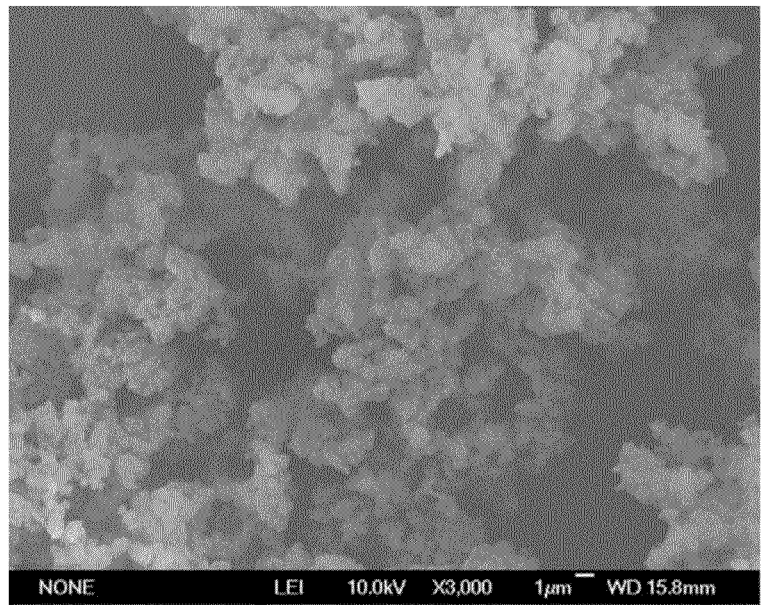
FIG. 13 shows an SEM image of COF-366.
Figure 14:
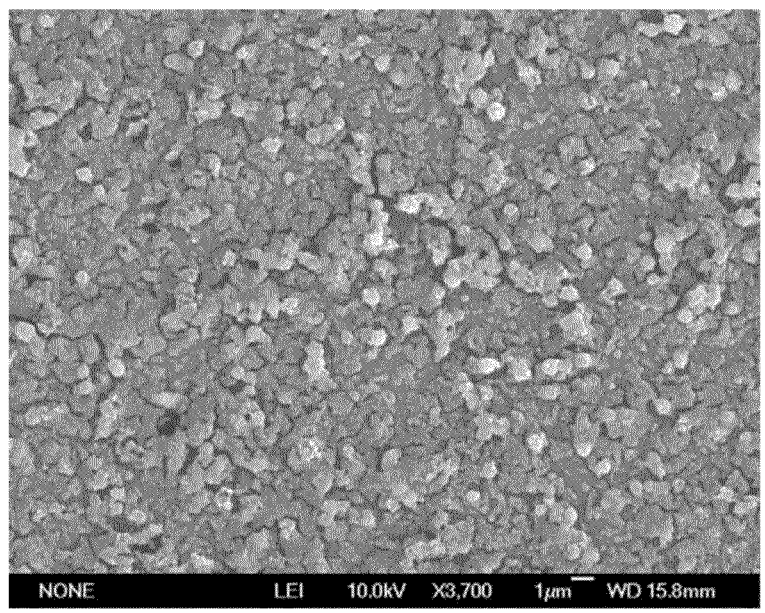
FIG. 14 shows an SEM image of COF-66.

Scanning Electron Microscopy Imaging (SEM) of COF-366 and COF-66:

Samples of all 2D COFs were prepared by dispersing the material onto a sticky carbon surface attached to a flat aluminum sample holder. The samples were then gold coated using a Hummer 6.2 Sputter at 60 mTorr of pressure in an argon atmosphere for 45 seconds while maintaining 15 mA of current. Samples were analyzed on a JOEL JSM-6700 Scanning Electron Microscope using both the SEI and LEI detectors with accelerating voltages ranging from 1 kV to 15 kV. The SEM image of COF-366 is presented in FIG. 13 and the SEM image of COF-66 is presented in FIG. 14.

Figure 15:
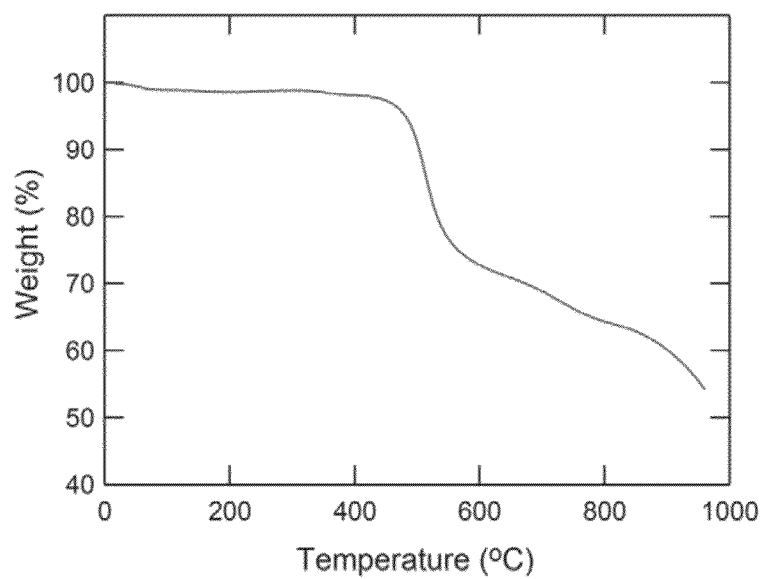
FIG. 15 shows a TGA trace for an activated sample of COF-366.
Figure 16:
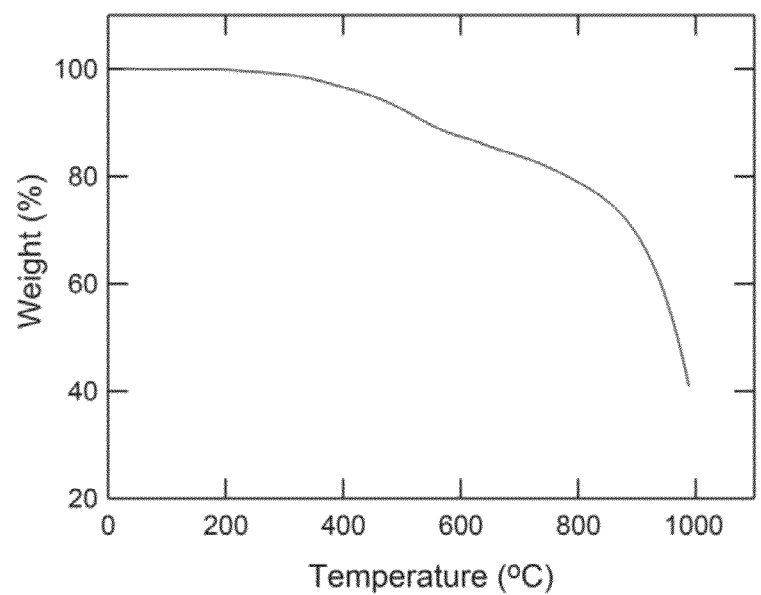
FIG. 16 shows a TGA trace for an activated sample of COF-66.

Thermal Gravimetric Analyses of COF-366 and COF-66:

Samples were run on a TA Instruments Q-500 series thermal gravimetric analyzer with samples held in platinum pans under atmosphere of nitrogen. A 5° C./min ramp rate was used. The thermal gravimetric analysis curve for COF-366 is shown in FIG. 15, and the thermal gravimetric analysis curve for COF-66 is shown in FIG. 16.

Figure 17:
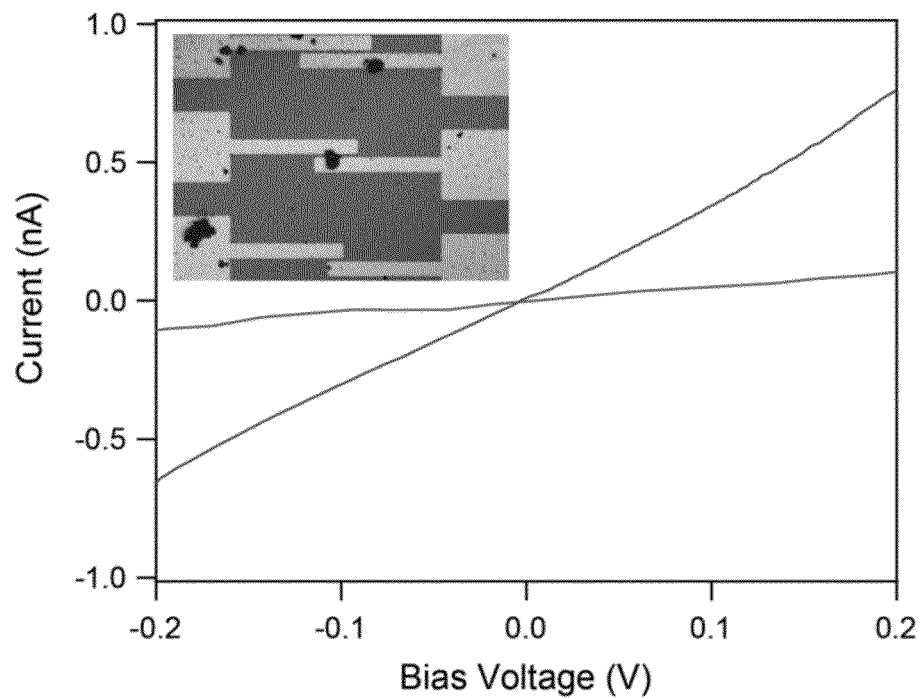
FIG. 17 shows I-V profiles of a 2 μm width Au gap with COF-366 (light grey) and COF-66 (medium grey). Inset: Gold electrode used for conductivity measurements.

Conductivity Measurements of COF-366 and COF-66:

The direct current (DC) electrical transport studies were conducted with a probe station at room temperature (25° C.) under ambient conditions with a computer-controlled analogue-to-digital converter. Bottom-contact devices were fabricated for both COFs. Gold electrodes were thermally deposited on a Si/SiO$_2$ substrate with a 300-nm SiO$_2$ layer to create channels that are 2-10 µm in length. One drop of COF dispersion was drop-cast onto the electrode, and the single pieces of two COFs were allowed to settle for a few seconds. The rest of the droplet was then quickly removed with flowing nitrogen and the devices blown thoroughly dry. Conductivity measurements were carried out directly after deposition using a standard probe station under ambient conditions. FIG. 17 presents an I-V profile of a 2 µm width Au gap with COF-366 (light grey) and COF-66 (medium grey). Inset: Gold electrode used for conductivity measurements.

Figure 18:
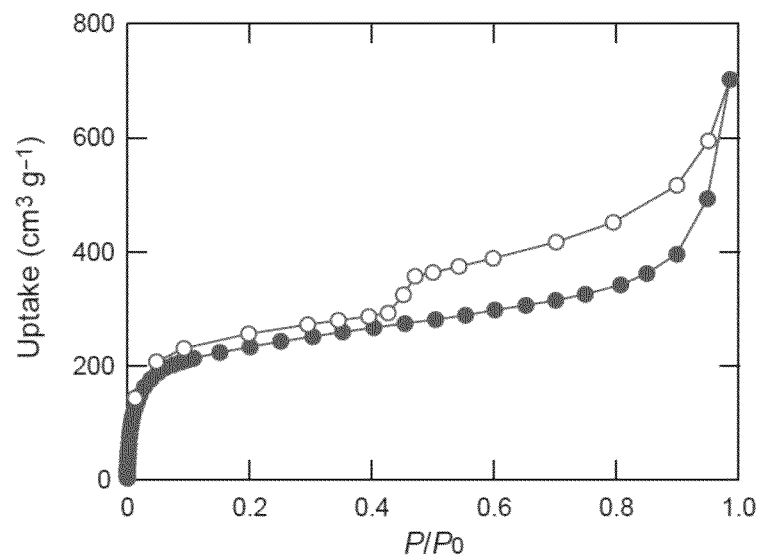
FIG. 18 shows Argon adsorption isotherm for COF-366 measured at 87 K.
Figure 19:
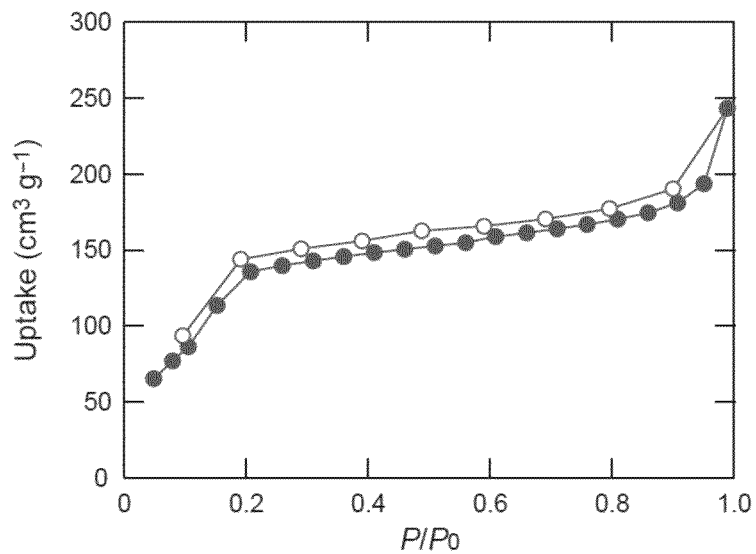
FIG. 19 shows Argon adsorption isotherm for COF-66 measured at 87 K.

Gas Adsorption Measurements and Non-Local DFT Pore Size Distributions for COF-366 and COF-66:

Low-pressure Ar adsorption measurements were performed on an Autosorb-1 (Quantachrome) volumetric analyzer. The samples were outgassed to 10$^{-6}$ Torr. Helium was used for the estimation of the dead volume, assuming that it is not adsorbed at any of the studied temperatures. A liquid Ar bath was used for adsorption measurements at 87 K. To provide high accuracy and precision in determining P/P$_0$, the saturation pressure P$_0$ was measured throughout the Ar analyses by means of a dedicated saturation pressure transducer, which allowed us to monitor the vapor pressure for each data point. Ultra-high-purity grade Ar and He (99.999% purity) were used throughout the adsorption experiments. The COF-366 and COF-66 argon isotherms (FIG. 18 and FIG. 19) show significant uptake in the low-pressure region (P/P$_0$<0.1), which is indicative of the porous character. The Langmuir (Brunauer-Emmett-Teller (BET)) surface areas for COF-366 and COF-66 were calculated to be 950 (735) and 610 (360) m$^2$ g$^{-1}$, respectively. Estimated pore volumes based on a Dubinin-Raduskavich (DR)-plot method for COF-366 and COF-66 are 0.32 and 0.20 cm$^3$ g$^{-1}$, respectively.

Figure 20:
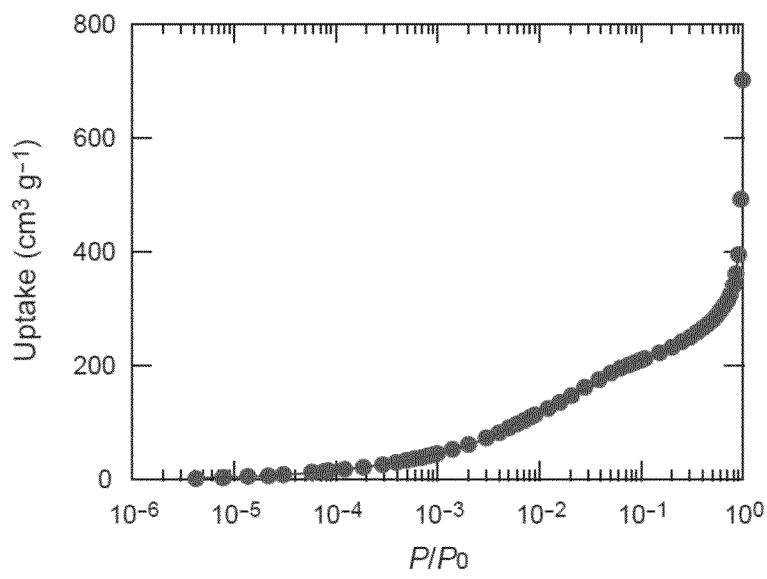
FIG. 20 shows Ar adsorption isotherm at 87 K for COF-366, comparison between experimental (circles) and NLDFT isotherm (grey line).
Figure 21:
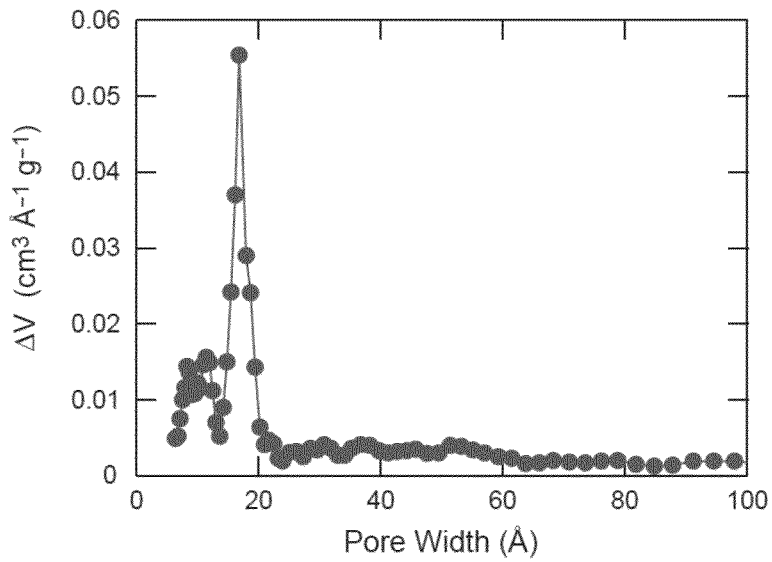
FIG. 21 shows Pore size distribution for COF-366, calculated from a NLDFT fit to the Ar adsorption data for COF-366 in FIG. 20.
Figure 22:
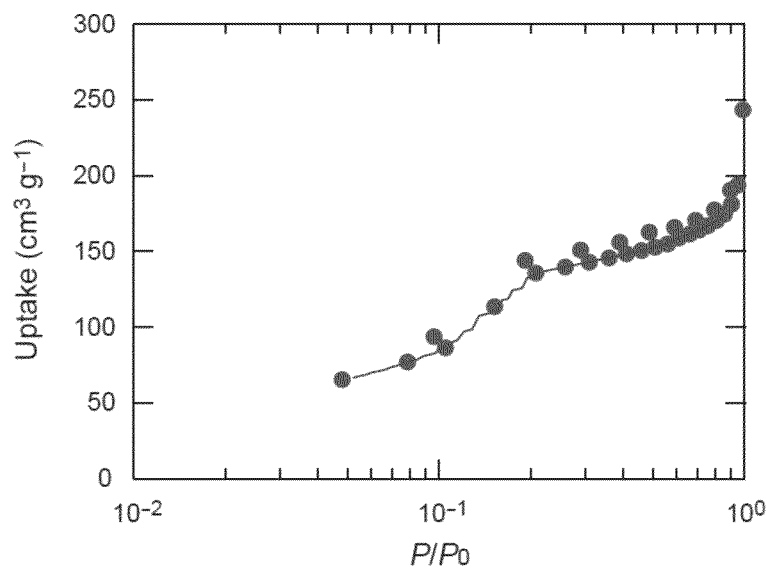
FIG. 22 shows Ar adsorption isotherm at 87 K for COF-66, comparison between experimental (circles) and NLDFT isotherm (grey line).

To estimate pore size distributions for COF-366 and COF-66, Ar isotherms were analyzed using nonlocal density functional theory (NLDFT) implementing a hybrid kernel for Ar adsorption at 87 K based on a zeolite/silica model containing spherical/cylindrical pores. A comparison between the NLDFT predicted curve (grey line) with actual COF-366 isotherm data (dark circles) is presented in FIG. 20. From which, the pore size distribution for COF-366, based on a NLDFT fit to the Ar adsorption data for COF-366, is presented in FIG. 21. A comparison between the NLDFT predicted curve (dark line) with COF-66 isotherm data (dark circles) is presented in FIG. 22. From which, the pore size distribution for COF-66, based on a NLDFT fit to the Ar adsorption data for COF-66, is presented in FIG. 23.

UV-Vis Diffuse Reflectance and Fluorescence Spectra of COF-366 and COF-66:

UV-Vis diffuse reflectance spectra (in Kubelka-Munk unit) were recorded on a JASCO model V-570 spectrometer equipped with integration sphere. Fluorescence Spectra were recorded on a Hitachi F-2700 fluorescence spectrometer.

In the UV-Vis diffuse reflectance spectra, COF-66 and COF-366 exhibited an absorption band at 402 and 417 nm, respectively (light grey lines in FIG. 23A-B), originated to the B band. The band is blue-shifted by 17 and 19 nm from that of the monomer precursors (solid; 416 and 430 nm; medium grey lines in FIG. 24A-B) (in DMF; 420 and 436 nm; dark grey lines in FIG. 24A-B). This blue shift indicates the formation of H-aggregates of porphyrin units in the stacked structures, which is in good agreement with proposed structures.

Figure 25:
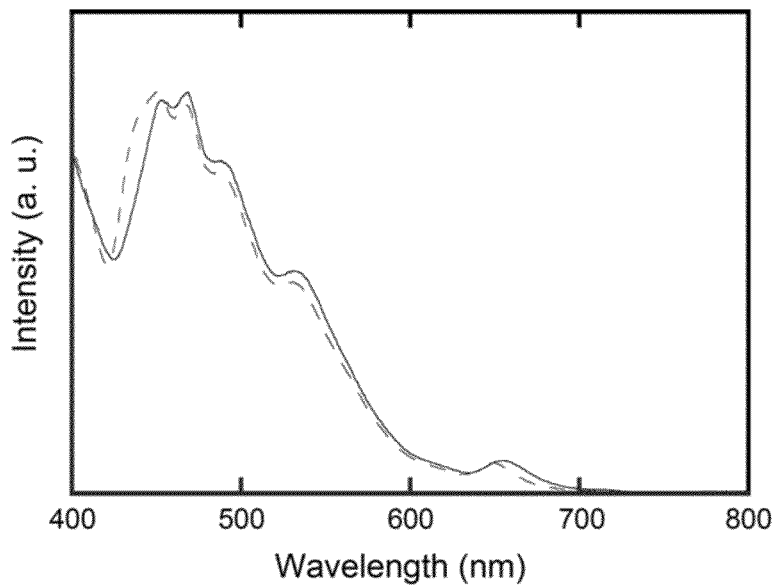
FIG. 25 shows the Fluorescence Spectra of (a) COF-366 (dashed line) and (b) COF-66 (solid line) upon excitation at 280 nm at 25° C.

There was only a slight difference between COF-366 and COF-66 upon excitation at 280 nm at 25° C. (See FIG. 25, wherein COF-366 is represented by a dash line and COF-66 is represented as a solid line).

Figure 26:
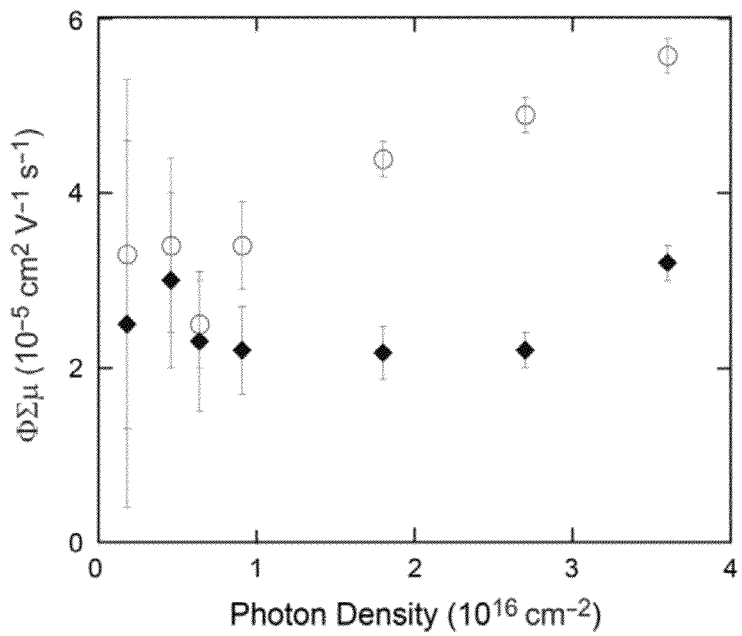
FIG. 26 shows FP-TRMC profiles of COF-366 (light grey) and COF-66 (dark grey) at 25° C. on irradiation with a 355-nm pulse laser with different photon densities: $3.6 \times 10^{16}$, $2.7 \times 10^{16}$, $1.8 \times 10^{16}$, $9.1 \times 10^{15}$, $6.4 \times 10^{15}$, $4.6 \times 10^{15}$, and $1.8 \times 10^{15}$ photons cm$^{-2}$, respectively. The ΦΣμ values were almost constant when the photon density decreased to the level of $10^{15}$ photons cm$^{-2}$.

FP-TRMC Profiles at Different Photon Densities:

FP-TRMC profiles (FIG. 26) of COF-366 (open circles) and COF-66 (diamonds) at 25° C. on irradiation with a 355-nm pulse laser with different photon densities: 3.6×10$^{16}$, 2.7×10$^{16}$, 1.8×10$^{16}$, 9.1×10$^{15}$, 6.4×10$^{15}$, 4.6×10$^{15}$, and 1.8× 10$^{15}$ photons cm$^{-2}$, respectively. The ΦΣµ values were almost constant when the photon density decreased to the level of 10$^{15}$ photons cm$^{-2}$. FIG. 26 shows there is a small dependence on the excitation density of photons for the COFs. This implies that the bimolecular (second order) recombination processes are not the dominant processes in the present case, and even at the lower excitation density, almost identical values of conductivity were observed for the materials.

Transient Photoabsorption of COF-66 and COF-366 Bound in PMMA Matrix.

Figure 27:
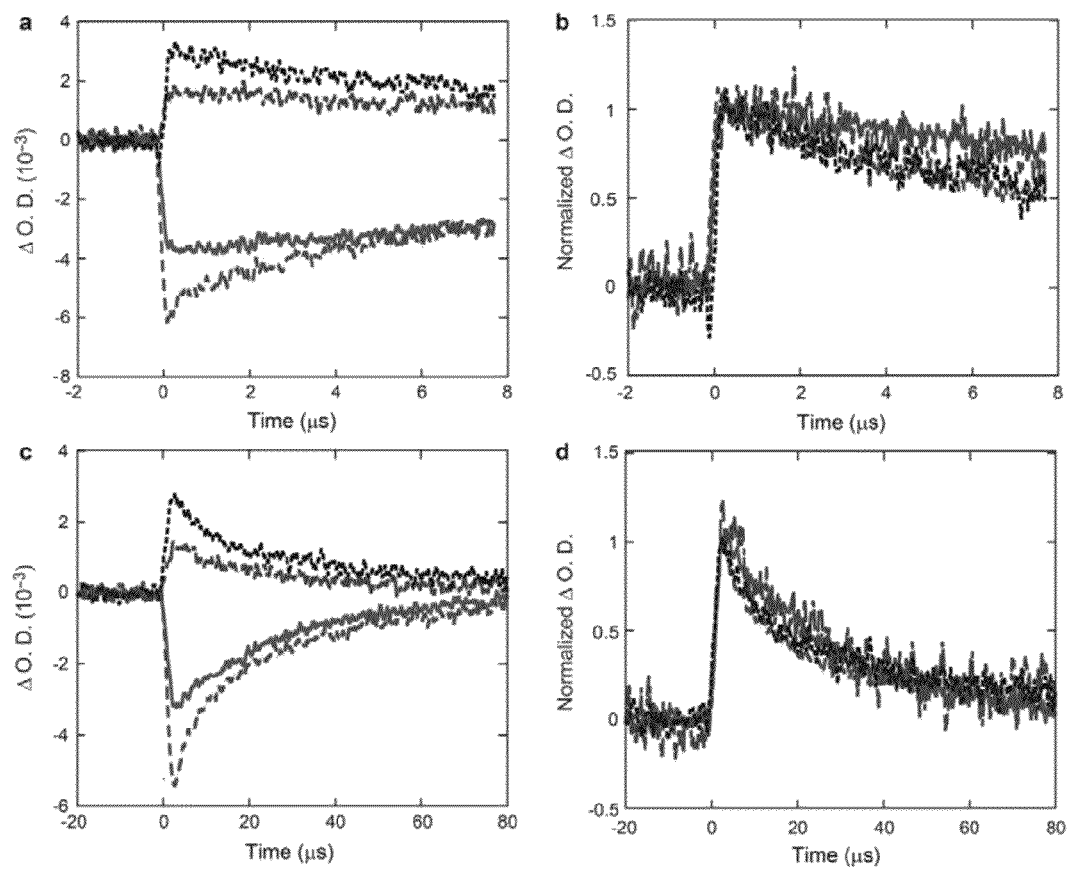
FIG. 27A-D shows Kinetic traces of transient photoabsorption observed for COF-366 (A-B) and COF-66 (C-D) bound in PMMA matrix (COF: PMMA=2:3 w/w) upon exposure to the 355-nm line of Nd:YAG laser ($2.7 \times 10^{16}$ cm$^{-2}$). The light grey, dark grey, medium grey, and black lines are the decays at 460 and 540 nm of COF-66 (C-D), 440 and 510 nm of COF-366 (A-B), respectively. These graphs show that the kinetic traces of transient photo-absorption demonstrate almost identical decay constants for both bleaching and absorption processes.

COF-366 and COF-66 bound in a PMMA matrix (COF: PMMA=2:3 w/w) were exposed to the 355-nm line of Nd: YAG laser (2.7×10$^{16}$ cm$^{-2}$). From which, kinetic traces of transient photoabsorption were plotted and decay constants were calculated. In FIG. 27, the light grey, dark grey, medium grey, and black lines presents the decays at 460 and 540 nm of COF-66, 440 and 510 nm of COF-366, respectively. COF-366 and COF-66 demonstrate almost identical decay constants for both bleaching and absorption processes.

End-of-Pulse Photoabsorption of COF-66 and COF-366 Bound in PMMA Matrix.

COF-366 and COF-66 bound in a PMMA matrix (COF: PMMA=2:3 w/w) were exposed to the 355-nm line of Nd: YAG laser (2.7×10$^{16}$ cm$^{-2}$). From which, traces of end-of-pulse photoabsorption were plotted. Transient photoabsorption spectra at the end-of-pulse observed for COF-366 (light grey) and COF-66 (dark grey) are presented in FIG. 28. In FIG. 28, the new absorption bands around 540 and 510 nm in the transient spectra (for COF-66 and COF-366, respectively), indicates the porphyrin cores form radical cations.

FP-TRMC Profiles at Different Excitation Powers:

COF-66 and COF-366 bound in a PMMA matrix (COF: PMMA=2:3 w/w) were exposed to a 355-nm line of Nd: YAG laser where the excitation power of the laser was varied from 0.64 to 3.6×10$^{16}$ cm$^{-2}$. FIG. 29 presents the normalized FP-TRMC transient photoabsorption spectra for COF-66 and COF-366 for 0.64 (light/medium grey), 0.91 (dark grey), 1.8 (medium grey), 2.7 (black), and 3.6 (light grey)×10$^{16}$ cm$^{-2}$ excitation powers.

Normalized Decays of FP-TRMC Transient and TAS Signal of COF-66 and COF-366:

COF-66 and COF-366 bound in PMMA matrix (COF:PMMA=2:3, w/w) were exposed to the 355-nm line of Nd:YAG laser (2.7×10$^{16}$ cm$^{-2}$). The normalized decays were then determined. FIG. 30 presents the normalized decays of FP-TRMC transient (light grey) and TAS signal (dark grey) at 440 nm for COF-66 (a, b) and COF-366 (c, d). FIG. 30 indicates that the transients show good agreement with each other in the shorter time region; therefore, it is possible to obtain the 'pure' conductivity values in this region by subtracting the contribution from the thermal effect. FIG. 30(b, d) also shows the deviation in the two transient curves, especially in the longer time region. Moreover, the lifetimes of the charged species for both COFs are ~80 µs or even longer in spite of the higher mobility of the charge carriers. The lifetime of free charge carriers is the primary factor in the promotion of the effective charge carrier separation. Therefore, it is possible to consider fabricating a future hetero-junction type solar cell based on the COFs disclosed herein due to unexpectedly superior charge carrier separation.

Current Transients Observed under Positive Bias Mode in TOF Measurement of COF-66 and COF-366:

Current transients were measured under the positive bias mode at a variety of electric field strengths in the TOF measurement for COF-66 and COF-366. Excitation was carried out at 355 nm, 9.1×10$^{15}$ photons cm$^{-2}$. The TOF measurements for (a) COF-66 and (b) COF-366 are presented in FIG. 31. The linear plot of current transients under positive and negative bias modes at 1.1×10$^4$ V·cm$^{-1}$ for COF-66 is presented in FIG. 31(c).

Figure 32:
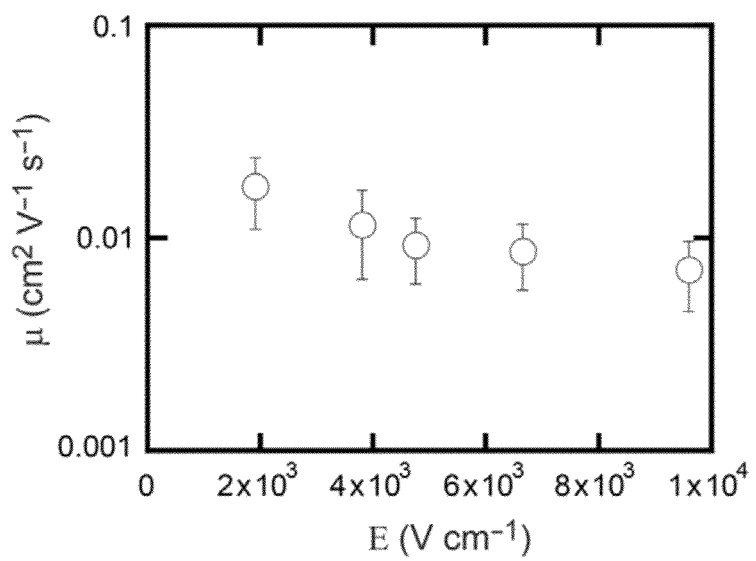
FIG. 32 shows dependence of hole drift mobility on applied electric field strength observed in a COF-66 film.

Dependence of Hole Drift Mobility on Applied Electric Field Strength Observed in a COF-66 Film:

In FIG. 32, the mobility decreases with an increase in the applied electric field strength (E), indicating "big" barriers for the hopping of charge carriers present along the path of the translational motion with a large distribution in the hopping distances. It is presumed that the negative slope in FIG. 31 is attributed to the presence of grain boundaries in the sample (see FIG. 32). By taking the intercept from the hole drift mobility data, the zero-field limit mobility value is estimated to be 0.05 cm$^2$ V$^{-1}$s$^{-1}$, which is close to the value in the TRMC experiment.

Figure 33:
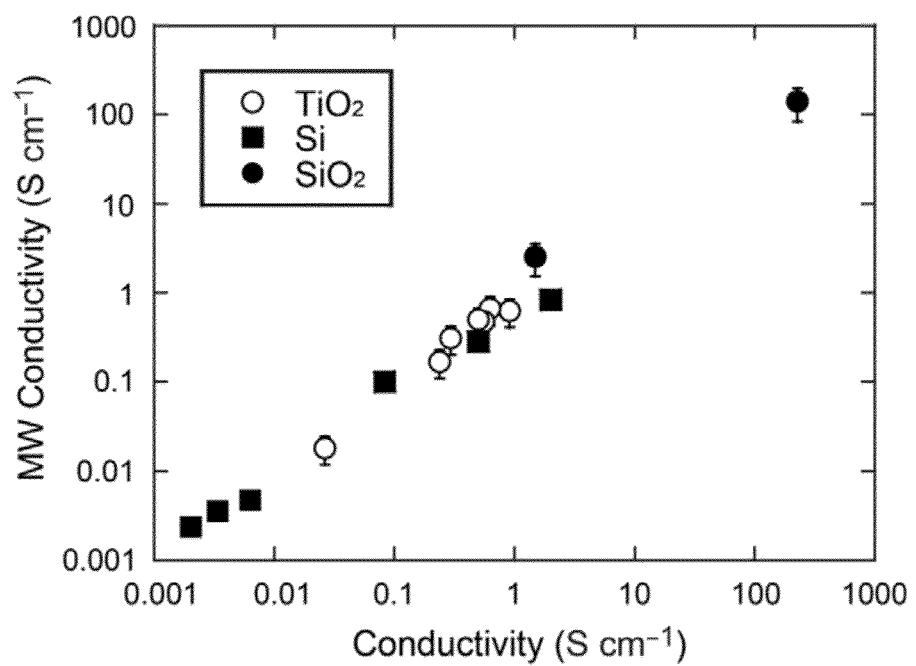
FIG. 33 shows correlation between the values of electric conductivity estimated by the non-contact microwave conductivity measurement and the conventional four-contacts/Hall effect measurement techniques in inorganic electric semi-conducting or conducting materials of Si (squares), TiO$_2$ (circles), and SnO$_2$ (solid circles) with a variety of dopant concentrations.

Correlation Between the Values of Electric Conductivity Estimated by the Non-contact Microwave Conductivity Measurement and the Conventional Four-contacts/Hall Effect Measurement Techniques:

There is a correlation between the values of electric conductivity estimated by the non-contact microwave conductivity measurement and the conventional four-contacts/Hall effect measurement techniques in inorganic electric semiconducting or conducting materials (See FIG. 33: Si (squares), TiO$_2$ (circles), and SnO$_2$ (solid circles) with a variety of dopant concentrations.

Our findings open up an avenue for exploiting plastic electronics and optoelectronics, based on COFs, which can be engineered at a molecular level with a wide range of π-conjugated networks.

Although a number of embodiments and features have been described above, it will be understood by those skilled in the art that modifications and variations of the described embodiments and features may be made without departing from the teachings of the disclosure or the scope of the subject matter as defined by the appended claims.

What is claimed is:

1. A conductive covalent-organic framework (COF) comprising:
a plurality of cores, wherein each core forms at least one covalent bond to at least one linking moiety; and
wherein at least one core of the plurality of cores comprises a conductive core moiety and/or wherein at least one linking moiety comprises a conductive linking moiety, wherein the at least one core is comprises Formula Ia:

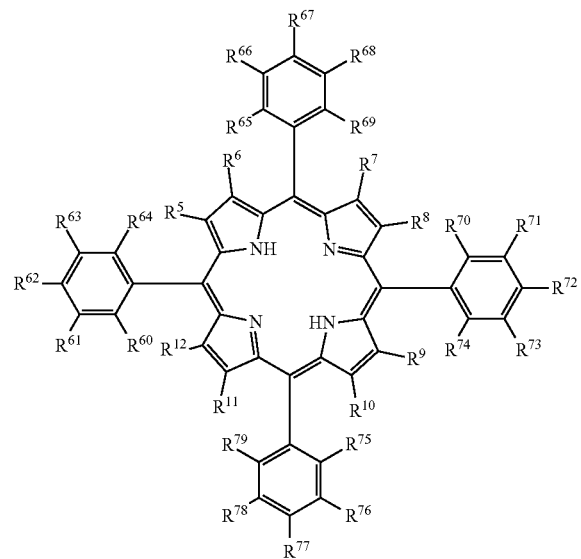

(Ia)

wherein $R^1$-$R^{12}$, $R^{60}$-$R^{79}$ are independently selected from the group consisting of H, D, FG, ($C_1$-$C_6$)alkyl, substituted ($C_1$-$C_6$)alkyl, ($C_1$-$C_6$)alkenyl, substituted ($C_1$-$C_6$)alkenyl, ($C_1$-$C_6$)alkynyl, substituted ($C_1$-$C_6$)alkynyl, hetero-($C_1$-$C_6$)alkyl, substituted hetero-($C_1$-$C_6$)alkyl, hetero-($C_1$-$C_6$)alkenyl, substituted hetero-($C_1$-$C_6$)alkenyl, hetero-($C_1$-$C_6$)alkynyl, substituted hetero-($C_1$-$C_6$)alkynyl, ($C_1$-$C_6$)cycloalkyl, substituted ($C_1$-$C_6$)cycloalkyl, aryl, substituted aryl, heterocycle, substituted heterocycle, wherein $R^5$ and $R^6$ are linked together to form a substituted or unsubstituted ring selected from the group consisting of cycloalkyl, aryl and heterocycle, wherein $R^7$ and $R^8$ are linked together to form a substituted or unsubstituted ring selected from the group consisting of cycloalkyl, aryl and heterocycle, wherein $R^9$ and $R^{10}$ are linked together to form a substituted or unsubstituted ring selected from the group consisting of cycloalkyl, aryl and heterocycle, and wherein $R^{11}$ and $R^{12}$ are linked together to form a substituted or unsubstituted ring selected from the group consisting of cycloalkyl, aryl and heterocycle.

2. The conductive COF of claim 1, wherein at least one other core has a structure selected from the group consisting of Formula I, II, III, IV, and V:

(I)

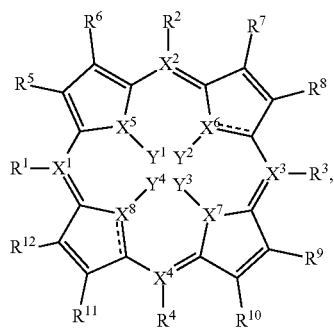

(II)

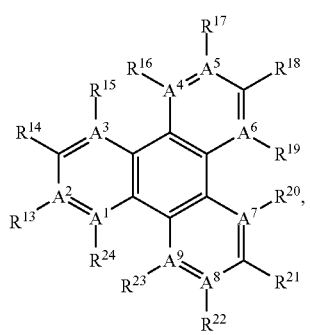

(III)

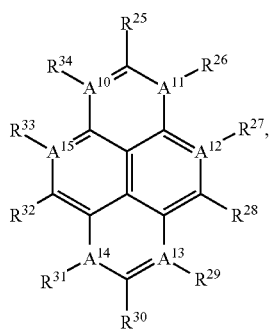

(IV)

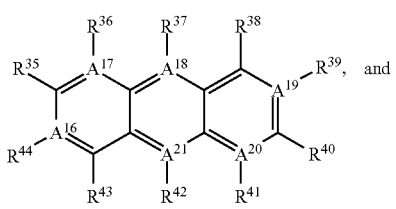

and (V)

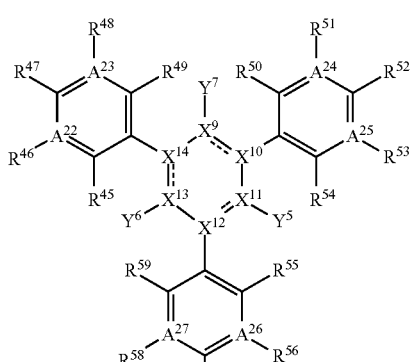

wherein:

$R^1$-$R^{59}$ are independently selected from the group consisting of H, D, FG, ($C_1$-$C_{20}$)alkyl, substituted ($C_1$-$C_{20}$) alkyl, ($C_1$-$C_{20}$)alkenyl, substituted ($C_1$-$C_{20}$)alkenyl, ($C_1$-$C_{20}$)alkynyl, substituted ($C_1$-$C_{20}$)alkynyl, hetero-($C_1$-$C_{20}$)alkyl, substituted hetero-($C_1$-$C_{20}$)alkyl, hetero-($C_1$-$C_{20}$)alkenyl, substituted hetero-($C_1$-$C_{20}$)alkenyl, hetero-($C_1$-$C_{20}$)alkynyl, substituted hetero-($C_1$-$C_{20}$) alkynyl, ($C_1$-$C_{20}$)cycloalkyl, substituted ($C_1$-$C_{20}$)cycloalkyl, aryl, substituted aryl, heterocycle, substituted heterocycle, wherein $R^5$ and $R^6$ are linked together to form a substituted or unsubstituted ring selected from the group consisting of cycloalkyl, aryl and heterocycle, wherein $R^7$ and $R^8$ are linked together to form a substituted or unsubstituted ring selected from the group consisting of cycloalkyl, aryl and heterocycle, wherein $R^9$ and $R^{10}$ are linked together to form a substituted or unsubstituted ring selected from the group consisting of cycloalkyl, aryl and heterocycle, and wherein $R^{11}$ and $R^{12}$ are linked together to form a substituted or unsubstituted ring selected from the group consisting of cycloalkyl, aryl and heterocycle;

$X^1$-$X^{13}$ are independently selected from the group consisting of carbon, oxygen, sulfur, silicon, phosphorous, and nitrogen;

$Y^1$-$Y^7$ are independently selected from the group consisting of H, D, and FG;

$A^1$-$A^{27}$ are independently selected from the group consisting of C, N, Si and P;

with the proviso that a X may not exceed its maximum valence by binding a Y, or $R^1$-$R^4$; and with the proviso that a A may not exceed its maximum valence by binding a R.

3. The conductive COF of claim 2, wherein the at least one other core has a structure of Formula I:

(I)

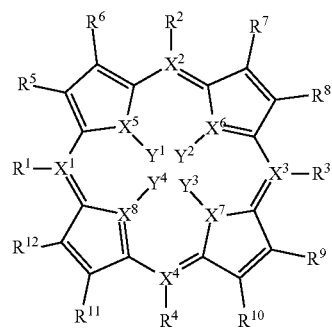

wherein, $R^1$-$R^{12}$ are independently selected from the group consisting of H, D, FG, ($C_1$-$C_6$)alkyl, substituted ($C_1$-$C_6$)alkyl, ($C_1$-$C_6$)alkenyl, substituted ($C_1$-$C_6$)alkenyl, ($C_1$-$C_6$) alkynyl, substituted ($C_1$-$C_6$)alkynyl, hetero-($C_1$-$C_6$) alkyl, substituted hetero-($C_1$-$C_6$)alkyl, hetero-($C_1$-$C_6$) alkenyl, substituted hetero-($C_1$-$C_6$)alkenyl, hetero-($C_1$-

$C_6$)alkynyl, substituted hetero-($C_1$-$C_6$)alkynyl, ($C_1$-$C_6$) cycloalkyl, substituted ($C_1$-$C_6$)cycloalkyl, aryl, substituted aryl, heterocycle, substituted heterocycle, wherein $R^5$ and $R^6$ are linked together to form a substituted or unsubstituted ring selected from the group consisting of cycloalkyl, aryl and heterocycle, wherein $R^7$ and $R^8$ are linked together to form a substituted or unsubstituted ring selected from the group consisting of cycloalkyl, aryl and heterocycle, wherein $R^9$ and $R^{10}$ are linked together to form a substituted or unsubstituted ring selected from the group consisting of cycloalkyl, aryl and heterocycle, and wherein $R^{11}$ and $R^{12}$ are linked together to form a substituted or unsubstituted ring selected from the group consisting of cycloalkyl, aryl and heterocycle;

$X^1$-$X^8$ are independently selected from the group consisting of carbon and nitrogen;

$Y^1$-$Y^4$ are independently selected from the group consisting of H, D, and FG; and with the proviso that a X may not exceed its maximum valence by binding a Y, or $R^1$-$R^4$.

4. The conductive COF of claim 3, wherein the at least one other core has a structure of Formula Ib:

(Ib)

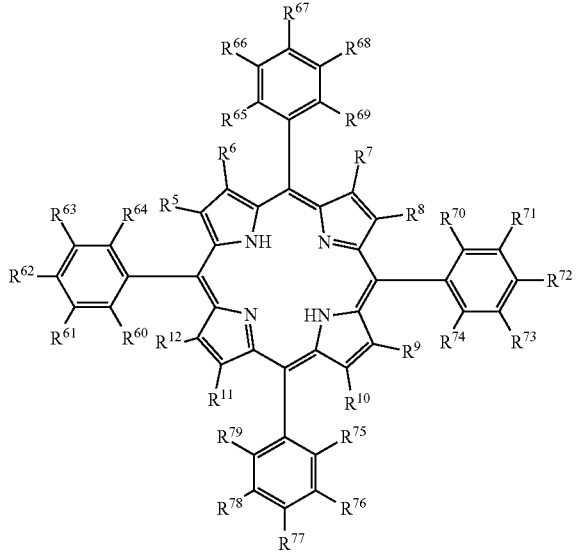

wherein, $R^1$-$R^4$, $R^{80}$-$R^{95}$ are independently selected from the group consisting of H, D, FG, ($C_1$-$C_6$)alkyl, substituted ($C_1$-$C_6$)alkyl, ($C_1$-$C_6$)alkenyl, substituted ($C_1$-$C_6$)alkenyl, ($C_1$-$C_6$)alkynyl, substituted ($C_1$-$C_6$)alkynyl, hetero-($C_1$-$C_6$)alkyl, substituted hetero-($C_1$-$C_6$)alkyl, hetero-($C_1$-$C_6$)alkenyl, substituted hetero-($C_1$-$C_6$)alkenyl, hetero-($C_1$-$C_6$)alkynyl, substituted hetero-($C_1$-$C_6$)alkynyl, ($C_1$-$C_6$)cycloalkyl, substituted ($C_1$-$C_6$)cycloalkyl, aryl, substituted aryl, heterocycle, and substituted heterocycle;

$X^1$-$X^4$ are independently selected from the group consisting of carbon and nitrogen; and with the proviso that a X may not exceed its maximum valence by binding a R.

5. The conductive COF of claim 1, wherein the at least one core has a structure of Formula Ia:

(Ia)

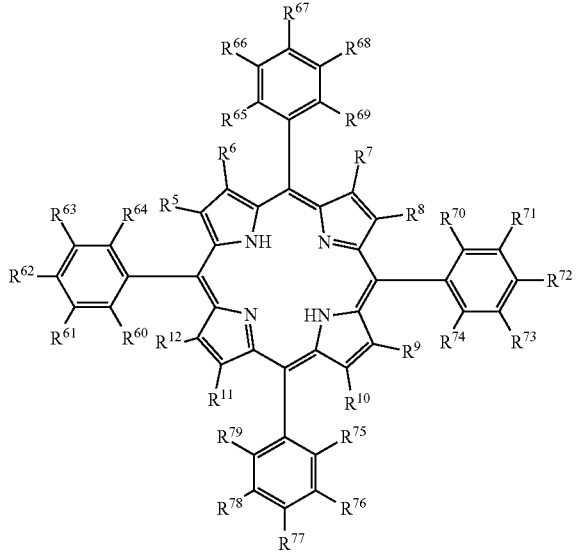

wherein, $R^1$-$R^{12}$, $R^{60}$-$R^{61}$, $R^{63}$-$R^{66}$, $R^{68}$-$R^{71}$, $R^{73}$-$R^{76}$, $R_{78}$-$R^{79}$ are H $R^{62}$, $R^{67}$, $R^{72}$, and $R^{77}$ are FG.

6. The conductive COF of claim 1, wherein one or more cores has a linking cluster that contains at least one heteroatom.

7. The conductive COF of claim 6, wherein the heteroatom is selected from the group consisting of B, O, N, S, Si, P, Al, F, Cl, Br, and I.

8. The conductive COF of claim 7, wherein the heteroatom is selected from the group consisting of B, and N.

9. The conductive COF of claim 6, wherein at least one linking cluster has the formula

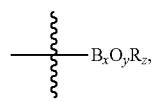

wherein x is number from 1 to 2, y is a number from 1 to 8, z is a number from 1 to 8, and R is selected from the group consisting of H, D, and FG.

10. The conductive COF of claim 1, wherein one or more linking moieties has an organic-based parent chain that is comprised of one or more substituted or unsubstituted rings; wherein one or more of these rings is further substituted with one or more functional groups, including additional substituted or unsubstituted hydrocarbons and heterocycle groups, or a combination thereof; and wherein the linking moiety contains at least one linking cluster.

11. The conductive COF of claim 1, wherein one or more linking moieties has a structure selected from the group consisting of Formula II, III, IV, V, VII, VIII, IX, and X:

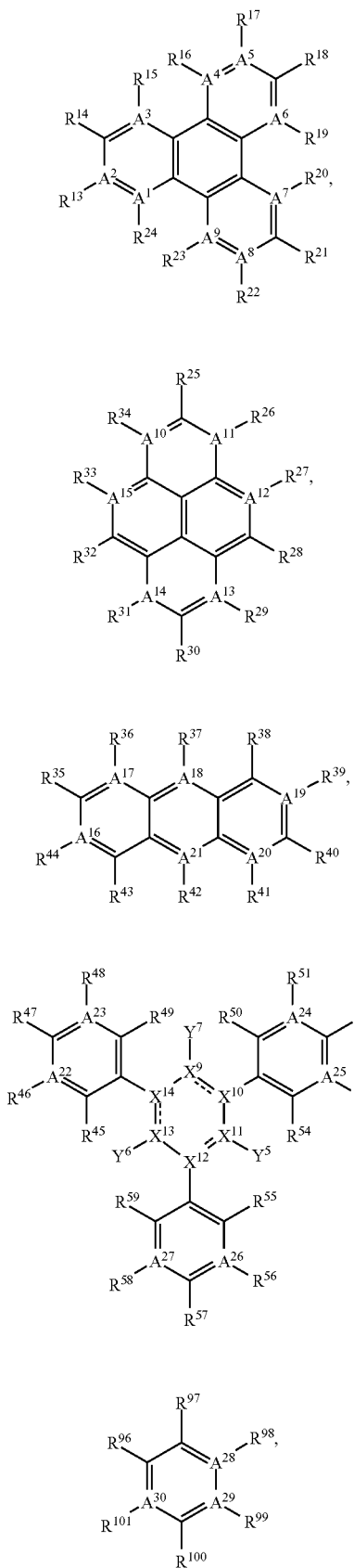

wherein:
A$^1$-A$^{56}$ are independently selected from the group consisting of C, Si, N and P;
n is a number from 1 to 8;
T is selected from the group consisting of an atom that can assume tetrahedral molecular geometry, a tetrahedral group, and a tetrahedral cluster;
R$^{13}$-R$^{145}$ are independently selected from the group consisting of H, D, FG, (C$_1$-C$_{20}$)alkyl, substituted (C$_1$-C$_{20}$)alkyl, (C$_1$-C$_{20}$)alkenyl, substituted (C$_1$-C$_{20}$)alkenyl, (C$_1$-C$_{20}$)alkynyl, substituted (C$_1$-C$_{20}$)alkynyl, hetero-(C$_1$-C$_{20}$)alkyl, substituted hetero-(C$_1$-C$_{20}$)alkyl, hetero- ($C_1$-$C_{20}$)alkenyl, substituted hetero-($C_1$-$C_{20}$)alkenyl, hetero-($C_1$-$C_{20}$)alkynyl, substituted hetero-($C_1$-$C_{20}$)alkynyl, ($C_1$-$C_{20}$)cycloalkyl, substituted ($C_1$-$C_{20}$)cycloalkyl, aryl, substituted aryl, heterocycle, and substituted heterocycle;

$X^9$-$X^{14}$ are independently selected from the group consisting of carbon, oxygen, sulfur, silicon, phosphorous, and nitrogen;

$Y^5$-$Y^7$ are independently selected from the group consisting of H, D, and FG;

with the proviso that a X may not exceed its maximum valence by binding a Y; and with the proviso that an A may not exceed its maximum valence by binding a R.

12. The conductive COF of claim 11, wherein one or more linking moieties has a structure of Formula IV:

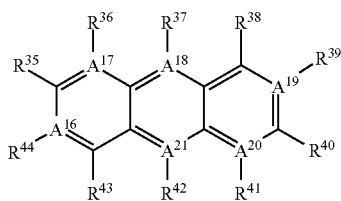

(IV)

wherein, $A^{16}$-$A^{21}$ are independently either C or N;

$R^{35}$-$R^{44}$ are independently selected from the group consisting of H, D, FG, ($C_1$-$C_6$)alkyl, substituted ($C_1$-$C_6$)alkyl, ($C_1$-$C_6$)alkenyl, substituted ($C_1$-$C_6$)alkenyl, ($C_1$-$C_6$)alkynyl, substituted ($C_1$-$C_6$)alkynyl, hetero-($C_1$-$C_5$)alkyl, substituted hetero-($C_1$-$C_5$)alkyl, hetero-($C_1$-$C_5$)alkenyl, substituted hetero-($C_1$-$C_5$)alkenyl, hetero-($C_1$-$C_5$)alkynyl, substituted hetero-($C_1$-$C_5$)alkynyl, ($C_1$-$C_8$)cycloalkyl, substituted ($C_1$-$C_8$)cycloalkyl, aryl, substituted aryl, heterocycle, and substituted heterocycle; and with the proviso that an A may not exceed its maximum valence by binding a R.

13. The conductive COF of claim 12, wherein one or more linking moieties has a structure of Formula IV:

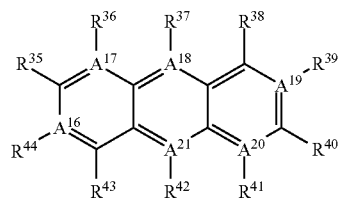

(IV)

wherein, $A^{16}$-$A^{21}$ are C;

$R^{36}$-$R^{48}$, $R^{41}$-$R^{43}$ are H; and $R^{35}$, $R^{44}$, $R^{39}$-$R^{40}$ are FG.

14. The conductive COF of claim 13, wherein one or more linking moieties has a structure selected from the group consisting of:

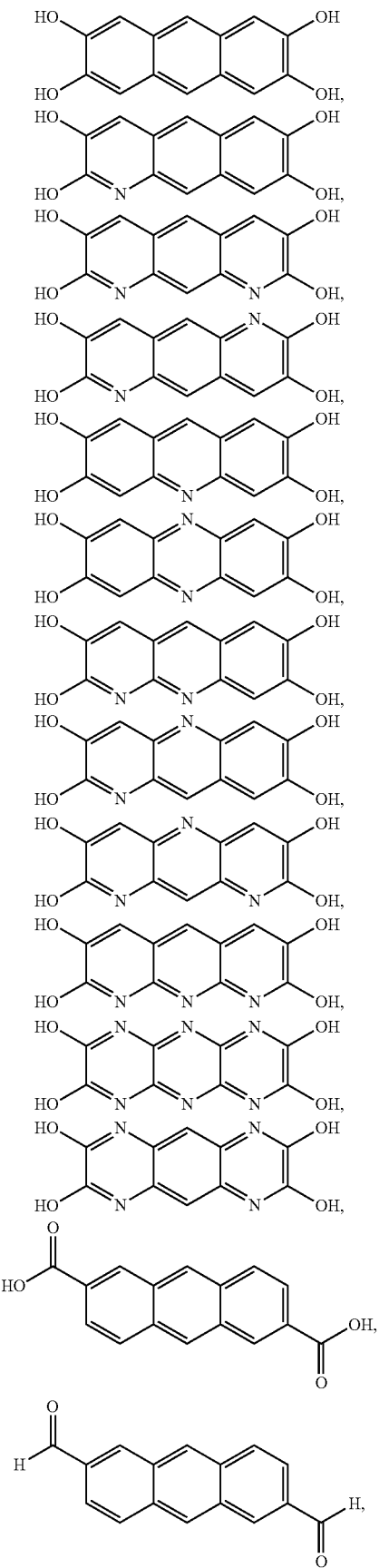

-continued

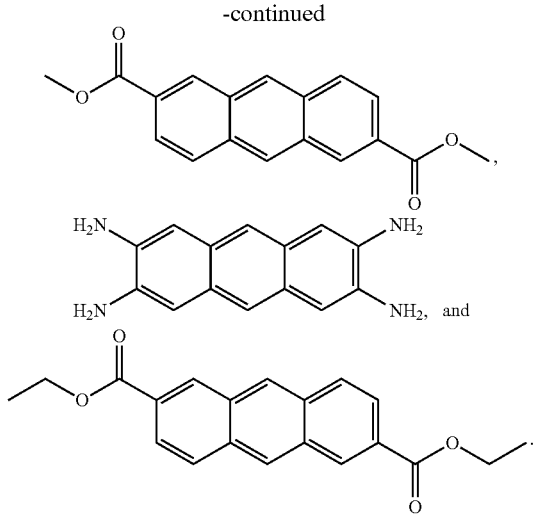

15. The conductive COF of claim 11, wherein one or more linking moieties has a structure of Formula VII:

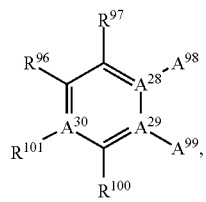

(VII)

wherein,
$A^{28}$-$A^{30}$ are independently either C or N;
$R^{96}$-$R^{101}$ are independently selected from the group consisting of H, D, FG, $(C_1$-$C_6)$alkyl, substituted $(C_1$-$C_6)$alkyl, $(C_1$-$C_6)$alkenyl, substituted $(C_1$-$C_6)$alkenyl, $(C_1$-$C_6)$alkynyl, substituted $(C_1$-$C_6)$alkynyl, hetero-$(C_1$-$C_5)$alkyl, substituted hetero-$(C_1$-$C_5)$alkyl, hetero-$(C_1$-$C_5)$alkenyl, substituted hetero-$(C_1$-$C_5)$alkenyl, hetero-$(C_1$-$C_5)$alkynyl, substituted hetero-$(C_1$-$C_5)$alkynyl, $(C_1$-$C_8)$cycloalkyl, substituted $(C_1$-$C_8)$cycloalkyl, aryl, substituted aryl, heterocycle, and substituted heterocycle; and
with the proviso that an A may not exceed its maximum valence by binding a R.

16. The conductive COF of claim 15, wherein one or more linking moieties has a structure of Formula VII:

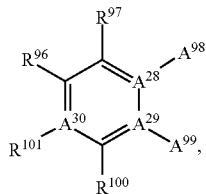

(VII)

wherein,
$A^{28}$-$A^{30}$ are C;
$R^{96}$, $R^{98}$-$R^{99}$, $R^{101}$ are independently either an H or D; and $R^{97}$ and $R^{100}$ are FG.

17. The conductive COF of claim 16, wherein one or more linking moieties has a structure selected from the group consisting of:

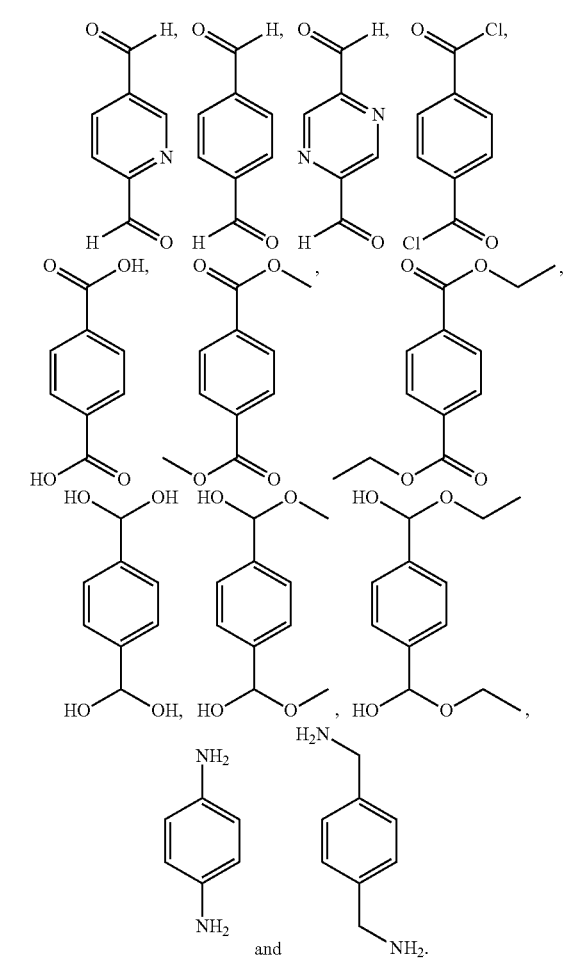

18. The conductive COF of claim 1, wherein one or more linking moieties has a linking cluster that contains at least one heteroatom.

19. The conductive COF of claim 18, wherein the heteroatom is selected from the group consisting of B, O, N, S, Si, P, Al, F, Cl, Br, and I.

20. The conductive COF of claim 19, wherein the heteroatom is selected from the group consisting of B, O, and N.

21. The conductive COF of claim 20, wherein at least one linking cluster has the formula

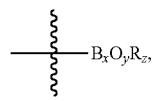

wherein x is number from 1 to 2, y is a number from 1 to 8, z is a number from 1 to 8, and R is selected from the group consisting of H, D, and FG.

22. The conductive COF of claim 18, wherein the linking cluster is selected from the group consisting of acyl halide, halide, ester, carboxylic acid, amine, hydroxyl, ether, and amide.

23. The conductive organic-framework of claim 1, wherein the framework is post-synthesis functionalized to comprise a metal or conductive moiety.

24. The conductive organic-framework of claim 1, wherein the COF has hole conducting mobilities of at least $3.0\ cm^2V^{-1}s^{-1}$.

25. The conductive organic-framework of claim 24, wherein the COF has hole conducting mobilities of at least $8.0\ cm^2V^{-1}s^{-1}$.

26. The conductive organic-framework of claim 1, wherein the COF can hold a charge for at least 75 µs.

27. A flexible display comprising the conductive organic-framework of claim 1.

28. A semiconductor comprising the conductive organic-framework of claim 1.

29. A gas storage device comprising the conductive organic-framework of claim 1.

30. A chemical sensor comprising the conductive organic-framework of claim 1.

* * * * *